US007691965B2

(12) United States Patent
Bielicki et al.

(10) Patent No.: US 7,691,965 B2
(45) Date of Patent: Apr. 6, 2010

(54) HELICAL SYNTHETIC PEPTIDES THAT STIMULATE CELLULAR CHOLESTEROL EFFLUX

(75) Inventors: John K. Bielicki, Castro Valley, CA (US); Pradeep Natarajan, Hacienda Heights, CA (US)

(73) Assignee: The Regents of the University of California, Oakland, CA (US)

( * ) Notice: Subject to any disclaimer, the term of this patent is extended or adjusted under 35 U.S.C. 154(b) by 508 days.

(21) Appl. No.: 11/014,187

(22) Filed: Dec. 15, 2004

(65) Prior Publication Data

US 2005/0202532 A1    Sep. 15, 2005

Related U.S. Application Data

(63) Continuation-in-part of application No. 10/142,238, filed on May 8, 2002, now Pat. No. 7,217,785.

(60) Provisional application No. 60/529,933, filed on Dec. 15, 2003.

(51) Int. Cl.
*C07K 14/00* (2006.01)
*C07K 2/00* (2006.01)
*C07K 1/00* (2006.01)
*C07K 7/00* (2006.01)
*A61K 38/00* (2006.01)
*A61K 38/02* (2006.01)
*A61K 38/16* (2006.01)

(52) U.S. Cl. .................. 530/324; 530/300; 530/333; 514/2; 514/12

(58) Field of Classification Search ............... 530/300, 530/324
See application file for complete search history.

(56) References Cited

U.S. PATENT DOCUMENTS

| | | | |
|---|---|---|---|
| 4,643,988 A | | 2/1987 | Segrest et al. |
| 5,721,114 A | | 2/1998 | Abrahamsen et al. |
| 5,733,549 A | | 3/1998 | Yamada et al. |
| 5,733,879 A | | 3/1998 | Rosseneu et al. |
| 5,876,968 A | | 3/1999 | Sirtori et al. |
| 5,955,055 A | | 9/1999 | Lees et al. |
| 6,004,925 A | * | 12/1999 | Dasseux et al. ............ 514/2 |
| 6,156,727 A | | 12/2000 | Garber et al. |
| 6,258,596 B1 | * | 7/2001 | Benoit et al. ............ 435/325 |
| 6,596,544 B1 | | 7/2003 | Fogelman et al. |
| 6,617,156 B1 | | 9/2003 | Doucette-Stamm et al. |
| 6,635,623 B1 | | 10/2003 | Hoogeveen et al. |
| 6,734,169 B2 | | 5/2004 | Dasseux et al. |
| 2003/0087819 A1 | | 5/2003 | Bielicki |

FOREIGN PATENT DOCUMENTS

WO    WO 00/55180 A2    9/2000
WO    WO 03/020765 A2    3/2003
WO    WO 2005/051998 A2    6/2005

OTHER PUBLICATIONS

Wetterau JR, Aggerbeck LP, Rall SC Jr., Weisgraber KH, Human Apolipoprotein E3 in Aqueous Solution, Journal of Biological Chemistry, 1988, 263(13): 6240-6248.*
Weisgraber KH, Rall SC, Bersot TP, Mahley RW, Apolipoprotein A-IMilano, The Journal of Biological Chemistry, 1983, 258(4): 2508-2513.*
Ameli, S., et al., "Recombinant Apolipoprotein A-I Milano Reduces Intimal Thickening After Balloon Injury in Hypercholesterolemic Rabbits," *Circulation*, Oct. 13, 1994, pp. 1935-1941, vol. 90, No. 4.
Arakawa, B., et al., "Helical Apolipoproteins Stabilize ATP-binding Cassette Transporter A1 by Protecting It from Thiol Protease-mediated Degradation," *The Journal of Biological Chemistry*, 2002, pp. 22426-22429, vol. 277, No. 25, USA.
Assman, G., et al., "High Density Lipoproteins, Reverse Transport of Cholesterol, and Coronary Artery Disease," *Circulation*, Apr. 13, 1993, pp. III, 28-34, vol. 87, No. 4.
Berendsen, HJC, "A Glimpse of the Holy Grail?" *Science*, 1998, pp. 642-643, vol. 282.
Bielicki, J.K., et al., "Apolipoprotein A-IMilano and Apolipoprotein A-iParis Exhibit an Antioxidant Activity Distinct From That of Wild-Type Apolipoprotein A-I," *Biochemistry*, Jan. 2002, pp. 2089-2096, vol. 41.
Bodzioch, M., et al., "The gene encoding'ATP-binding cassette transporter 1 is mutated in Tangier disease," *Nature Genetics*, 1999, pp. 347-351, vol. 22.
Brooks-Wilson, A., et al., "Mutations in ABC1 in Tangier disease and familial high-density lipoprotein deficiency," *Nature Genetics*, 1999, pp. 336-344, vol. 22.
Bruckert, E., et al., "The replacement of arginine by Cysteine at Residue 151 in Apolipoprotein A-I Produces a Phenotype Similar to that of Apolipoprotein A-IMilano," *Atherosclerosis*, 1997, pp. 121-128, vol. 128.
Brushia, R., et al., "Baculovirus-mediated expression and purification of human serum paraoxonase 1A," *Journal of Lipid Research*, Jun. 2001, pp. 951-958, vol. 42.
Chroni, A. et al., "The Central Helices of ApoA-I Can Promote ATP-binding. Cassette Transporter of A1 (ABCA1)-mediated Lipid Efflux," *J. Biol. Chem.*, 2003, pp. 6719-6730, vol. 278, USA.
Datta, et al.; "Aromatic Residue on the Nonpolar Face of Class A Amphipathic Helical Peptides Determines Biological Activity;" *The Journal of Biological Chemistry*; Jun. 18, 2004; pp. 26509-26517; vol. 279; No. 24; The American Society for Biochemistry and Molecular Biology, Inc.; USA.
Franceschini, G., et al., "A-IMilano Apoprotein: Decreased High Density Lipoprotein Cholesterol Levels with Significant Lipoprotein Modifications and Without Clinical Atherosclerosis in an Italian Family," *J. Clin. Invest.*, Nov. 1980, pp. 892-900, vol. 66.

(Continued)

*Primary Examiner*—Anish Gupta
*Assistant Examiner*—Julie Ha
(74) *Attorney, Agent, or Firm*—Townsend and Townsend and Crew LLP

(57) ABSTRACT

The present invention provides peptides comprising at least one amphipathic alpha helix and having an cholesterol mediating activity and a ABCA stabilization activity. The invention further provides methods of using such peptides.

19 Claims, 18 Drawing Sheets

OTHER PUBLICATIONS

Franceschini, G., et al., "Apolipoprotein A-I Milano: Accelerated Binding and Dissociation From Lipids of a Human Apolipoprotein Variant," *J. Biol. Chem.*, Dec. 1985, pp. 16321-16325, vol. 260, No. 30.

Francis, G., et al., "Defective Removal of Cellular Cholesterol and Phospholipids by Apolipoprotein A-I in Tangier Disease," *J. Clin. Invest*, 1995, pp. 78-87, vol. 96.

Garber, D., et al., "A new synthetic class A amphipathic peptide analogue protects mice from diet-induced atherosclerosis," *Journal of Lipid Research*, Apr. 2001, pp. 545-552, vol. 42.

Gillotte, K., et al., "Apolipoprotein-mediated plasma membrane microsolubilization," Journal of Biological Chemistry, Jan. 1999, pp. 2021-2028, vol. 272, No. 4.

Jia, Z., et al.; "Thiol-bearing Synthetic Peptides Retain the Antioxidant Activity of ApolipoproteinA-I(Milano);" *Biochemical and Biophysical Research Communications*: Sep. 20, 2002; pp. 206-213; vol. 297; Issue 2; Elsevier Science.

The Supplementary European Search Report for EP 04817040.1 dated Jul. 14, 2009 (6 pages).

Database GenSeq -- EBI Accession No. AABB58238, Mar. 14, 2001 "Lung cancer associated polypeptide SEQ ID No. 576" From WO 00/55180 A2.

Palgunachari et al.; "Only the two end helixes of eight tandem amphipathic helical domains of human apo A-I have significant lipid affinity: Implications for HDL assembly"; 1996; *Ateriosclerosis, Thrombosis, and Vascular Biology*; 16: 328-338.

Martinez, L. et al., "Phosphorylation of a Pest Sequence in ABCA1 Promotes Calpain Degradation and Is Reversed by ApoA-I," *J. Biol Chem.* 2003, pp. 37368-37374, vol. 278, USA.

McNeish et al., "High density lipoprotein dificiency and foam cell accumulation in mice with targeted disruption of ATP-binding casette trnaporter-1," *Proc. Natl. Acad. Sci.*, 2000, pp. 4245-4251, vol. 97, No.

Mendez, A., et al., "Synthetic Amphipathic Helical Peptides That Mimic Apolipoprotien A-I in Clearing Cellular Cholesterol," *J. Clin. Invest.*, Oct. 1994, pp. 1698-1705, vol. 94.

Mishra, V., et al., "Studies of Synthetic Peptides of Human Apolipoprotein A-I containing Tandem Amphipathic Alpha-Helixes," *Biochemistry*, Jun. 25, 1998, pp. 10313-10332, vol. 37.

Natarajan, et al., "Identification of an Apolipoprotein A-I Structural Element That Mediates Cellular cholesterol Efflux and Stablized ATP Binding Cassett Transporter A1," *J. Biol. Chem.*, 2004, pp. 24044-24052, vol. 279.

Navab, et al., "Thematic Review Series: The Pathogenesis of Atherosclerosis; The Oxidation Hypothesis of Atherogenesis: The Role of Oxidized Phospholipids and HDL;"; *Journal of Lipid Research*: Apr. 1, 2004; pp. 993-1008; vol. 45; The American Society for Biochemistry and Molecular Biology, Inc.

Oda, M., et al., "Cysteien Substitutions in Apolipoprotein A-I Primary Structure Modulate Paraoxonase Activity," *Biochemistry*, Jan. 19, 2001, pp. 1710-1718, vol. 40.

Palgunachari, et al., "Only the Tow End Helixes of Eight Tandem Amphipathic Helical Domains of Human Apo A-I Have Significant Lipid Affinity," *Arteriosclerosi, Thrombosis, and Vascular Biology*, Feb. 13, 1996, pp. 328-338, vol. 16.

Perez-Mendez, O., et al., "Metabolism of Apolipoproteins AI and AII in subjects carrying similar apoAI mutations, apoAI Milano and apoAI Paris," *Atherosclerosis*, 2000, pp. 317-326, vol. 148.

Reddy et al., "ATP-Binding Cassette Transporter 1 participates in LDL Oxidation by Artery Wall Cells;" *Arteriscler Thromb Vasc Biol.*; Nov. 2002, pp. 1877-1883; vol. 22.

Remaley, A. T., et al., "Decreased Revese Cholesterol Transport from Tangier Disease Fibroblasts," *Arterioscler, Thromb. Vasc. Biol.*, 1997, pp. 1813-1821, vol. 17.

Rifkind, B., "High-Density Lipoprotein Cholesterol and Coronary Artery Disease: Survey of the Evidence," *The American Journal of Cardiology*, Sep. 4, 1990, pp. 3A-6A, vol. 66.

Rudinge, J., "In: Peptide Hormones," *JA Parsons, Ed.*, 1976, pp. 1-7.

Saito, H., et al., "Domain Structure and Lipid Interaction in Human Apolipoproteins A-I and E, a Genral Model," *J. Biol. Chem.*, 2003, pp. 23227-23232, vol. 278, USA.

Saito, H., et al., "Cintributions of domain structure and lipid interaction to the functionality of exchangeable human apolipoproteins," *Prog. Lipid Res.*, 2004, pp. 350-380, vol. 43.

Schmitz, et al., "ATP-Binding Cassette Transporter A1 (ABCA1) in Macrophages: A Dual Function in Inflammation and Lipid Metabolism?;" *Pathobiology*: 2000; pp. 236-240; vol. 67; Karger AG; Basel.

Shah, P., et al., "High-dose Recombinatn Apolipoprotein A-I Milano Mobilizes Tissue Cholesterol and Rapidly Reduces Plaque Lipid and Macrophage Content In Apolipoprotein E-Deficient Mice," *Circulation*, Jun. 2001, pp. 3047-3050, vol. 103.

Shah, P., et al., "Effects of Recombinant Apolipoprotein A-I Milano on aortic Atherosclerosis in Apolipoprotein E-Deficient Mice," *Circulation*, Mar. 1998, pp. 780-785, vol. 97.

Sigma, "Designing Custom Peptides," http://ww.sigma-genosys.com/peptide_design.asp (Accessed Dec. 16, 2004).

Sirtori, C., et al., "Cardiovascular Status of Carriers of the Apoliprotein A-I Milano Mutant: The Limone sul Garda Study," *Circulation*, Apr. 2001, pp. 1949-1954, vol. 103.

Sorci-Thomas, M. G., et al., "Alteration in apolipoprotein A-I 22-mer repeat order rusults in a decrease in lecithin: cholesterol acyltransferase reactivity," J. Bio. Chem, Mar, 14, 1997, pp. 7278-7284, vol. 272.

Sorci-Thomas, M.G. et al., "The hydrophobic face orientation of apolipoprotein A-I amphipathic helix domain 143-164 regulates lecithin-cholesterol acyltransferase activiation," *J. Bio. Chem.*, May 8, 1998, pp. 11776-11782, vol. 273.

Utermann, G, et al., *Eur. J. Biochem*, 1984, pp. 325-331, vol. 144.

Voet, D., et al., *Biochemistry*, 2nd *Edition*, 1995, pp. 235-241.

Wang, N., et al., "A PEST sequence in ABCA1 regulates degradation by calpain protease and stabilizationof ABCA1 BY APOa-i," *J. Clin. Invest.*, Jan. 2003, pp. 99-107, vol. 111.

Wang, et al., "Specific Binding of ApoA-1, Enhanced Cholesterol Efflux, and Altered Plasma Membrane Morphology in Cells Expressing ABC1, " *J. Biol. Chem*, 2000, pp. 33053-33058, vol. 275, No. 42, USA.

Weisgraber, K.H., et al., "Apolipoprotein A-IMilano: Detection of Normal A-I in AffectedSubjects and Evidence for a Cysteine for Arginine Substitution In the Variant A-I," *J. Biol. Chem.*, Feb. 1983, pp. 2508-2513, vol. 285, No. 1.

Weisbraber, KLH., et al., "A-I Milano Apoprotein: Isolation and Characterization of Cysteine -containing Varient of the A-I Apoprotein from Humah High Density Lipoproteins," *J. Clin. Invest.*, Nov. 13, 1980, pp. 901-907, vol. 660

Wilson, P., "High-Density Lipoprotein, Low-Density Lipoprotein and Coronary Artery Disease," *Am. J. Cardiol.*, Sep. 4, 1990, pp. 7A-10A, vol. 66.

NCBI GenBank Accession number NP_44320. accessed at http://ww.ncbi.nlm.nih.gob.gquery/gquery.fcgi. Accessed Dec. 10, 2005, 1 page.

NCBI GenBank Accession number XP_043694. accessed at http://ww.ncbi.nlm.hih.gov/entrez/sutlis/girevhist.cgi?val=XP_043694. Accessed Feb. 10, 2005, 3 pages.

* cited by examiner

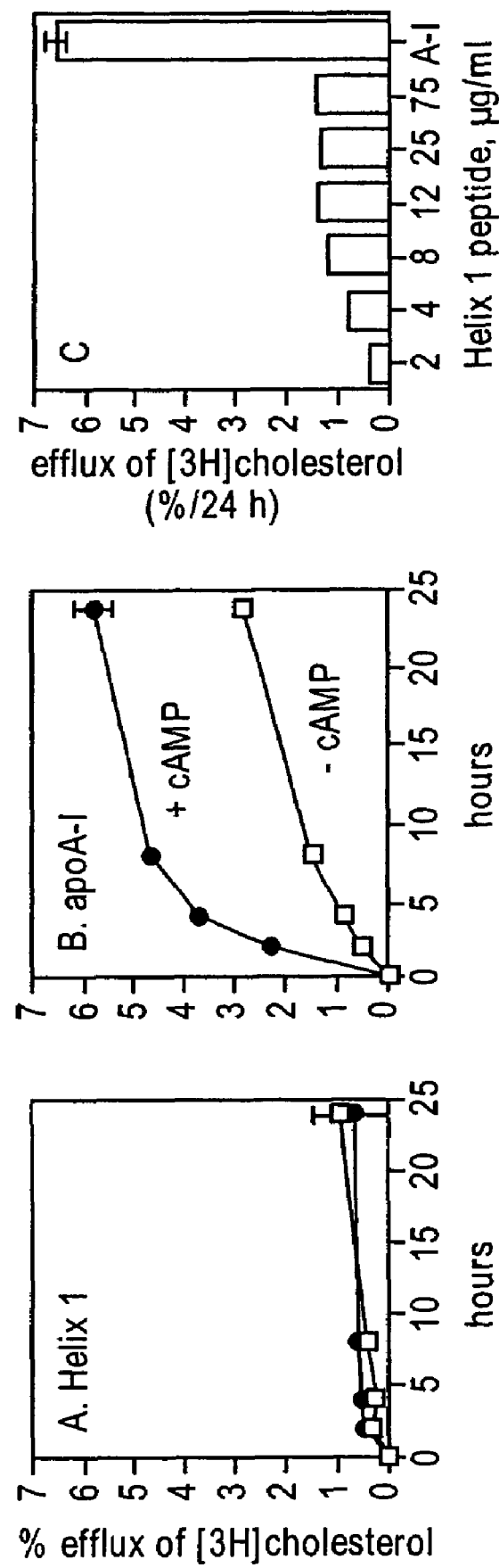

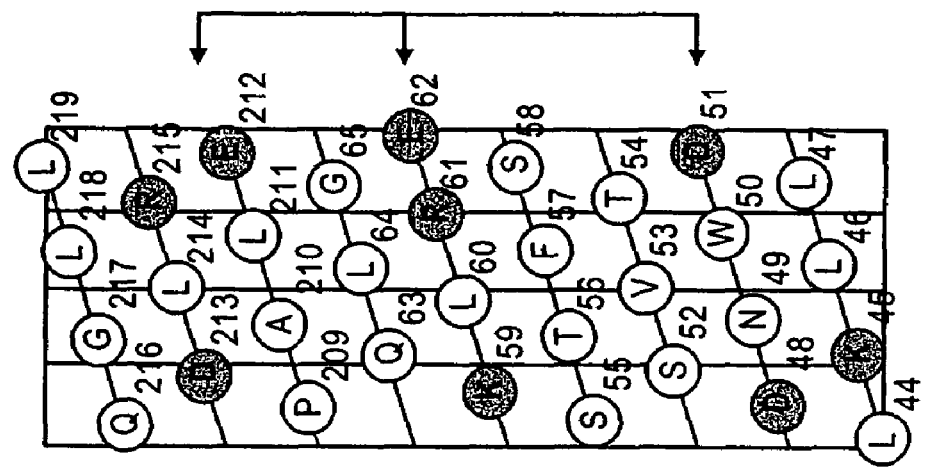
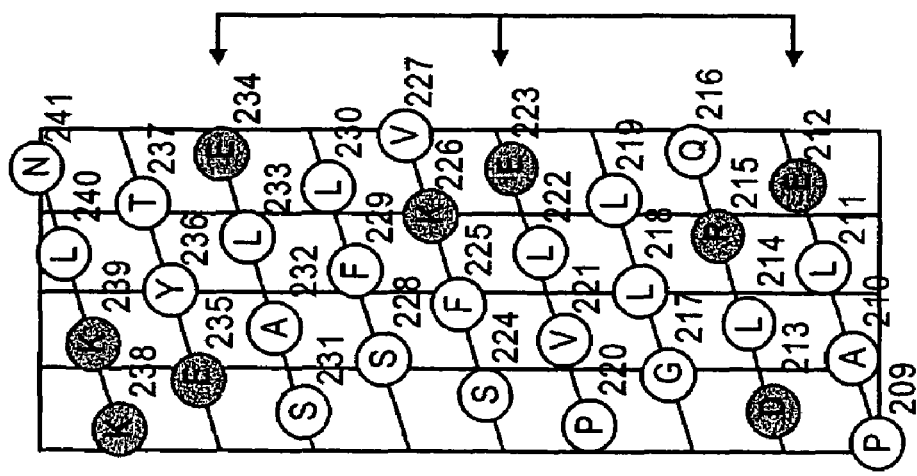
FIG. 4B

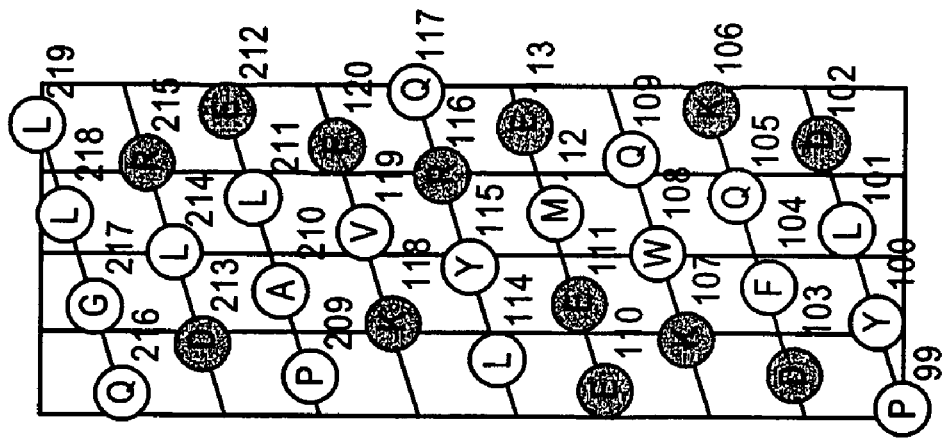
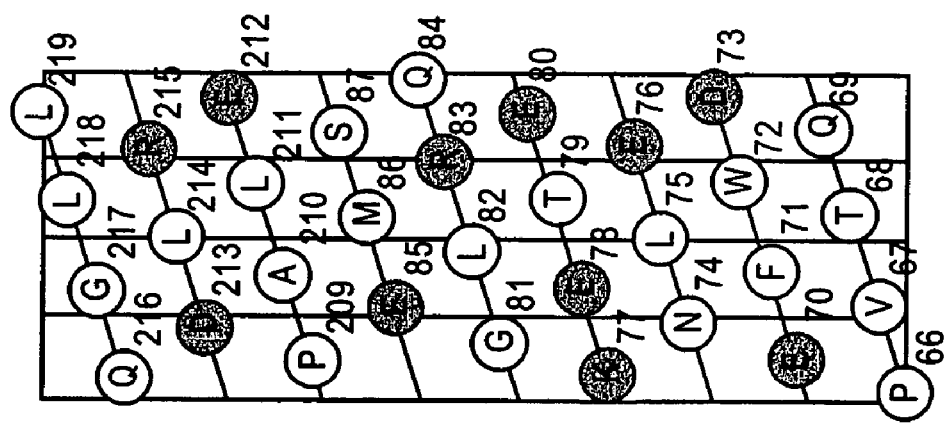
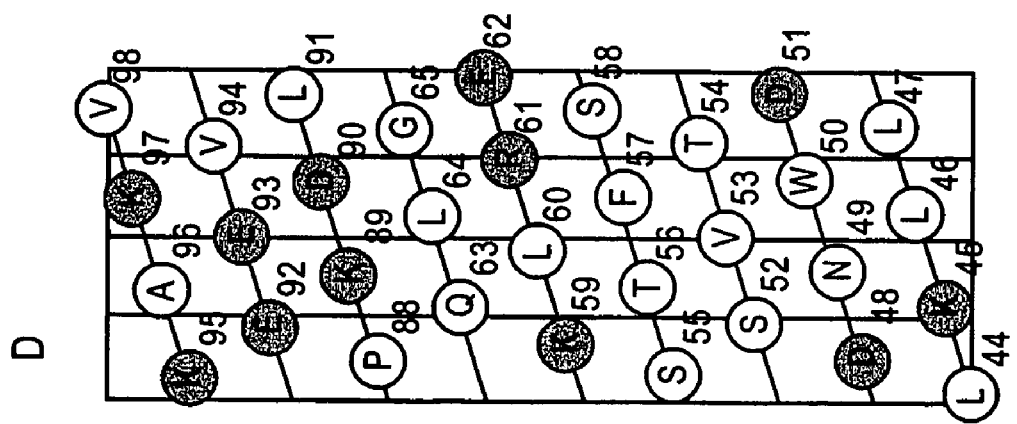
FIG. 5D

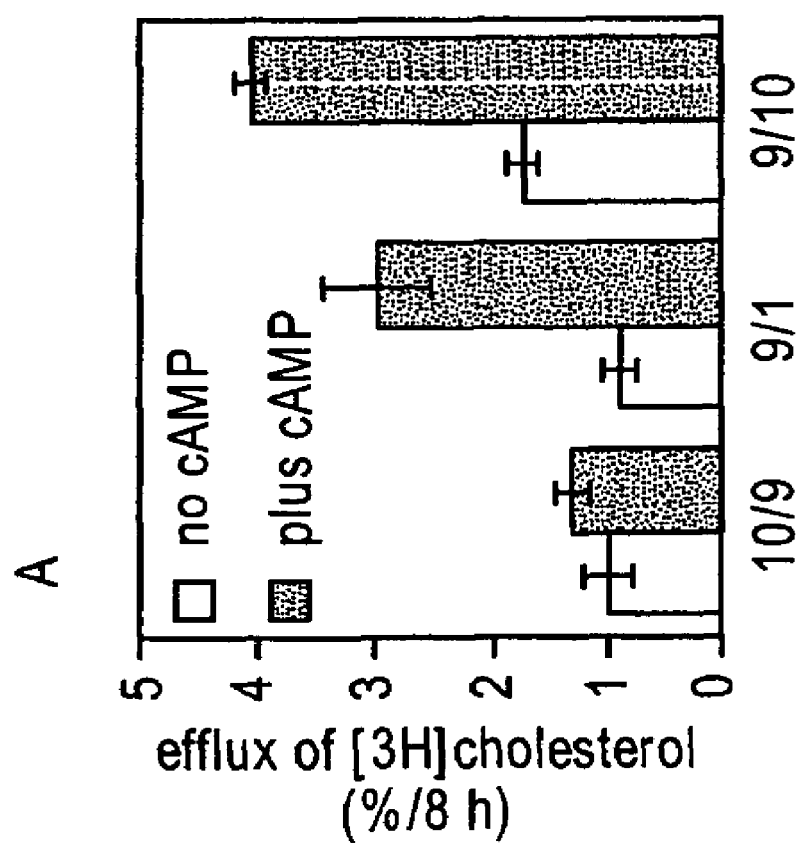
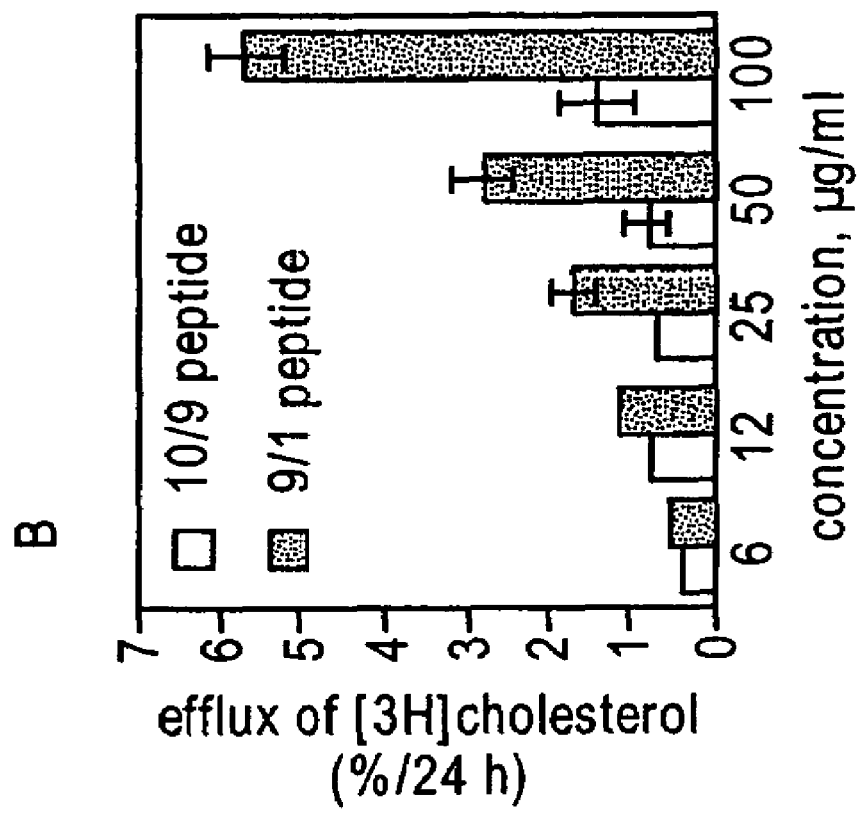
FIG. 6A
FIG. 6B

D

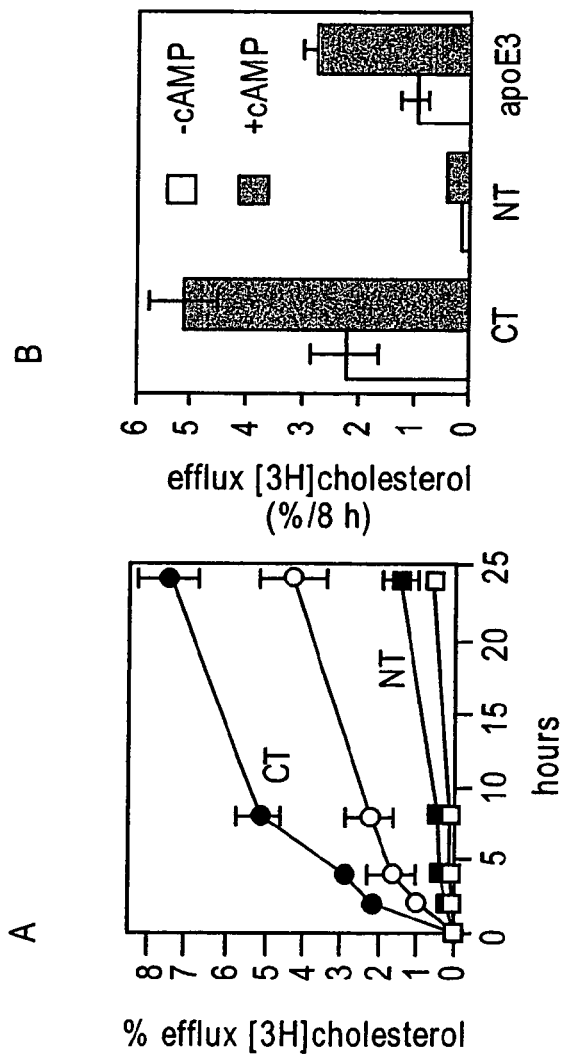
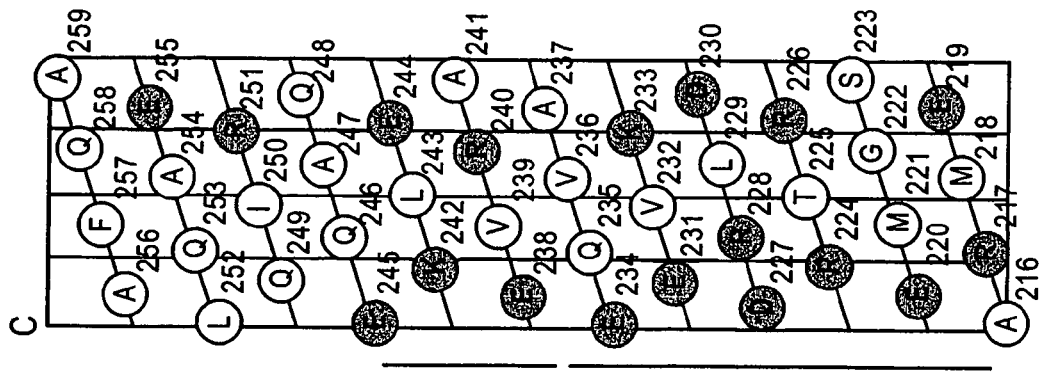
FIG. 8A
FIG. 8B
FIG. 8C

```
                        SEQUENCE LISTING

<160> NUMBER OF SEQ ID NOS: 51

<210> SEQ ID NO 1
<211> LENGTH: 33
<212> TYPE: PRT
<213> ORGANISM: Artificial Sequence
<220> FEATURE:
<223> OTHER INFORMATION: Helix 9 and 10 of apolipoprotein Apo A-I
      modified, Apo A-I Helix 9/10 modified, helix 9/10 of Apo I
      with Cys residue at polar/nonpolar interface,
      Cysteine(thiol)-containing Apo AI 9/10

<400> SEQUENCE: 1

Pro Ala Leu Glu Asp Leu Arg Gln Gly Leu Leu Pro Val Leu Glu Ser
1               5                   10                  15

Phe Cys Val Lys Phe Leu Ser Ala Leu Glu Glu Tyr Thr Lys Lys Leu
            20                  25                  30

Asn

<210> SEQ ID NO 2
<211> LENGTH: 26
<212> TYPE: PRT
<213> ORGANISM: Artificial Sequence
<220> FEATURE:
<223> OTHER INFORMATION: Helix 10 of apolipoprotein Apo A-I modified,
      Helix 10 (aa220-241) of Apo A-I with additional acidic
      residue

<400> SEQUENCE: 2

Pro Val Leu Glu Ser Phe Lys Val Ser Phe Leu Ser Ala Leu Glu Glu
1               5                   10                  15

Tyr Lys Thr Lys Leu Glu Ser Ala Leu Asn
            20                  25

<210> SEQ ID NO 3
<211> LENGTH: 33
<212> TYPE: PRT
<213> ORGANISM: Artificial Sequence
<220> FEATURE:
<223> OTHER INFORMATION: apolipoprotein Apo C-III, residues 37-69

<400> SEQUENCE: 3

Gln Gln Ala Arg Gly Trp Val Thr Asp Gly Phe Ser Ser Leu Lys Asp
1               5                   10                  15

Tyr Trp Ser Thr Val Lys Asp Lys Phe Ser Glu Phe Trp Asp Leu Asp
            20                  25                  30

Pro

<210> SEQ ID NO 4
<211> LENGTH: 84
<212> TYPE: PRT
<213> ORGANISM: Artificial Sequence
<220> FEATURE:
<223> OTHER INFORMATION: apolipoprotein Apo E, C-terminal domain
      (aa216-299)

<400> SEQUENCE: 4

Ala Arg Met Glu Glu Met Gly Ser Arg Thr Arg Asp Arg Leu Asp Glu
```

-continued

```
                1               5                  10                  15
Val Lys Glu Gln Val Ala Glu Val Arg Ala Lys Leu Glu Glu Gln Ala
                    20                  25                  30
Gln Gln Ile Arg Leu Gln Ala Glu Ala Phe Gln Ala Arg Leu Lys Ser
            35                  40                  45
Trp Phe Glu Pro Leu Val Glu Asp Met Gln Arg Gln Trp Ala Gly Leu
        50                  55                  60
Val Glu Lys Val Gln Ala Ala Val Gly Thr Ser Ala Ala Pro Val Pro
65                  70                  75                  80
Ser Asp Asn His

<210> SEQ ID NO 5
<211> LENGTH: 33
<212> TYPE: PRT
<213> ORGANISM: Artificial Sequence
<220> FEATURE:
<223> OTHER INFORMATION: apolipoprotein Apo E (aa216-248)

<400> SEQUENCE: 5

Ala Arg Met Glu Glu Met Gly Ser Arg Thr Arg Asp Arg Leu Asp Glu
1               5                   10                  15
Val Lys Glu Gln Val Ala Glu Val Arg Ala Lys Leu Glu Glu Gln Ala
            20                  25                  30
Gln

<210> SEQ ID NO 6
<211> LENGTH: 22
<212> TYPE: PRT
<213> ORGANISM: Artificial Sequence
<220> FEATURE:
<223> OTHER INFORMATION: apolipoprotein Apo E (aa216-237)

<400> SEQUENCE: 6

Ala Arg Met Glu Glu Met Gly Ser Arg Thr Arg Asp Arg Leu Asp Glu
1               5                   10                  15
Val Lys Glu Gln Val Ala
            20

<210> SEQ ID NO 7
<211> LENGTH: 33
<212> TYPE: PRT
<213> ORGANISM: Artificial Sequence
<220> FEATURE:
<223> OTHER INFORMATION: apolipoprotein Apo E (aa238-266)

<400> SEQUENCE: 7

Glu Val Arg Ala Lys Leu Glu Glu Gln Ala Gln Ile Arg Leu Gln
1               5                   10                  15
Ala Glu Ala Phe Gln Ala Arg Leu Lys Ser Trp Phe Glu Pro Val Leu
            20                  25                  30
Glu

<210> SEQ ID NO 8
<211> LENGTH: 33
<212> TYPE: PRT
<213> ORGANISM: Artificial Sequence
<220> FEATURE:
<223> OTHER INFORMATION: apolipoprotein Apo E (aa267-299)

<400> SEQUENCE: 8

Pro Leu Val Glu Asp Met Gln Arg Gln Trp Ala Gly Leu Val Glu Lys
```

```
                        1               5                  10                 15
Val Gln Ala Ala Val Gly Thr Ser Ala Ala Pro Val Pro Ser Asp Asn
                        20                 25                 30

His

<210> SEQ ID NO 9
<211> LENGTH: 26
<212> TYPE: PRT
<213> ORGANISM: Artificial Sequence
<220> FEATURE:
<223> OTHER INFORMATION: apolipoprotein Apo E, C- terminus (aa238-263)
      modified for alignment of acidic residues on polar
      surface

<400> SEQUENCE: 9

Glu Val Arg Ala Lys Leu Glu Glu Trp Phe Gln Gln Ile Arg Leu Gln
 1               5                  10                 15

Ala Glu Glu Phe Gln Ala Arg Leu Lys Ser
            20                  25

<210> SEQ ID NO 10
<211> LENGTH: 33
<212> TYPE: PRT
<213> ORGANISM: Artificial Sequence
<220> FEATURE:
<223> OTHER INFORMATION: apolipoprotein Apo A-IV (aa62-94), ApoA-IV
      62-94

<400> SEQUENCE: 10

Pro Phe Ala Thr Glu Leu His Glu Arg Leu Ala Lys Asp Ser Glu Lys
 1               5                  10                 15

Leu Lys Glu Glu Ile Gly Lys Glu Leu Glu Glu Leu Arg Ala Arg Leu
            20                  25                 30

Leu

<210> SEQ ID NO 11
<211> LENGTH: 25
<212> TYPE: PRT
<213> ORGANISM: Artificial Sequence
<220> FEATURE:
<223> OTHER INFORMATION: apolipoprotein Apo A-IV (aa66-90)

<400> SEQUENCE: 11

Glu Leu His Glu Arg Leu Ala Lys Asp Ser Glu Lys Leu Lys Glu Glu
 1               5                  10                 15

Ile Gly Lys Glu Leu Glu Glu Leu Arg
            20                  25

<210> SEQ ID NO 12
<211> LENGTH: 44
<212> TYPE: PRT
<213> ORGANISM: Artificial Sequence
<220> FEATURE:
<223> OTHER INFORMATION: apolipoprotein Apo A-IV (aa161-204), ApoA-IV
      161-204

<400> SEQUENCE: 12

Pro His Ala Asp Glu Leu Lys Ala Lys Ile Asp Gln Asn Val Glu Glu
 1               5                  10                 15

Leu Lys Gly Arg Leu Thr Pro Tyr Ala Asp Glu Phe Lys Val Lys Ile
            20                  25                 30

Asp Gln Thr Val Glu Glu Leu Arg Arg Ser Leu Ala
            35                  40
```

<210> SEQ ID NO 13
<211> LENGTH: 22
<212> TYPE: PRT
<213> ORGANISM: Artificial Sequence
<220> FEATURE:
<223> OTHER INFORMATION: apolipoprotein Apo A-IV (aa161-182)

<400> SEQUENCE: 13

```
Pro His Ala Asp Glu Leu Lys Ala Lys Ile Asp Gln Asn Val Glu Glu
1               5                   10                  15

Leu Lys Gly Arg Leu Thr
            20
```

<210> SEQ ID NO 14
<211> LENGTH: 22
<212> TYPE: PRT
<213> ORGANISM: Artificial Sequence
<220> FEATURE:
<223> OTHER INFORMATION: apolipoprotein Apo A-IV (aa183-204)

<400> SEQUENCE: 14

```
Pro Tyr Ala Asp Glu Phe Lys Val Lys Ile Asp Gln Thr Val Glu Glu
1               5                   10                  15

Leu Arg Arg Ser Leu Ala
            20
```

<210> SEQ ID NO 15
<211> LENGTH: 44
<212> TYPE: PRT
<213> ORGANISM: Artificial Sequence
<220> FEATURE:
<223> OTHER INFORMATION: apolipoprotein Apo A-IV (aa183-226), ApoA-IV
      183-226

<400> SEQUENCE: 15

```
Pro Tyr Ala Asp Glu Phe Lys Val Lys Ile Asp Gln Thr Val Glu Glu
1               5                   10                  15

Leu Arg Arg Ser Leu Ala Pro Tyr Ala Gln Asp Thr Gln Glu Lys Leu
            20                  25                  30

Asn His Gln Leu Glu Gly Leu Thr Phe Gln Met Lys
        35                  40
```

<210> SEQ ID NO 16
<211> LENGTH: 22
<212> TYPE: PRT
<213> ORGANISM: Artificial Sequence
<220> FEATURE:
<223> OTHER INFORMATION: apolipoprotein Apo A-IV (aa205-226)

<400> SEQUENCE: 16

```
Pro Tyr Ala Gln Asp Thr Gln Glu Lys Leu Asn His Gln Leu Glu Gly
1               5                   10                  15

Leu Thr Phe Gln Met Lys
            20
```

<210> SEQ ID NO 17
<211> LENGTH: 44
<212> TYPE: PRT
<213> ORGANISM: Artificial Sequence
<220> FEATURE:
<223> OTHER INFORMATION: apolipoprotein Apo A-IV (aa205-248), ApoA-IV
      205-248

<400> SEQUENCE: 17

```
Pro Tyr Ala Gln Asp Thr Gln Glu Lys Leu Asn His Gln Leu Glu Gly
 1               5                  10                  15

Leu Thr Phe Gln Met Lys Lys Asn Ala Glu Glu Leu Lys Ala Arg Ile
            20                  25                  30

Ser Ala Ser Ala Glu Glu Leu Arg Gln Arg Leu Ala
        35                  40

<210> SEQ ID NO 18
<211> LENGTH: 22
<212> TYPE: PRT
<213> ORGANISM: Artificial Sequence
<220> FEATURE:
<223> OTHER INFORMATION: apolipoprotein Apo A-IV (aa227-248)

<400> SEQUENCE: 18

Lys Asn Ala Glu Glu Leu Lys Ala Arg Ile Ser Ala Ser Ala Glu Glu
 1               5                  10                  15

Leu Arg Gln Arg Leu Ala
            20

<210> SEQ ID NO 19
<211> LENGTH: 22
<212> TYPE: PRT
<213> ORGANISM: Artificial Sequence
<220> FEATURE:
<223> OTHER INFORMATION: apolipoprotein Apo A-IV (aa117-138)

<400> SEQUENCE: 19

Pro Tyr Ala Asp Gln Leu Arg Thr Gln Val Asn Thr Gln Ala Glu Gln
 1               5                  10                  15

Leu Arg Arg Gln Leu Thr
            20

<210> SEQ ID NO 20
<211> LENGTH: 22
<212> TYPE: PRT
<213> ORGANISM: Artificial Sequence
<220> FEATURE:
<223> OTHER INFORMATION: apolipoprotein Apo A-IV (aa138-160)

<400> SEQUENCE: 20

Pro Leu Ala Gln Arg Met Glu Arg Val Leu Arg Glu Asn Ala Asp Ser
 1               5                  10                  15

Leu Gln Ala Ser Leu Arg
            20

<210> SEQ ID NO 21
<211> LENGTH: 33
<212> TYPE: PRT
<213> ORGANISM: Artificial Sequence
<220> FEATURE:
<223> OTHER INFORMATION: apolipoprotein Apo C-I (aa25-57), ApoCI 25-57

<400> SEQUENCE: 21

Leu Ile Ser Arg Ile Lys Gln Ser Glu Leu Ser Ala Lys Met Arg Glu
 1               5                  10                  15

Trp Phe Ser Glu Thr Phe Gln Lys Val Lys Glu Lys Leu Lys Ile Asp
            20                  25                  30

Ser

<210> SEQ ID NO 22
<211> LENGTH: 22
```

```
<212> TYPE: PRT
<213> ORGANISM: Artificial Sequence
<220> FEATURE:
<223> OTHER INFORMATION: apolipoprotein Apo C-I (aa6-27)

<400> SEQUENCE: 22

Ser Ala Leu Asp Lys Leu Lys Glu Phe Gly Asn Thr Leu Glu Asp Lys
1               5                   10                  15

Ala Arg Glu Leu Ile Ser
            20

<210> SEQ ID NO 23
<211> LENGTH: 25
<212> TYPE: PRT
<213> ORGANISM: Artificial Sequence
<220> FEATURE:
<223> OTHER INFORMATION: apolipoprotein Apo C-I (aa29-53)

<400> SEQUENCE: 23

Ile Lys Gln Ser Glu Leu Ser Ala Lys Met Arg Glu Trp Phe Ser Glu
1               5                   10                  15

Thr Phe Gln Lys Val Lys Glu Lys Leu
            20                  25

<210> SEQ ID NO 24
<211> LENGTH: 31
<212> TYPE: PRT
<213> ORGANISM: Artificial Sequence
<220> FEATURE:
<223> OTHER INFORMATION: apolipoprotein Apo C-II (aa12-42), ApoCII 12-42

<400> SEQUENCE: 24

Pro Thr Phe Leu Thr Gln Val Lys Glu Ser Leu Ser Ser Tyr Trp Glu
1               5                   10                  15

Ser Ala Lys Thr Ala Ala Gln Asn Leu Tyr Glu Lys Thr Tyr Leu
            20                  25                  30

<210> SEQ ID NO 25
<211> LENGTH: 25
<212> TYPE: PRT
<213> ORGANISM: Artificial Sequence
<220> FEATURE:
<223> OTHER INFORMATION: apolipoprotein Apo C-II (aa16-40)

<400> SEQUENCE: 25

Thr Gln Val Lys Glu Ser Leu Ser Ser Tyr Trp Glu Ser Ala Lys Thr
1               5                   10                  15

Ala Ala Gln Asn Leu Tyr Glu Lys Thr
            20                  25

<210> SEQ ID NO 26
<211> LENGTH: 26
<212> TYPE: PRT
<213> ORGANISM: Artificial Sequence
<220> FEATURE:
<223> OTHER INFORMATION: apolipoprotein Apo C-II (aa43-68)

<400> SEQUENCE: 26

Pro Ala Val Asp Glu Lys Leu Arg Asp Leu Tyr Ser Lys Ser Thr Ala
1               5                   10                  15

Ala Met Ser Thr Tyr Thr Gly Ile Phe Thr
            20                  25

<210> SEQ ID NO 27
```

-continued

<210> SEQ ID NO 27
<211> LENGTH: 33
<212> TYPE: PRT
<213> ORGANISM: Artificial Sequence
<220> FEATURE:
<223> OTHER INFORMATION: apolipoprotein Apo C-III (aa37-69)

<400> SEQUENCE: 27

Gln Gln Ala Arg Gly Trp Val Thr Asp Gly Phe Ser Ser Leu Lys Asp
1               5                   10                  15

Tyr Trp Ser Thr Val Lys Asp Lys Phe Ser Glu Phe Trp Asp Leu Asp
            20                  25                  30

Pro

<210> SEQ ID NO 28
<211> LENGTH: 25
<212> TYPE: PRT
<213> ORGANISM: Artificial Sequence
<220> FEATURE:
<223> OTHER INFORMATION: apolipoprotein Apo C-III (aa45-69)

<400> SEQUENCE: 28

Asp Gly Phe Ser Ser Leu Lys Asp Tyr Trp Ser Thr Val Lys Asp Lys
1               5                   10                  15

Phe Ser Glu Phe Trp Asp Leu Asp Pro
            20                  25

<210> SEQ ID NO 29
<211> LENGTH: 51
<212> TYPE: PRT
<213> ORGANISM: Artificial Sequence
<220> FEATURE:
<223> OTHER INFORMATION: apolipoprotein Apo A-II (aa1-51)

<400> SEQUENCE: 29

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro
    50

<210> SEQ ID NO 30
<211> LENGTH: 28
<212> TYPE: PRT
<213> ORGANISM: Artificial Sequence
<220> FEATURE:
<223> OTHER INFORMATION: apolipoprotein Apo A-II (aa5-32)

<400> SEQUENCE: 30

Pro Cys Val Glu Ser Leu Val Ser Gln Tyr Phe Gln Thr Val Thr Asp
1               5                   10                  15

Tyr Gly Lys Asp Leu Met Glu Lys Val Lys Ser Pro
            20                  25

<210> SEQ ID NO 31
<211> LENGTH: 36
<212> TYPE: PRT
<213> ORGANISM: Artificial Sequence
<220> FEATURE:
<223> OTHER INFORMATION: serum amyloid A (SAA) (aa1-36)

<400> SEQUENCE: 31

```
Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe
        35
```

```
<210> SEQ ID NO 32
<211> LENGTH: 34
<212> TYPE: PRT
<213> ORGANISM: Artificial Sequence
<220> FEATURE:
<223> OTHER INFORMATION: serum amyloid A (SAA) (aa1-34)

<400> SEQUENCE: 32

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys
```

```
<210> SEQ ID NO 33
<211> LENGTH: 26
<212> TYPE: PRT
<213> ORGANISM: Artificial Sequence
<220> FEATURE:
<223> OTHER INFORMATION: serum amyloid A (SAA) (aa5-29)

<400> SEQUENCE: 33

Ser Phe Leu Gly Glu Ala Glu Phe Asp Gly Ala Arg Asp Met Trp Arg
1               5                   10                  15

Ala Tyr Ser Asp Met Arg Glu Ala Asn Tyr
            20                  25
```

```
<210> SEQ ID NO 34
<211> LENGTH: 26
<212> TYPE: PRT
<213> ORGANISM: Artificial Sequence
<220> FEATURE:
<223> OTHER INFORMATION: serum amyloid A (SAA) (aa53-78)

<400> SEQUENCE: 34

Trp Ala Ala Glu Val Ile Ser Asn Ala Arg Glu Asn Ile Gln Arg Leu
1               5                   10                  15

Thr Gly His Gly Ala Glu Asp Ser Leu Ala
            20                  25
```

```
<210> SEQ ID NO 35
<211> LENGTH: 33
<212> TYPE: PRT
<213> ORGANISM: Artificial Sequence
<220> FEATURE:
<223> OTHER INFORMATION: apolipoprotein Apo A-I Helix 9 and 10 joined a
      Pro residue, 9/10 helical peptide, ApoA-I Helices 9
      and 10

<400> SEQUENCE: 35

Pro Ala Leu Glu Asp Leu Arg Gln Gly Leu Leu Pro Val Leu Glu Ser
1               5                   10                  15

Phe Lys Val Ser Phe Leu Ser Ala Leu Glu Glu Tyr Thr Lys Lys Leu
            20                  25                  30

Asn
```

```
<210> SEQ ID NO 36
<211> LENGTH: 33
<212> TYPE: PRT
<213> ORGANISM: Artificial Sequence
<220> FEATURE:
<223> OTHER INFORMATION: apolipoprotein Apo A-I Helix 1 and 2 joined by
      a Pro residue, ApoA-I Helices 1 and 2

<400> SEQUENCE: 36

Leu Lys Leu Leu Asp Asn Trp Asp Ser Val Thr Ser Thr Phe Ser Lys
1               5                   10                  15

Leu Arg Glu Gln Leu Gly Pro Ala Leu Glu Asp Leu Arg Gln Gly Leu
            20                  25                  30

Leu

<210> SEQ ID NO 37
<211> LENGTH: 44
<212> TYPE: PRT
<213> ORGANISM: Artificial Sequence
<220> FEATURE:
<223> OTHER INFORMATION: apolipoprotein Apo A-I Helix 1 and 9 joined by
      Pro residue, ApoA-I Helices 1 and 9

<400> SEQUENCE: 37

Ala Arg Leu Ala Glu Tyr His Ala Lys Ala Thr Glu His Leu Ser Thr
1               5                   10                  15

Leu Ser Glu Lys Ala Lys Pro Val Leu Glu Ser Phe Lys Val Ser Phe
            20                  25                  30

Leu Ser Ala Leu Glu Glu Tyr Thr Lys Lys Leu Asn
        35                  40

<210> SEQ ID NO 38
<211> LENGTH: 44
<212> TYPE: PRT
<213> ORGANISM: Artificial Sequence
<220> FEATURE:
<223> OTHER INFORMATION: apolipoprotein Apo A-I Helix 8 and 10 joined by
      a Pro residue, ApoA-I Helices 8 and 10

<400> SEQUENCE: 38

Pro Tyr Ser Asp Glu Leu Arg Gln Arg Leu Ala Ala Arg Leu Glu Ala
1               5                   10                  15

Leu Lys Glu Asn Gly Gly Pro Val Leu Glu Ser Phe Lys Val Ser Phe
            20                  25                  30

Leu Ser Ala Leu Glu Glu Tyr Thr Lys Lys Leu Asn
        35                  40

<210> SEQ ID NO 39
<211> LENGTH: 44
<212> TYPE: PRT
<213> ORGANISM: Artificial Sequence
<220> FEATURE:
<223> OTHER INFORMATION: apolipoprotein Apo A-I Helix 7 and 10 joined by
      a Pro residue, ApoA-I Helices 7 and 10

<400> SEQUENCE: 39

Pro Leu Gly Glu Glu Met Arg Asp Arg Ala Arg Ala His Val Asp Ala
1               5                   10                  15

Leu Arg Thr His Leu Ala Pro Val Leu Glu Ser Phe Lys Val Ser Phe
            20                  25                  30

Leu Ser Ala Leu Glu Glu Tyr Thr Lys Lys Leu Asn
        35                  40
```

```
<210> SEQ ID NO 40
<211> LENGTH: 33
<212> TYPE: PRT
<213> ORGANISM: Artificial Sequence
<220> FEATURE:
<223> OTHER INFORMATION: apolipoprotein Apo A-I Helix 6 and 10 jouned by
      a Pro residue, ApoA-I Helices 6 and 10

<400> SEQUENCE: 40

Pro Ala Leu Glu Asp Leu Arg Gln Gly Leu Leu Lys Leu Leu Asp
1               5                   10                  15

Asn Trp Asp Ser Val Thr Ser Thr Phe Ser Lys Leu Arg Glu Gln Leu
            20                  25                  30

Gly

<210> SEQ ID NO 41
<211> LENGTH: 44
<212> TYPE: PRT
<213> ORGANISM: Artificial Sequence
<220> FEATURE:
<223> OTHER INFORMATION: apolipoprotein Apo A-I Helix 9 and 1, ApoA-I
      Helices 9 and 1, ApoA1 chimeric sequence, Apo A-I
      alpha-helical transposition peptide 9/1

<400> SEQUENCE: 41

Leu Lys Leu Leu Asp Asn Trp Asp Ser Val Thr Ser Thr Phe Ser Lys
1               5                   10                  15

Leu Arg Glu Gln Leu Gly Pro Val Thr Gln Glu Phe Trp Asp Asn Leu
            20                  25                  30

Glu Lys Glu Thr Glu Gly Leu Arg Gln Glu Met Ser
        35                  40

<210> SEQ ID NO 42
<211> LENGTH: 33
<212> TYPE: PRT
<213> ORGANISM: Artificial Sequence
<220> FEATURE:
<223> OTHER INFORMATION: apolipoprotein Apo A-I amphipathic
      alpha-helical chimeric peptide 1/3

<400> SEQUENCE: 42

Leu Lys Leu Leu Asp Asn Trp Asp Ser Val Thr Ser Thr Phe Ser Lys
1               5                   10                  15

Leu Arg Glu Gln Leu Gly Pro Lys Asp Leu Glu Glu Val Lys Ala Lys
            20                  25                  30

Val

<210> SEQ ID NO 43
<211> LENGTH: 33
<212> TYPE: PRT
<213> ORGANISM: Artificial Sequence
<220> FEATURE:
<223> OTHER INFORMATION: apolipoprotein Apo A-I amphipathic
      alpha-helical chimeric peptide 2/9

<400> SEQUENCE: 43

Pro Val Thr Gln Glu Phe Trp Asp Asn Leu Glu Lys Glu Thr Glu Gly
1               5                   10                  15

Leu Arg Gln Glu Met Ser Pro Ala Leu Glu Asp Leu Arg Gln Gly Leu
            20                  25                  30

Leu
```

```
<210> SEQ ID NO 44
<211> LENGTH: 33
<212> TYPE: PRT
<213> ORGANISM: Artificial Sequence
<220> FEATURE:
<223> OTHER INFORMATION: apolipoprotein Apo A-I amphipathic
      alpha-helical chimeric peptide 4/9

<400> SEQUENCE: 44

Pro Tyr Leu Asp Asp Phe Gln Lys Lys Trp Gln Glu Glu Met Glu Leu
1               5                   10                  15

Tyr Arg Gln Lys Val Glu Pro Ala Leu Glu Asp Leu Arg Gln Gly Leu
            20                  25                  30

Leu

<210> SEQ ID NO 45
<211> LENGTH: 33
<212> TYPE: PRT
<213> ORGANISM: Artificial Sequence
<220> FEATURE:
<223> OTHER INFORMATION: apolipoprotein Apo A-I alpha-helical
      transposition peptide 10/9

<400> SEQUENCE: 45

Pro Val Leu Glu Ser Phe Lys Val Ser Phe Leu Ser Ala Leu Glu Glu
1               5                   10                  15

Tyr Thr Lys Lys Leu Asn Pro Ala Leu Glu Asp Leu Arg Gln Gly Leu
            20                  25                  30

Leu

<210> SEQ ID NO 46
<211> LENGTH: 33
<212> TYPE: PRT
<213> ORGANISM: Artificial Sequence
<220> FEATURE:
<223> OTHER INFORMATION: apolipoprotein Apo A-I alpha-helical
      transposition peptide 9/1 with Pro in place of Leu 44 of
      full-length Apo A-I

<400> SEQUENCE: 46

Pro Ala Leu Glu Asp Leu Arg Gln Gly Leu Leu Pro Lys Leu Leu Asp
1               5                   10                  15

Asn Trp Asp Ser Val Thr Ser Thr Phe Ser Lys Leu Arg Glu Gln Leu
            20                  25                  30

Gly

<210> SEQ ID NO 47
<211> LENGTH: 44
<212> TYPE: PRT
<213> ORGANISM: Artificial Sequence
<220> FEATURE:
<223> OTHER INFORMATION: apolipoprotein Apo A-I helices 6 and 7

<400> SEQUENCE: 47

Pro Leu Gly Glu Glu Met Arg Asp Arg Ala Arg Ala His Val Asp Ala
1               5                   10                  15

Leu Arg Thr His Leu Ala Pro Tyr Ser Asp Glu Leu Arg Gln Arg Leu
            20                  25                  30

Ala Ala Arg Leu Glu Ala Leu Lys Glu Asn Gly Gly
        35                  40

<210> SEQ ID NO 48
```

```
<211> LENGTH: 44
<212> TYPE: PRT
<213> ORGANISM: Artificial Sequence
<220> FEATURE:
<223> OTHER INFORMATION: helical first 44 amino acids of C-terminal
      domain of apolipoprotein Apo E

<400> SEQUENCE: 48

Ala Arg Met Glu Glu Met Gly Ser Arg Thr Arg Asp Arg Leu Asp Glu
 1               5                  10                  15

Val Lys Glu Gln Val Ala Glu Val Arg Ala Lys Leu Glu Glu Gln Ala
             20                  25                  30

Gln Gln Ile Arg Leu Gln Ala Glu Ala Phe Gln Ala
         35                  40

<210> SEQ ID NO 49
<211> LENGTH: 11
<212> TYPE: PRT
<213> ORGANISM: Artificial Sequence
<220> FEATURE:
<223> OTHER INFORMATION: modified Factor Xa cleavage site to facilitate
      removal of His-tag

<400> SEQUENCE: 49

Met His His His His His His Ile Glu Gly Arg
 1               5                  10

<210> SEQ ID NO 50
<211> LENGTH: 18
<212> TYPE: PRT
<213> ORGANISM: Artificial Sequence
<220> FEATURE:
<223> OTHER INFORMATION: modified 18A(4F) peptide

<400> SEQUENCE: 50

Asp Trp Leu Lys Ala Phe Tyr Asp Lys Val Phe Glu Lys Phe Lys Glu
 1               5                  10                  15

Ala Phe

<210> SEQ ID NO 51
<211> LENGTH: 51
<212> TYPE: PRT
<213> ORGANISM: Artificial Sequence
<220> FEATURE:
<223> OTHER INFORMATION: apolipoprotein Apo E 216-267

<400> SEQUENCE: 51

Ala Arg Met Glu Glu Met Gly Ser Arg Thr Arg Asp Arg Leu Asp Glu
 1               5                  10                  15

Val Lys Glu Gln Val Ala Glu Val Arg Ala Lys Leu Glu Glu Gln Ala
             20                  25                  30

Gln Gln Ile Arg Leu Gln Ala Glu Ala Phe Gln Ala Arg Leu Lys Ser
         35                  40                  45

Trp Phe Glu
     50
```

HELICAL SYNTHETIC PEPTIDES THAT STIMULATE CELLULAR CHOLESTEROL EFFLUX

CROSS-REFERENCES TO RELATED APPLICATIONS

This application is a continuation in part of U.S. patent application Ser. No. 10/142,238, filed May 8, 2002 and claims the benefit of U.S. Provisional Patent Application No. 60/529,933, filed Dec. 15, 2003, the disclosures of which are herein incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. HL59483 awarded by the NIH/NCI to J. K. Bielicki and U.S. Department of Energy Contract No. DE-AC03-76SF00098. The Government has certain rights in this invention.

BACKGROUND OF THE INVENTION

Cardiovascular disease affects millions of people per year. One aspect of cardiovascular disease is hyperlipidemia, a condition which is characterized by an abnormal increase in serum lipids, such as cholesterol, triglycerides and phospholipids. One form of hyperlipidemia is hypercholesterolemia, characterized by the existence of elevated LDL cholesterol levels. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., *Am. I. Med.*, 62:707-714 (1977); Stampfer, et al., *N. England J. Med.*, 325:373-381 (1991); and Kannel, et al., *Ann. Internal Med.*, 90:85-91 (1979).

Plasma HDL-cholesterol concentrations are inversely related to atherosclerosis (see, e.g., Gordon et al., *Am. J. Med.* 62:707-714 (1977) and Rifkind, *Am. J. Cardiol.* 66:3A-6A (1990)). The beneficial effects of HDL are attributed, in part, to its role in reverse cholesterol transport (RCT), an important anti-atherogenic pathway. The rate-limiting, first-step of RCT involves the efflux of cholesterol from macrophage foam-cells in the artery wall mediated by apoA-I, the major HDL apolipoprotein (see, e.g., Rothblat and Phillips, *Curr. Opin. Lipidol.* 2:288-294 (1991) and Fielding and Fielding, *J. Lipid Res.* 36:211-228 (1995)). Cholesterol efflux mediated by apoA-I generates nascent HDL and reverses the macrophage foam-cell phenotype. For these reasons, cellular cholesterol efflux is clinically relevant representing an attractive target of therapeutic interventions for combating atherosclerosis. Recently a synthetic form of HDL was found to rapidly regress atherosclerotic lesions in humans suffering from acute coronary syndrome, providing evidence that therapeutics based on HDL may be efficacious in the treatment of heart disease (Nissen et al., *JAMA* 290:2292-2300 (2003)). Developing the next generation of advanced therapeutics based on HDL requires detailed knowledge of the underlying molecular mechanisms by which apoA-I stimulates cellular cholesterol efflux and initiates RCT.

Mutations in the ATP-binding cassette transporter A1 (ABCA1) as found in Tangier Disease abolish the ability of apoA-I to promote cellular cholesterol efflux (see, e.g., Francis et al., *J. Clin. Invest.* 96: 78-87 (1995); Remaley et al., *Arterioscler. Thromb. Vasc. Biol.* 17:1813-1821 (1997); Brooks-Wilson et al., *Nature Genetics*, 22:336-344 (1999); and Bodzioch et al., *Nature Genetics*, 22:347-351 (1999)). Human subjects with Tangier Disease have increased risk for developing premature atherosclerosis resulting from a deficiency in HDL (see, e.g., Brooks-Wilson et al., *Nature Genetics*, 22:336-344 (1999); Bodzioch et al., *Nature Genetics*, 22:347-351 (1999); Schaefer et al., *Ann. Intern. Med.* 93:261-266 (1983); Serfaty-Lacrosniere et al., *Atherosclerosis* 107: 85-98 (1994); and Hobbs and Rader, *J. Clin. Invest.* 104: 1015-1017 (1999)). Studies of Tangier Disease provide compelling evidence that ABCA1-dependent cholesterol efflux is required for HDL biogenesis in humans. Targeted disruption of the ABCA1 gene in mice produces a phenotype similar to human Tangier Disease while over-expression of ABCA1 protects against atherosclerosis, underscoring the importance of apoA-I/ABCA1 interactions in heart disease protection (see, e.g., McNeish et al., *Proc. Natl. Acad. Sci.* 97:4245-4250 (2000) and Singaraja et al., *J. Biol. Chem.* 277:22426-22429 (2002)). Apo A-I also stabilizes cellular ABCA1 protein preventing its degradation (Wang et al., *J. Clin. Invest.* 111:99-107 (2003); Martinez et al., *J. Biol. Chem.* 278:37368-37374 (2003); and Wang et al., *J. Biol. Chem.* 275: 33053-33058 (2000)). This represents a mechanism for up-regulating ABCA1 protein, one potential target of therapeutic intervention to optimizing cholesterol efflux and HDL assembly.

Identifying key amino acids and unique aspects of amphipathic α-helices of Apo A-I and other apolipoproteins that are required to stimulate ABCA-dependent cholesterol efflux may provide for the design of therapeutics to combat atherosclerosis and other disorders of where mediation of cholesterol efflux is desirable, i.e., diseases and disorders associated with dyslipidemia such as, e.g., heart disease, atherosclerotic lesions, stroke, Alzheimer's, and storage disorders.

Thus, there is a need in the art for additional compositions and methods for treating cardiovascular disease, i.e., by mediating cholesterol efflux, stabilizing ABCA. The present invention meets these and other needs.

BRIEF SUMMARY OF THE INVENTION

The present invention provides peptides and compositions with cholesterol efflux mediating activity, ABCA stabilization activity, antioxidant activity, and anti-inflammatory activity, methods of identifying additional compounds with such activity, and methods of delivering such activity.

In one embodiment, the invention provides isolated peptides having a cholesterol efflux mediating activity and an ABCA stabilization activity (e.g., an ABCA1 stabilization activity or an ABCA7 stabilization activity). The peptides comprise an amphipathic alpha helix from a protein selected from: Apo A-I, Apo A-II, Apo A-IV, Apo E, Apo C-I, Apo C-II, Apo C-III, serum amyloid A, and combinations thereof. The helix comprises at least 18 amino acids, a polar face, and a nonpolar face. The polar face comprises an alignment of at least 3 acidic amino acids positioned at every 2-3 helical turns. In some embodiments, the peptide comprises at least one amino acid substitution, insertion, or deletion in the native Apo A-I, Apo A-II, Apo A-IV, Apo E, Apo C-I, Apo C-II, Apo C-III, or serum amyloid A sequence to create the alignment of acidic amino acids. In some embodiments, at least one native amino acid residue at or near the polar/nonpolar interface of the amphipathic alpha helix is substituted with a cysteine. In some embodiments, the peptide has an antioxidant activity and/or an anti-inflammatory activity. In some embodiments, the peptides comprise at least 1, 2, 3, 4, 5, 6, 7, 8, 9, 10, or more D amino acids. In some embodiments, the carboxy terminus and the amino terminus of the peptide each comprise a D amino acid. In some embodiments, the peptides comprise all D amino acids. In some embodiments, helix comprises a sequence selected from: helix 1 (amino acids 44-65) of Apo A-I, helix 6 (amino acids 145-162) of Apo A-I, helix 7 (amino acids 167-184) of Apo A-I, helix 9 (amino acids209-219) of Apo A-I, helix 10 (amino acids 220-238) of Apo A-I, amino acids 1-51 of Apo A-II, amino acids 5-32 of Apo A-II, amino acids 62-94 of Apo A-IV, amino acids 66-90 of Apo A-IV, amino acids 183-204 of Apo A-IV, amino acids 183-226 of Apo A-IV, amino acids 205-226 of Apo A-IV, amino acids 161-204 of Apo A-IV, amino acids 161-182 of Apo A-IV, amino acids 205-248 of Apo A-IV, amino acids 227-248 of Apo A-IV, amino acids 117-138 of Apo A-IV, amino acids 138-160 of Apo A-IV, amino acids of 25-57 Apo C-I, amino acids 6-27 of Apo C-I, amino acids 29-53 of Apo C-I, amino acids 12-42 of Apo C-II, amino acids 16-40 of Apo C-II, amino acids 43-68 of Apo C-II, amino acids 37-69 of Apo C-III, amino acids 45-69 of Apo C-III, the C terminal domain (amino acids 216-299) of Apo E, amino acids 216-248 of Apo E, amino acids 216-237 of Apo E, amino acids 238-266 of Apo E, a amino acids 267-299 of Apo E, amino acids 238-263 of Apo E, amino acids 1-36 of serum amyloid A, amino acids 1-34 of serum amyloid A amino acids 5-29 of serum amyloid A, and amino acids 53-78 of serum amyloid A. In some embodiments, the peptide comprise a sequence selected from:

| Sequence | |
|---|---|
| PALEDLRQGLLPVLESFCVKFLSALEEYTKKLN; | (SEQ ID NO: 1) |
| PVLESFKVSFLSALEEYKTKLESALN; | (SEQ ID NO: 2) |
| QQARGWVTDGFSSLKDYWSTVKDKFSEFWDLDP; | (SEQ ID NO: 3) |
| ARMEEMGSRTRDRLDEVKEQVAEVRAKLEEQAQQIRLQAEAFQARLKSWFEPLVE DMQRQWAGLVEKVQAAVGTSAAPVPSDNH; | (SEQ ID NO: 4) |
| ARMEEMGSRTRDRLDEVKEQVAEVRAKLEEQAQ; | (SEQ ID NO: 5) |
| ARMEEMGSRTRDRLDEVKEQVA; | (SEQ ID NO: 6) |
| EVRAKLEEQAQQIRLQAEAFQARLKSWFEPVLE; | (SEQ ID NO: 7) |
| PLVEDMQRQWAGLVEKVQAAVGTSAAPVPSDNH; | (SEQ ID NO: 8) |
| EVRAKLEEWFQQIRLQAEEFQARLKS; | (SEQ ID NO: 9) |
| PFATELHERLAKDSEKLKEEIGKELEELRARLL; | (SEQ ID NO: 10) |
| ELHERLAKDSEKLKEEIGKELEELR; | (SEQ ID NO: 11) |
| PHADELKAKIDQNVEELKGRLTPYADEFKVKIDQTVEELRRSLA; | (SEQ ID NO: 12) |
| PHADELKAKIDQNVEELKGRLT; | (SEQ ID NO: 13) |
| PYADEFKVKIDQTVEELRRSLA; | (SEQ ID NO: 14) |
| PYADEFKVKIDQTVEELRRSLAPYAQDTQEKLNHQLEGLTFQMK; | (SEQ ID NO: 15) |
| PYAQDTQEKLNHQLEGLTFQMK; | (SEQ ID NO: 16) |
| PYAQDTQEKLNHQLEGLTFQMKKNAEELKARISASAEELRQRLA; | (SEQ ID NO: 17) |
| KNAEELKARISASAEELRQRLA; | (SEQ ID NO: 18) |
| PYADQLRTQVNTQAEQLRRQLT; | (SEQ ID NO: 19) |
| PLAQRMERVLRENADSLQASLR; | (SEQ ID NO: 20) |
| LISRIKQSELSAKMREWFSETFQKVKEKLKIDS; | (SEQ ID NO: 21) |
| SALDKLKEFGNTLEDKARELIS; | (SEQ ID NO: 22) |
| IKQSELSAKMREWFSETFQKVKEKL; | (SEQ ID NO: 23) |
| PTFLTQVKESLSSYWESAKTAAQNLYEKTYL; | (SEQ ID NO: 24) |
| TQVKESLSSYWESAKTAAQNLYEKT; | (SEQ ID NO: 25) |
| PAVDEKLRDLYSKSTAAMSTYTGIFT; | (SEQ ID NO: 26) |
| QQARGWVTDGFSSLKDYWSTVKDKFSEFWDLDP; | (SEQ ID NO: 27) |
| DGFSSLKDYWSTVKDKFSEFWDLDP; | (SEQ ID NO: 28) |
| QAKEPCVESLVSQYFQTVTDYGKDLMEKVKSPELQAEAKSYFEKSKEQLTP; | (SEQ ID NO: 29) |
| PCVESLVSQYFQTVTDYGKDLMEKVKSP; | (SEQ ID NO: 30) |

-continued

```
RSFFSFLGEAFDGARDMWRAYSDMREANYIGSDKYF;              (SEQ ID NO: 31)

RSFFSFLGEAFDGARDMWRAYSDMREANYIGSDK;                (SEQ ID NO: 32)

SFLGEAEFDGARDMWRAYSDMREANY;                        (SEQ ID NO: 33)

WAAEVISNARENIQRLTGHGAEDSLA;                        (SEQ ID NO: 34)

PALEDLRQGLLPVLESFKVSFLSALEEYTKKLN;                 (SEQ ID NO: 35)

LKLLDNWDSVTSTFSKLREQLGPVTQEFWDNLEKETEGLRQEMS;      (SEQ ID NO: 36)

LKLLDNWDSVTSTFSKLREQLGPALEDLRQGLL;                 (SEQ ID NO: 37)

ARLAEYHAKATEHLSTLSEKAKPVLESFKVSFLSALEEYTKKLN;      (SEQ ID NO: 38)

PYSDELRQRLAARLEALKENGGPVLESFKVSFLSALEEYTKKLN;      (SEQ ID NO: 39)

PLGEEMRDRARAHVDALRTHLAPVLESFKVSFLSALEEYTKKLN;      (SEQ ID NO: 40)
and

PALEDLRQGLLLKLLDNWDSVTSTFSKLREQLG.                 (SEQ ID NO: 41)
```

In some embodiments, the peptides further comprise a second amphipathic alpha helix as described herein. In some embodiments, the first and the second amphipathic helices comprise a sequence selected from the group consisting of: helix 1 (amino acids 44-65) of Apo A-I and helix 9 (amino acids 209-219) of Apo A-I linked in order; helix 9 (amino acids 209-219) of Apo A-I and helix 1 (amino acids 44-65) of Apo A-I linked in order; helix 6 (amino acids 145-162) of Apo A-I and helix 10 (amino acids 220-238) of Apo A-I linked in order; helix 7 (amino acids 167-184) of Apo A-I and helix 10 (amino acids 220-238) of Apo A-I linked in order; helix 9 (amino acids 201-219) of Apo A-I and helix 10 (amino acids 220-238) of Apo A-I linked in order; helix 6 (amino acids 145-162) of Apo A-I and helix 7 (amino acids 167-184) of Apo A-I linked in order; helix 1 (amino acids 44-65) of Apo A-I and helix 2 (amino acids 66-87) of Apo A-I linked in order; helix 8 (amino acids 185-209) of Apo A-I and helix 10 (amino acids 220-238) of Apo A-I linked in order; and the C terminal domain of Apo E (amino acids 216-299).

A further embodiment of the invention provides pharmaceutical compositions comprising the peptides described herein and a pharmaceutically acceptable carrier. In some embodiments, the pharmaceutical compositions further comprise a therapeutic agent (e.g., an agent that regulates plasma lipid levels or lowers blood pressure). Suitable therapeutic agents include, e.g., a statin such as atorvastatin, lovastatin, pravastatin, simvastatin, fluvastatin, cerivastatin, or rosuvastatin; a bile acid binder such as cholestyramine or colestipol; a platelet clumping inhibitor such as aspirin, ticlopidine, or clopidogrel, niacin/nicotinamide, a peroxisome proliferative activated receptor (PPAR) agonists such as tesaglitazar, Vitamin E; a cholesterol ester transfer protein (CETP) inhibitor such as ezetimibe, JTT-705, Torcetrapib; an angiotensin-converting enzyme (ACE) inhibitor such as Accupril, Aceon, Altace, Capoten, Lotensin, Mavik, Monopril, Prinivil, Univasc, Vasotec, or Zestril; β-blockers such as atenolol, metoprolol, propranolol; or combinations thereof, for treating a disease or disorder associated with cholesterol efflux (e.g., cardiovascular disease).

Another embodiment of the invention provides isolated nucleic acids encoding the peptides disclosed herein, expression vectors comprising the nucleic acids, and host cells comprising the expression vectors.

Even another embodiment of the invention provides mediating cholesterol efflux in a mammalian subject (e.g., a primate such as a human or chimpanzee or a rodent such as a rat or mouse) by administering the peptides described herein to the subject.

Even a further embodiment of the invention provides methods of making a non-naturally occurring peptide having a cholesterol efflux activity and/or ABCA (e.g., ABCA1 or ABCA7) stabilization activity by; identifying an amphipathic alpha helix peptide comprising a polar face and a nonpolar face in a protein selected from the group consisting of: Apo A-I, Apo A-II, Apo A-IV, Apo E, Apo C-I, Apo C-II, Apo C-III, and serum amyloid A wherein the amphipathic alpha helix peptide comprises between 5 to about 500, about 7 to about 300, about 10 to about 200, or about 25 to about 100 amino acids; modifying (e.g., by substitution, deletion, or insertion of one, two, three, or more amino acids) the polar face of the helix peptide to comprise an alignment of at least three acidic amino acids positioned at every 2-3 helical turns to create a modified helix peptide; selecting a modified helix peptide that has at least twice the cholesterol efflux mediating activity and/or at least twice the ABCA stabilization activity as the amphipathic alpha helix peptide; and synthesizing the modified helix peptide. In some embodiments, the modified helix peptide comprises one or more D amino acids. In some embodiments, the modified helix peptide comprises all D amino acids. In some embodiments, the modified helix peptide is further modified by substituting or inserting a thiol-bearing amino acid (e.g., Cys) at the polar/nonpolar interface of the helix.

Another embodiment of the invention provides methods of making a non-naturally occurring peptide having a cholesterol efflux activity and/or a ABCA stabilization activity by: identifying a first and a second amphipathic alpha helix peptide in a protein selected from the group consisting of: Apo A-I, Apo A-II, Apo A-IV, Apo E, Apo C-I, Apo C-II, Apo C-III, and serum amyloid A wherein the amphipathic alpha helix peptide comprises between 5 to about 500, about 7 to about 300, about 10 to about 200, or about 25 to about 100 amino acids; linking the first and second amphipathic alpha helix peptides to form an alignment of acidic amino acids wherein said acidic amino acids are positioned at every 2-3 helical turns to create a modified helix peptide; selecting a modified helix peptide that has at least twice the cholesterol efflux mediating activity and/or at least twice the ABCA stabilization activity as the amphipathic alpha helix peptide; and synthesizing the modified helix peptide. In some embodiments, the first or second amphipathic helix is modified (e.g., by substitution, deletion, or insertion of one, two, three, or more amino acids) to create the alignment of acidic amino acids. In some embodiments, the modified helix peptide comprises one or more D amino acids. In some embodiments, the modified helix peptide comprises all D amino acids. In some embodiments, the modified helix peptide is further modified by substituting or inserting a thiol-bearing amino acid (e.g., Cys) at the polar/nonpolar interface of the helix.

BRIEF DESCRIPTION OF THE DRAWINGS

FIG. 1 illustrates data demonstrating that a synthetic peptide (22-mer) based on helix 1 (aa 44-65) of apoA-I fails to mediate cholesterol efflux via ABCA1. Panels A and B, J774 macrophages were incubated (12 h) with (circles) and without (squares) a cAMP analog to up-regulate ABCA1 expression. The cholesterol efflux properties of the lipid-free form of helix 1 are shown in panel A, and efflux to lipid-flee full-length apoA-I is shown in panel B. The concentration of each acceptor was 75 µg/ml. Panel C, the dependence of cholesterol efflux on the concentration of the helix 1 peptide; shown are the results using cAMP-treated cells. A-I corresponds to full-length apoA-I (25 µg/ml). Values are the mean±S.D., n=3 (separate experiments). Error bars are smaller than symbols when not seen.

FIG. 8 illustrates data demonstrating that the C-terminal domain (aa216-299) of apoE is a potent stimulator of cholesterol efflux. Panel A, J774 macrophages were treated with (closed symbols) and without (open symbols) a cAMP analog and exposed to the C-terminal (CT, circles) and N-terminal (NT, squares) domains of apoE to assess cholesterol efflux. CT and NT portions of apoE were used in lipid-free form at 50 µg/ml. Panel B, Bar graph showing cholesterol efflux mediated by CT, NT and full-length apoE3, each at 50 µg/ml. All values are means±SD, n=3. Panel C, Helical net diagram showing the first 44 amino acids within the CT of apoE (SEQ ID NO:48). Shaded circles highlight the acidic residues and half-shaded circles positively charged amino acids. The alignment of acidic residues is marked by the vertical lines.

BRIEF DESCRIPTION OF THE SEQUENCES

Figures 2A, 2B, 2C:
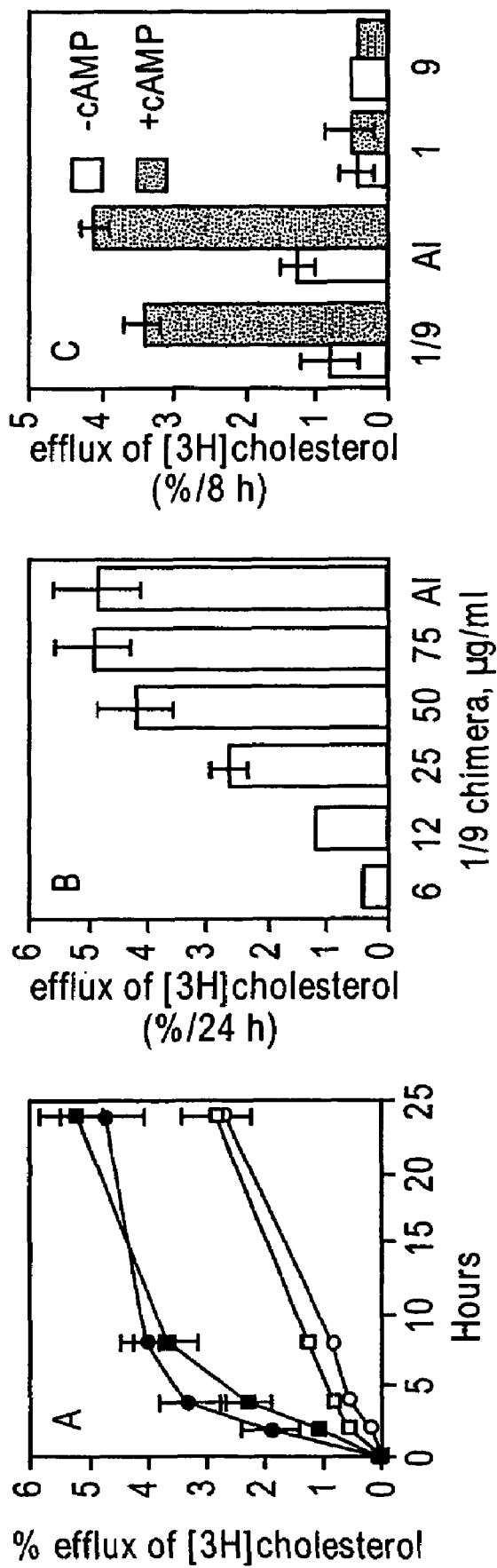
FIG. 2 illustrates data demonstrating that a chimeric peptide composed of apoA-I helices 1 and 9 mediates cholesterol efflux via ABCA1. Panel A, J774 macrophages were treated (12 h) with (closed circles and squares) and without (open circles and squares) a cAMP analog to up-regulate ABCA1 expression. Cholesterol efflux mediated by the helix 1/9 chimera is depicted by the open and closed squares, and full-length apoA-I is depicted by the open and closed circles. Panel B, the dependence of cholesterol efflux on the concentration of the lipid-free form of the 1/9 chimera; shown are the results using cAMP-treated cells. AI corresponds to the lipid-free form of full-length apoA-I (75 µg/ml). Panel C, cholesterol efflux to various acceptors including the 1/9 chimera, full-length apoA-I, helix 1 (aa 44-65), and helix 9 (aa 209-219). Each acceptor was used in lipid-free form at a concentration of 75 µg/ml. Values are the means±S.D., n=3.

SEQ ID NO:1 is a peptide comprising Helix 9 and 10 of Apo A-I linked in order and modified.
SEQ ID NO:2 is a peptide comprising Helix 10 of Apo A-I modified.
SEQ ID NO:3 is amino acid residues 37-69 of Apo C-III.
SEQ ID NO:4 is amino acid residues 216-299 of Apo E.
SEQ ID NO:5 is amino acid residues 216-248 of Apo E.
SEQ ID NO:6 is amino acid residues 216-237 of Apo E.
SEQ ID NO:7 is amino acid residues 238-266 of Apo E.
SEQ ID NO:8 is amino acid residues 267-299 of Apo E.
SEQ ID NO:9 is amino acid residues 238-263 of Apo E.
SEQ ID NO:10 is amino acid residues 62-94 of Apo A-IV.
SEQ ID NO:11 is amino acid residues 66-90 of Apo A-IV.
SEQ ID NO:12 is amino acid residues 161-204 of Apo A-IV.
SEQ ID NO:13 is amino acid residues 161-182 of Apo A-IV.
SEQ ID NO: 14 is amino acid residues 183-204 of Apo A-IV.
SEQ ID NO:15 is amino acid residues 183-226 of Apo A-IV.
SEQ ID NO:16 is amino acid residues 205-226 of Apo A-IV.
SEQ ID NO:17 is amino acid residues 205-248 of Apo A-IV.
SEQ ID NO:18 is amino acid residues 227-248 of Apo A-IV.
SEQ ID NO:19 is amino acid residues 117-138 of Apo A-IV.
SEQ ID NO:20 is amino acid residues 138-160 of Apo A-IV.
SEQ ID NO:21 is amino acid residues 25-57 of Apo C-I.
SEQ ID NO:22 is amino acid residues 6-27 of Apo C-I.
SEQ ID NO:23 is amino acid residues 29-53 of Apo C-I.
SEQ ID NO:24 is amino acid residues 12-42 of Apo C-II.
SEQ ID NO:25 is amino acid residues 16-40 of Apo C-II.
SEQ ID NO:26 is amino acid residues 43-68 of Apo C-II.
SEQ ID NO:27 is amino acid residues 37-69 of Apo C-III.
SEQ ID NO:28 is amino acid residues 45-69 of Apo C-III.
SEQ ID NO:29 is amino acid residues 1-51 of Apo A-II.
SEQ ID NO:30 is amino acid residues 5-32 of Apo A-II.
SEQ ID NO:31 is amino acid residues 1-36 of SAA.
SEQ ID NO:32 is amino acid residues 1-34 of SAA.
SEQ ID NO:33 is amino acid residues 5-29 of SAA.
SEQ ID NO:34 is amino acid residues 53-78 of SAA.
SEQ ID NO:35 is Apo A-I Helices 9 and 10 joined by a proline at residue 220.
SEQ ID NO:36 is a 22 mer of helix 1 of Apo A-I joined to a 22mer of helix 2 of Apo A-I by a proline residue.
SEQ ID NO:37 is Apo A-I Helices 1 and 9 having a 22mer of helix 1 of Apo A-I joined to an 1 mer of helix 9 of Apo A-I by a proline residue.
SEQ ID NO:38 is a 22mer of helix 8 of Apo A-I joined to a 22mer of helix 10 of Apo A-I by a proline residue.
SEQ ID NO:39 is a 22mer of helix 7 of Apo A-I joined to a 22mer of helix 10 of Apo A-I by a proline residue.
SEQ ID NO:40 is a 22mer of helix 6 of Apo A-I joined to a 22mer of helix 10 of Apo A-I by a proline residue.
SEQ ID NO:41 is an 11 mer of helix 9 of Apo A-I joined to a 22mer of helix 1 of Apo A-I.

DETAILED DESCRIPTION OF THE INVENTION

I. Introduction

The present invention is based on the surprising discovery that peptides comprising an amphipathic α-helix and an alignment of negatively charged amino acids along the helix possess cholesterol efflux activity and ABCA stabilization activity. In some cases, such peptides also possess an antioxidant activity, and/or an anti-inflammatory activity. Typically, the peptides are derived from apolipoproteins (e.g., Apo A-I, Apo A-II, Apo A-IV, Apo E, Apo C-I, Apo C-II, Apo C-III, or serum amyloid A). Accordingly, the invention provides compositions comprising such peptides, methods of identifying and synthesizing such peptides, and methods of treating, preventing, or diagnosing diseases and disorders associated with dyslipidemia such as, e.g., heart disease, atherosclerotic lesions, stroke, Alzheimer's (i.e., by ameliorating plaque deposition), and storage disorders by administering such peptides. The invention further provides methods of identifying and making the peptides described herein.

II. Definitions

The term "amphipathic alpha helix" or "amphipathic α helix" refers to a peptide helix with a polar face that comprises primarily hydrophilic amino acids (e.g., Asp, Glu, Gly, Ser, Thr, Cys, and Tyr) and nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Biophys. Chem.* 16:561 (1987) and *Science* 223:249 (1984).

The polar face of an amphipathic α helix typically comprises an "alignment of negatively charged amino acids" or "an alignment of acidic amino acids," i.e., a series of negatively charged or acidic amino acids (e.g., amino acids that are acidic at substantially neutral pH such as Asp or Glu or amino acids that have been modified so that they are acidic at approximately neutral pH such as modified Gly, Ser, Thr, Cys, or Tyr) positioned approximately evenly (e.g., at about every two to three helical turns) within the peptide sequence. Thus, the amino acid sequence of an amphipathic α helix typically alternates between hydrophilic and hydrophobic residues every 3 to 4 residues, since the α helix makes a turn approximately every 3.6 residues. Amphipathic a helices play a role in both intra- and intermolecular protein-protein interactions, and proteins and lipoproteins (e.g., including apolipoproteins) comprising amphipathic a helices have been postulated to play a role in lipid (e.g., HDL) function (see, e.g. Anantharamaiah et al., *Adv Exp Med Biol.* 285:131-40 (1991)). The structure and function of amphipathic a helices has been reviewed in, e.g., Segrest et al., *Proteins* 8(2):103-17 (1990). In silico methods of identifying amphipathic a helices have been described by. e.g., Jones et al., *J Lipid Res.* 33(2): 141-66 (1992). Multiple proteins comprising amphipathic a helices have been identified including, e.g., apolipoproteins and serum amyloid proteins.

The term "apolipoprotein" or Apo" or "exchangeable apolipoprotein" refers to any one of several helical proteins that can combine with a lipid (i.e., solubilize the lipid) to form a lipoprotein and are a constituent of chylomicrons, HDL, LDL, and VLDL. Apolipoproteins exert their physiological effect on lipid metabolism by binding to and activating specific enzymes or transporting proteins or lipids on the cell membranes (e.g., via the ABC transporters). Apolipoproteins include, e.g., Apo A-I, Apo A-II, Apo A-IV, Apo C-I, Apo C-II, Apo C-III, Apo E, and serum amyloid proteins such as, serum amyloid A. Apolipoproteins typically have a cholesterol efflux mediating activity which, in some cases, is accompanied by a phospholipid efflux activity.

The term "ABCA stabilization activity" refers to enhancing or extending the half life of an ABCA protein (e.g., ABCA1 or ABCA7). A compound (e.g., an apolipoprotein) that has ABCA stabilization activity that is at least 25%, 50%, 75%, 100% or at least 2 fold, 4 fold, 8 fold, 10 fold higher than the ABCA stabilization activity in the absence of the compound. Proteins having an ABCA stabilization activity mediate cholesterol efflux through a specific ABCA pathway. Other pathways for cholesterol efflux (e.g., detergent-like pathways) do not involve ABCA stabilization.

The term "cholesterol efflux activity" refers to efflux of cholesterol from any cell type. For example, macrophage foam-cells in the artery wall release cholesterol. A compound that mediates cholesterol efflux activity may enhance the rate of cholesterol efflux from a cell or promote efflux of the total amount of cholesterol from a cell. A compound that enhances the rate of cholesterol efflux, enhances the rate of cholesterol efflux by at least 25%, 50%, 75%, 100% or by at least 2 fold, 4 fold, 8 fold, 10 fold or more compared to the rate of cholesterol efflux in the absence of the compound.

The term "Apolipoprotein AI" or Apo A-I refers to a polypeptide comprising 243 amino acids forming N- and C-terminal domains (see, e.g., Saito et al., *J. Biol. Chem.* 278:23227-23232 (2003) and Saito et al., *Prog. Lipid Res.* 43:350-380 (2004)). The tertiary structure of apoA-I comprises a helix bundle with N-terminal segments and central helices (aa 1-186) together with a C-terminal domain (aa 187-243) that binds lipid strongly (see, e.g., Saito et al., *Prog. Lipid Res.* 43:350-380 (2004) and Mishra et al., *Biochemistry.* 37:10313-10324 (1998)). Residues 44-243 of apoA-I contain the necessary structural determinants for mediating cholesterol efflux via ABCA1 (see, e.g., Chroni et al., *J. Biol. Chem.* 278:6719-6730 (2003) and Natarajan et al., *J. Biol. Chem.* 279:24044-24052 (2004)). This region of apoA-I (aa44-243) is comprised of a series of ten amphipathic α-helices of 11- and 22-amino acids separated by proline residues, as defined by exon 4 of the apoA-I gene (see, e.g., Borhani et al., *Proc. Natl. Acad. Sci.* 94:12291-6 (1997)). The 11-mer helical segment represents the smallest theoretical unit of α-helix forming three complete turns of secondary structure; whereas, the 22-mer helix probably emerged via duplication events within the apoA-I gene (see, e.g., Saito et al., *J. Biol. Chem.* 278:23227-23232 (2003)). The α-helical segments of apoA-I are defined, in part, by the relative distribution of positively charged residues and are designated as Class A or Y (see, e.g., Saito et al., *J. Biol. Chem.* 278:23227-23232 (2003)). Class A helices possess positively charged amino acids at the lipid-water interface, while class Y helices exhibit a positively charged amino acid toward the middle of the polar surface in addition to interfacial cationic residues. A truncated form of apoA-I (A-I Δ1-43) has been crystallized (see, e.g., Borhani et al., *Acta Crystallogr. D. Biol. Crystallogr.* 55:1578-1583 (1999) and Segrest et al., *J. Biol. Chem.* 274:31755-31758 (1999)). This has lead to a helical belt model by which two apoA-I molecules orient in an anti-parallel fashion around the edge of nascent, discoidal HDL (see, e.g., Klon et al., *Biophys. J.* 79:1679-1685 (2000) and Jones et al., *J. Lipid Res.* 33:287-296 (1992)). Information derived from the apoA-I crystal structure and molecular modeling techniques reveal that negatively charged amino acids align, in linear fashion, down the polar surface of helices 5-10 of apoA-I, which coincides with helical segments implicated in mediating ABCA1-dependent cholesterol efflux (see, e.g., Borhani et al., *Acta Crystallogr. D. Biol. Crystallogr.* 55:1578-1583 (1999); Segrest et al., *J. Biol. Chem.* 274: 31755-31758 (1999); Klon et al., *Biophys. J.* 79:1679-1685 (2000); and Jones et al., *J. Lipid Res.* 33:287-296 (1992)). Natarajan et al. demonstrated that the alignment of negatively charged amino acids are important for mediating cholesterol efflux and stabilizing ABCA1 (see, e.g., *J. Biol. Chem.* 279 (23): 24044-24052 (2004)). Apo AI sequences are set forth in, e.g., Genbank Accession Nos.: P02647, J0009; AAB64381; AAB22835; 1613168A; 1403292A; CAA25519; CAA26097; and LPHUA1.

Each of the amphipathic α-helices represented by aa 44-243 of apoA-I is capable of binding to phospholipid surfaces. However, helices 1 (aa 44-65) and 10 (aa 220-241) possess the highest lipid-binding affinity in isolated form as synthetic 22-mer peptides (see, e.g., Gillotte et al., *J. Biol. Chem.* 274:2021-2028 (1999)). As such, helices 1 and 10 have been implicated as mediators of cellular cholesterol efflux and nascent HDL assembly. Despite the fact that helices 1 and 10 possess high lipid-binding affinity, only helix 1 is able to stimulate cholesterol efflux in the form of a synthetic 22-mer, as judged in studies utilizing cholesterol loaded fibroblasts (see, e.g., Charulatha et al., *J. Biol. Chem.* Paper in press M406924200 (2004)). The failure of helix 10 to stimulate cholesterol efflux was attributed to its slightly lower monolayer exclusion pressure, which (apparently) was less than that of helix 1 that stimulated cholesterol efflux. Deletion of helix 10 (aa 220-243) from apoA-I dramatically reduces (~80-90%) cholesterol efflux capability via the ABCA1 pathway, consistent with the idea that high lipid-binding affinity is, indeed, required to facilitate interactions with ABCA1 expressing cells (see, e.g., Chroni et al., *J. Biol. Chem.* 278: 6719-6730 (2003) and Natarajan et al., *J. Biol. Chem.* 279: 24044-24052 (2004)). In support of this, substitution of K238 (confers class Y structure in helix 10) with an acidic residue decreases the lipid-binding affinity of apoA-I and reduces cholesterol efflux (see, e.g., Chroni et al., *J. Biol. Chem.* 278:6719-6730 (2003)).

Apolipoprotein A-II" or "Apo A-II" refers to the second major apolipoprotein of high density lipoprotein in human plasma. Mature Apo A-II is present as a dimer of two 77-amino acid chains joined by a disulfide bridge (see, e.g., Tailleux et al., *Atherosclerosis* 164(1):1-13 (2002)). Apo A-II regulates many steps in HDL metabolism, and its role in coronary heart disease is unclear (see, id.). In bovine serum, the Apo A-II homologue is present in almost free form. Bovine Apo A-II shows antimicrobial activity against *Escherichia coli* and yeasts in phosphate buffered saline (PBS) (see, e.g., Motizuki et al., *J Biochem* (Tokyo) 123(4): 675-9 (1998)).

"Apolipoprotein A-IV" or "Apo A-IV" refers to a glycoprotein secreted together with triglyceride-rich lipoproteins by the small intestine. Intestinal Apo A-IV synthesis is stimulated by fat absorption, probably mediated by chylomicron formation. Intestinal Apo A-IV synthesis is also stimulated by members of the pancreatic polypeptide family, including peptide YY (PYY), neuropeptide Y (NPY), and pancreatic polypeptide (PP). Recently, Apo A-IV was demonstrated to be present in the hypothalamus as well. Hypothalamic Apo A-IV level was reduced by food deprivation and restored by lipid feeding. Intracerebroventricular administration of Apo A-IV antiserum stimulated feeding and decreased the hypothalamic apo A-IV mRNA level, implying that feeding is intimately regulated by endogenous hypothalamic apo A-IV. Central administration of NPY significantly increased hypothalamic apo A-IV mRNA levels in a dose-dependent manner. Apo A-IV sequences are set forth in Genbank Accession Nos.: NP_000473; P06727; and AAB59516.

The term "Apolipoprotein E" or "Apo E" refers to a blood plasma protein that plays an important role in lipid homeostasis in the artery wall as well as in the brain (see, e.g., Wahrle et al., *J. Biol. Chem.* 279:40987-40993 (2004)). Apo E is synthesized and secreted by macrophage foam-cells within atherosclerotic lesions where it functions to maintain cellular cholesterol homeostasis (see, e.g., Wahrle et al., *J. Biol. Chem.* 279:40987-40993 (2004) and may play a role in reversing the macrophage foam-cell phenotype. Apo E has been shown to compete with Apo A-I for binding to ABCA1 expressing cells and formation of a molecular complex with ABCA1, suggesting a common mechanism by which helical apolipoproteins stimulate cellular cholesterol efflux (see, e.g., Stephens et al., *Lancet* 347:781-786 (1996)). In its capacity as a modulator of cellular cholesterol homeostasis, Apo E forms a molecular complex with ABCA1 in stimulating cholesterol efflux (see, e.g., Hirsch-Reinshagen et al., *J. Biol. Chem.* 279:41197-41207 (2004); Krimbou et al., *J. Lipid Res.* 45:839-848 (2004); and Stephens et al., *Lancet* 347:781-786 (1996)50-52)). Defective Apo E/ABCA1 interactions in the brain are believed to dramatically reduce extracellular Apo E levels and interfere with intercellular lipid transport contributing to the development of neurological disorders (see, e.g., Hirsch-Reinshagen et al., *J. Biol. Chem.* 279:41197-41207 (2004) and Krimbou et al., *J. Lipid Res.* 45:839-848 (2004)).

The architecture of apoE amphipathic α-helices is somewhat different than that of apoA-I. Unlike apoA-I which possesses several overlapping helical segments with aligned acidic residues, aligned acidic residues in apoE appear to be limited to a helical stretch within (aa216-248) the C-terminal domain. The C terminal domain of apoE is composed of two, long helical stretches separated via a proline residue. The first segment consists of 51 amino acids (residues 216-266) and the second 33 residues (aa267-299). The former is Class A and the latter Class G with negative residues located at the lipid-water interface and positive residues toward the middle of polar surface. Apo E forms an unusually elongated four-helix bundle that may be stabilized by a tightly packed hydrophobic core that includes leucine zipper-type interactions and by numerous salt bridges on the mostly charged surface. Basic amino acids important for LDL receptor binding are clustered into a surface patch on one long helix (see, e.g., Wilson et al., *Science* 28; 252(5014):1817-22 (1991)). The α-helices in apoE are generally longer, i.e. not often interrupted with proline residues like the 22-mer segments in apoA-I and the molecule is divided into well defined N-terminal four helix bundle and C-terminal lipid binding domain separated via a "hinge" region (see, e.g., Segrest et al., *J. Lipid. Res*. 33:141-166 (1992); Saito et al. *J. Biol. Chem*. 278:23227-23232 (2003); Saito et al., *Prog. Lipid Res.* 43:350-380 (2004); and Dong et al., *J. Biol. Chem.* 269: 22358-22365 (1994)). Apo E sequences are set forth in Genbank Accession Nos.: NM_000041; P02649; AAH03557; AAB59397; and AAB59518.

"Apolipoprotein C-I" or Apo C-I refers to a water-soluble protein component of plasma lipoprotein. Apo C-I solublizes lipids and regulates lipid metabolism. Apo C-1 transfers among HDL (high density lipoprotein), VLDL (very low-density lipoprotein) and chylomicrons. Apo C-1 activates lecithin:cholesterol acetyltransferase (LCAT), inhibits cholesteryl ester transfer protein, can inhibit hepatic lipase and phospholipase 2 and can stimulate cell growth. Apo C-1 delays the clearance of beta-VLDL by inhibiting its uptake via the LDL receptor-related pathway (see, e.g., Gursky, *Biochemistry* 9; 40(40):12178-85 (2001). Apo C-1 has been implicated in hypertriglyceridemia (see, e.g., Schachter, *Curr Opin Lipidol.* 2001 June; 12(3):297-304 (2001)), and Alzheimer's disease (see, e.g., Petit-Turcotte et al., *Neurobiol Dis.* 8(6):953-63 (2001)). Apo C-I is postulated to comprise two dynamic helices that are stabilized by interhelical interactions and are connected by a short linker region. The minimal folding unit in the lipid-free state of this and other exchangeable apolipoproteins comprises the helix-turn-helix motif formed of four 11-mer sequence repeats. Apo C-I possesses four acidic residues that form an alignment that spans six helical turns, which is created by 33- of the 57-amino acids that comprise the apolipoprotein (see, e.g., Saito et al., *J. Biol. Chem.* 278:23227-23232 (2003)). Apo C-I sequences are set forth in Genbank Accession Nos.: NM_001645; NP_001636; and P02654.

"Apolipoprotein C-II" or "Apo C-II" refers to a polypeptide that is the major activator of lipoprotein lipase, a key enzyme in theregulation of triglyceride levels in human serum (see, e.g., Storjohann, et al., *Biochim Biophys Acta.* 2000 Jul. 19; 1486(2-3):253-64 (2001)). Apo C-II sequences are set forth in Genbank Accession Nos.: NM_000483; X05151; P02655; NP_000474; LPHUC2; and AAB26668.

"Apolipoprotein C-III" or "Apo C-III" refers to a 79-residue glycoprotein synthesized in the intestine and liver as part of the very low density lipoprotein (VLDL) and the high density lipoprotein (HDL) particles. Apo C-III is postulated to play a role in lipid metabolism and, accordingly, atherosclerosis. Apo C-III may act by inhibiting lipoprotein lipase (LPL) activity, as shown by in vitro experiments. Elevated levels of Apo-C-III may also displace other apolipoproteins at the lipoprotein surface, modifying their clearance from plasma (see, e.g., Lins et al., *Protein Eng.* 15(6):513-20 (2002). Apo C-III sequences are set forth in Genbank Accession Nos.: NM_000040; V01513; and NP_000031.

"Serum amyloid A" or "SAA" refers to a member of the superfamily of acute-phase proteins, i.e., any protein whose plasma concentration increases (or decreases) by 25% or more during certain inflammatory disorders. The level of serum amyloid A (SAA) in the blood increases dramatically in response to tissue injury and inflammation. SAA also acts as a cytokine, influencing cell adhesion, migration, proliferation and aggregation. Other acute-phase proteins include, e.g., C-reactive protein (CRP), fibrinogen, and alpha 1-acid glycoprotein. The members of the SAA superfamily include, e.g., SAA1, SAA2, SAA3, and SAA4. The gene for the SAA superfamily is on chromosome 11p15.1. SAA1 and SAA2 have 90% nucleotide identity while SAA3 shows 70% identity with SAA1 and SAA2. The gene order on 11p15.1 is cen--SAA1--SAA2--SAA4--SAA3--pter where cen=the centromere and pter=the end of the short arm of chromosome 11. SAA sequences are set forth in Genbank Accession Nos.: NM_000331; NM_199161; NM_030754; NM 006512; AB055860; AB055859; BC007022; X51445; X51444; X51443; X51442; X51441; X51440; X51439; X56653; X56652; X13895; B1481129; S73444; NP_000322; NP 954630; NP_110381; P02735; NP_006503; P35542; AAH07022; P22614; A38974; YLHUA; YLHUS; 139456; CAA35808; CAA35807; CAA35806; CAA35805; CAA35804; CAA35810; CAA35809; CAA39975; CAA39974; BAA06768.

The term "chimeric polypeptide" as used herein refers to a polypeptide comprising two or more helices from the same protein that are not adjacent to each other in the native protein and two or more helices from two or more different proteins.

The term "ABC" or "ATP Binding Cassette" multidomain membrane proteins, responsible for the controlled efflux and influx of allocrites (e.g. cholesterol) across cellular membranes. ABC proteins comprise four domains, with two transmembrane domains (TMDs) responsible for allocrite binding and transport and two nucleotide-binding domains (NBDs) responsible for coupling the energy of ATP hydrolysis to conformational changes in the TMDs. The family members include, e.g., ABCA1 and ABCA7. ABCA1 is characterized in Denis et al., *J. Biol. Chem.* 2004 Oct. 1; 279(40):41529-36 (2004). ABCA1 plays a role in cholesterol efflux and is upregulated in cells which are exposed to cholesterol enriching conditions. ABCA1 turns over rapidly and has a half life of about 1 hour (see, e.g., Wang et al., *J. Clin. Invest.* 111:99-107 (2003)). ABCA1 sequences are set forth in Genbank Accession Nos.: AJ012376; NM_173076; NM_015657; NM_005502; NP_005493; O95477. The promoter structure and genomic organization of the human ABCA7 gene is described in Broccardo et al., *Cytogenet Cell Genet*. 92(3-4): 264-70 (2001). ABCA7 sequences are set forth in Genbank Accession Nos.: NM 033308; NM_019112; NP_150651; NP_061985; AAK00959. A family of related ATP-binding proteins has been characterized (see, e.g., Higgins et al., *J Bioenerg Biomembr*. 22(4):571-92 (1990); Higgins et al., *Bioessays* 8(4):111-6 (1988); Higgins et al., *Nature* 323(6087):448-50 (1986); Doolittle et al., *Nature* 323(6087): 451-3 (1986); and Blight and Holland, *Mol Microbiol*. 4(6): 873-80 (1990)). The proteins belonging to this family also contain one or two copies of the 'A' consensus sequence (see, e.g., Walker et al., *EMBO* 1(8):945-51 (1982)) or the 'P-loop' (see, e.g., Saraste et al., *Trends Biochem Sci*. 1990 November; 15(11):430-4 6155 (1990)). ABCA family members are reviewed in Broccardo et al., *Biochimica et Biophysica Acta* 1461:395-404 (1999).

The term "antioxidant activity" refers to prevention or reduction of oxidation caused by reactive oxygen species ROS including, e.g., hydrogen peroxide ($H_2O_2$); hypochlorite ion (—OCl); hydroxyl radical (—OH); and the superoxide anion ($O_2$—). A number of naturally occurring substances (e.g., proteins and small molecules) possess antioxidant activity. For example, apolipoproteins can inhibit lipid peroxidation, thus protecting phospholipid surfaces from lipophilic, as well as, water soluble free radical initiators (see, e.g., *Biochemistry* 41:2089-2096 (2002)). In addition, alpha-tocopherol (vitamin E) is an antioxidant. A compound with an antioxidant activity, has an antioxidant activity that is at least 25%, 50%, 75%, 100% or at least 2 fold, 4 fold, 8 fold, 10 fold higher than the antioxidant activity in the absence of the compound.

The term "anti-inflammatory activity" refers to prevention or reduction of inflammation. A compound with an anti-inflammatory activity, has an anti-inflammatory activity that is at least 25%, 50%, 75%, 100% or at least 2 fold, 4 fold, 8 fold, 10 fold higher than the antioxidant activity in the absence of the compound.

A disease or disorder associated with dyslipidemia is any disease or disorder in which lipid metabolism is disregulated (e.g., due to aberrant mediation of cholesterol efflux or aberrant ABCA stabilization). Such diseases include, for example, heart disease, atherosclerotic lesions, stroke, Alzheimer's, and storage disorders.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. Apo A-I, Apo A-II, Apo A-IV, Apo C-I, Apo C-II, Apo C-III, Apo E, and serum amyloid A proteins, polypeptides, and peptides include full length Apo A-I, Apo A-II, Apo A-IV, Apo C-I, Apo C-II, Apo C-III, Apo E, and serum amyloid A proteins as well as subsequences of Apo A-I, Apo A-II, Apo A-IV, Apo C-I, Apo C-II, Apo C-III, Apo E, and serum amyloid A proteins including, e.g., peptides comprising the sequences set forth in SEQ ID NOS: 1-41, peptides comprising the sequence of helix 1, 2, 3, 4, 5, 6, 7, 8, 9, 10 10 of Apo A-I, or peptides comprising the C-terminal sequence of Apo E.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of ÿ-sheet and ÿ-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the peptide, and used to detect antibodies specifically reactive with the peptide).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as Helix 1, 6, 7, 9, or 10 of Apo A-I, or the C terminal of Apo E), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to Apo A-I, Apo A-II, Apo A-IV, Apo E, Apo C-I, Apo C-II, Apo C-III, or Serum Amyloid A nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to," refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec –2 min., an annealing phase lasting 30 sec. –2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Peptides

The Apo A-I, Apo A-II, Apo A-IV, Apo E, Apo C-I, Apo C-II, Apo C-III, or serum amyloid A peptides of the invention comprise at least one amphipathic α-helix comprising an alignment of acidic residues. The acidic residues are positioned at about every 2-3 helical turns. The helix is typically about 32 Å in length. The helix is typically about 10 to about 60 amino acids in length, more typically about 20 to about 44 amino acids in length, more typically about 20 to about 30 amino acids in length, even more typically about 22-26 amino acids in length, most typically about 24 amino acids in length.

The amphipathic α-helix comprising the alignment of acidic amino acids may be naturally occurring in a protein (e.g., Apo A-I, Apo A-II, Apo A-IV, Apo E, Apo C-I, Apo C-II, Apo C-III, or serum amyloid A) or may be introduced, i.e., by a substitution of a basic or neutral amino acid with an acidic amino acid, by the deletion of an amino acid, or the insertion of acidic amino acids into the amphipathic α-helix sequence. For example, acidic amino acids may be added to either end of the amphipathic α-helix sequence or may be introduced at a suitable position within the amphipathic α-helix to create an alignment of acidic residues. In some embodiments, the peptide is modified by the introduction of a thiol bearing amino acid (e.g., a cysteine) at or near the polar/nonpolar interface of the amphipathic α-helix which confers antioxidant properties to the peptide (see, e.g. U.S. Patent Publication No. 20030087819). Typically, an Apo A-I, Apo A-II, Apo A-IV, Apo E, Apo C-I, Apo C-II, Apo C-III, or serum amyloid A peptide of the invention comprises no more than 1, 2, 3, 4, 5, 6, 7, 8, 9, or 10 amino acid substitutions, insertions, or deletions compared to the native Apo A-I, Apo A-II, Apo A-IV, Apo E, Apo C-I, Apo C-II, Apo C-III, or serum amyloid A peptide sequences.

In some embodiments, the peptides may be designed to possess more than one activity. For example, peptide comprising an amphipathic α-helix comprising an alignment of acidic amino acids and having cholesterol efflux mediating activity and ABCA stabilization activity may be modified to comprise a thiol-bearing amino acid at the polar/nonpolar interface of the helix, thus conferring an antioxidant activity to the peptide and generating a peptide with cholesterol efflux mediating activity, ABCA stabilization activity, and antioxidant activity.

In some embodiments, the peptides further comprise a second, third, fourth, or fifth amphipathic alpha helix. In these embodiments, one or more of the additional helices may comprise substitutions, deletions, or insertions to introduce an alignment of acidic amino acids into the helix, or to introduce a thiol-bearing amino acid a the polar/nonpolar interface of the helix. All of the helices may be from the same protein or may be from different proteins. If the helices are from the same protein, they may comprise overlapping sequences from the protein, or sequences that are not adjacent in the native protein. For example, a chimeric peptide may be generated by linking in order helix 1 of Apo A-I to helix 9 of Apo A-I, by linking in order helix 9 or Apo A-I to helix 1 of Apo A-I, by linking in order, helix 9 of Apo A-I to helix 10 of Apo A-2, by linking in order helix 6 of Apo A-I to helix 7 of Apo A-I, or by linking in order helix 10 of Apo A-I with any one of the sequence set forth in SEQ ID NOS: 1-41. The helices may be directly linked to each other, may be linked by a proline residue, or may be linked by any other linker known in the art. The linkage may be introduced through recombinant means or chemical means. Methods of introducing linkages recombinantly are well known to those of skill in the art and are described below. Exemplary chemical linkages include, for example, covalent bonding, including disulfide bonding; hydrogen bonding; electrostatic bonding; recombinant fusion; and conformational bonding, e.g., biotin-avidin associations. Additional linkers and methods of linking are described in WO 98/41641.

Chimeric peptides may be designed so that each α-helix possesses the same or different activities. For example, one α-helix in a chimeric peptide may have cholesterol efflux mediating activity and ABCA stabilization activity and another α-helix in the chimeric peptide may have an anti-oxidant activity. Alternatively, all of the helices in a chimeric peptide may have cholesterol efflux mediating activity, ABCA stabilization activity, and an anti-oxidant activity.

Any method known in the art can be used to verify that any substitutions, deletions, insertions, or other changes to the peptide sequences do not alter the overall secondary structure and α-helical content of the Apo A-I, Apo A-II, Apo A-IV, Apo E, Apo C-I, Apo C-II, Apo C-III, or serum amyloid A peptides of the invention. For example, circular dichroism spectroscopy can be used. In addition, thermal- and guanidine-denaturation experiments can be used establish that each variant exhibits the same free energy of denaturation as described for WT-Apo A-I, Apo A-II, Apo A-IV, Apo E, Apo C-I, Apo C-II, Apo C-III, or serum amyloid A peptides.

A. Chemical Synthesis

The Apo A-I, Apo A-II, Apo A-IV, Apo E, Apo C-I, Apo C-II, Apo C-III, or serum amyloid A peptides can be chemically synthesized using methods known in the art including, e.g. solid phase synthesis (see, e.g., Merrifield, *J. Am. Chem. Soc.* 85:2149-2154 (1963) and Abelson et al., Methods in Enzymology, Volume 289: Solid-Phase Peptide Synthesis (1st ed. 1997). Protein synthesis may be performed using manual techniques or by automation. Automated synthesis may be achieved, for example, using Applied Biosystems 431A Peptide Synthesizer (Perkin Elmer). Alternatively, various fragments of the Apo A-I, Apo A-II, Apo A-IV, Apo E, Apo C-I, Apo C-II, Apo C-III, or serum amyloid A peptides described herein may be chemically synthesized separately and combined using chemical methods to produce the full length molecule by, for example, liquid phase synthesis. For example, Helix 1 and Helix 9 of Apo A-I may be separately synthesized and linked in order using methods known in the art. The sequence and mass of the peptides can be verified by GC mass spectroscopy. Once synthesized, peptides may be modified by N-terminal acetyl- and C-terminal amide-groups. Synthesized peptides can be further isolated by HPLC to a purity of at least about 80%, preferably 90%, and more preferably 95%.

B. Recombinant Expression

The Apo A-I, Apo A-II, Apo A-IV, Apo E, Apo C-I, Apo C-II, Apo C-III, or serum amyloid A peptides described herein can also be expressed recombinantly.

This invention relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

In general, the nucleic acid sequences encoding Apo A-I, Apo A-II, Apo A-IV, Apo E, Apo C-I, Apo C-II, Apo C-III, or serum amyloid A peptides and related nucleic acid sequence homologues can be cloned from cDNA and genomic DNA libraries or isolated using amplification techniques with oligonucleotide primers. For example, Apo A-I, Apo A-II, Apo A-IV, Apo E, Apo C-I, Apo C-II, Apo C-III, or serum amyloid A sequences are typically isolated from nucleic acid (genomic or cDNA) libraries by hybridizing with a nucleic acid probe, the sequence of which can be derived from any one of SEQ ID NOS: 1-41, or subsequence thereof. Apo A-I, Apo A-II, Apo A-IV, Apo E, Apo C-I, Apo C-II, Apo C-III, or serum amyloid A RNA and genomic DNA can be isolated from any mammal including: primates such as humans, monkeys, and chimpanzees; rodents, including mice and rats. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA*, 72:3961-3965 (1975)).

Nucleic acids encoding Apo A-I, Apo A-II, Apo A-IV, Apo E, Apo C-I, Apo C-II, Apo C-III, or serum amyloid A can also be isolated from expression libraries using antibodies as probes. Such polyclonal or monoclonal antibodies can be raised using, for example, the polypeptides comprising the sequences set forth in SEQ ID NOS: 1-41, and methods known in the art (see, e.g., Harlow and Lane, Antibodies: A Laboratory Manual (1988).

Apo A-I, Apo A-II, Apo A-IV, Apo E, Apo C-I, Apo C-II, Apo C-III, or serum amyloid A polymorphic variants, alleles, and interspecies homologues that are substantially identical to Apo A-I, Apo A-II, Apo A-IV, Apo E, Apo C-I, Apo C-II, Apo C-III, or serum amyloid A can be isolated using Apo A-I, Apo A-II, Apo A-IV, Apo E, Apo C-I, Apo C-II, Apo C-III, or serum amyloid A nucleic acid probes and oligonucleotides under stringent hybridization conditions, by screening libraries. Alternatively, expression libraries can be used to clone Apo A-I, Apo A-II, Apo A-IV, Apo E, Apo C-I, Apo C-II, Apo C-III, or serum amyloid A polymorphic variants, alleles, and interspecies homologues, by detecting expressed homologues immunologically with antisera or purified antibodies made against the core domain of Apo A-I, Apo A-II, Apo A-IV, Apo E, Apo C-I, Apo C-II, Apo C-III, or serum amyloid A which also recognize and selectively bind to the Apo A-I, Apo A-II, Apo A-IV, Apo E, Apo C-I, Apo C-II, Apo C-III, or serum amyloid A homologue.

An alternative method of isolating Apo A-I, Apo A-II, Apo A-IV, Apo E, Apo C-I, Apo C-II, Apo C-III, or serum amyloid A nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). The primers can be used, e.g., to amplify either the full length sequence or a probe of one to several hundred nucleotides, which is then used to screen a cDNA library for full-length Apo A-I, Apo A-II, Apo A-IV, Apo E, Apo C-I, Apo C-II, Apo C-III, or serum amyloid A. Methods such as polymerase chain reaction (PCR) and ligase chain reaction (LCR) can be used to amplify nucleic acid sequences of Apo A-I, Apo A-II, Apo A-IV, Apo E, Apo C-I, Apo C-II, Apo C-III, or serum amyloid A directly from mRNA, from cDNA, from genomic libraries or cDNA libraries. Degenerate oligonucleotides can be designed to amplify Apo A-I, Apo A-II, Apo A-IV, Apo E, Apo C-I, Apo C-II, Apo C-III, or serum amyloid A homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Apo A-I, Apo A-II, Apo A-IV, Apo E, Apo C-I, Apo C-II, Apo C-III, or serum amyloid A encoding mRNA in physiological samples, for nucleic acid sequencing, or for other purposes. Genes amplified by the PCR reaction can be purified from agarose gels and cloned into an appropriate vector.

Gene expression of Apo A-I, Apo A-II, Apo A-IV, Apo E, Apo C-I, Apo C-II, Apo C-III, or serum amyloid A can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

The Apo A-I, Apo A-II, Apo A-IV, Apo E, Apo C-I, Apo C-II, Apo C-III, or serum amyloid A peptides may be modified to comprise an alignment of acidic amino acids by introducing appropriate nucleotide changes into the DNA encoding the polypeptide of interest. Such modifications include, for example, deletions from, or insertions or substitutions of, residues within the amino acid sequence of the Apo A-I, Apo A-II, Apo A-IV, Apo E, Apo C-I, Apo C-II, Apo C-III, or serum amyloid A peptide of interest so that it contains the an alignment of acidic amino acids as described herein. Any combination of deletion, insertion, and substitution is made to arrive at the final construct, provided that the final construct possesses the desired characteristics.

To obtain high level expression of a cloned gene or nucleic acid sequence, such as those cDNAs encoding Apo A-I, Apo A-II, Apo A-IV, Apo E, Apo C-I, Apo C-II, Apo C-III, or serum amyloid A, one typically subclones an Apo A-I, Apo A-II, Apo A-IV, Apo E, Apo C-I, Apo C-II, Apo C-III, or serum amyloid A peptide sequence (e.g., a full length Apo A-I, Apo A-II, Apo A-IV, Apo E, Apo C-I, Apo C-II, Apo C-III, or serum amyloid A or a sequence encoding SEQ ID NOS: 1-34) into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding Apo A-I, Apo A-II, Apo A-IV, Apo E, Apo C-I, Apo C-II, Apo C-III, or serum amyloid A or a subsequence thereof. Suitable bacterial promoters are well known in the art and described, e.g., in Sambrook et al. and Ausubel et al. The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant Apo A-I, Apo A-II, Apo A-IV, Apo E, Apo C-I, Apo C-II, Apo C-III, or Serum Amyloid A peptides to provide convenient methods of isolation, e.g., His tags. In some case, enzymatic cleavage sequences (e.g., Met-(His)$_6$-Ile-Glu-GLy-Arg (SEQ ID NO:49) which form the Factor Xa cleavage site) are added to the recombinant Apo A-I, Apo A-II, Apo A-IV, Apo E, Apo C-I, Apo C-II, Apo C-III, or Serum Amyloid A peptides. Bacterial expression systems for expressing the Apo A-I, Apo A-II, Apo A-IV, Apo E, Apo C-I, Apo C-II, Apo C-III, or Serum Amyloid A peptides are available in, e.g., E. coli, Bacillus sp., and Salmonella (Palva et al., Gene 22:229-235 (1983); Mosbach et al., Nature 302:543-545 (1983)). Kits for such expression systems are commercially available. Eukaryotic expression systems for mammalian cells, yeast, and insect cells are well known in the art and are also commercially available.

Standard transfection methods are used to produce cell lines that express large quantities of Apo A-I, Apo A-II, Apo A-IV, Apo E, Apo C-I, Apo C-II, Apo C-III, or serum amyloid A, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of cells is performed according to standard techniques (see, e.g., Morrison, J. Bact. 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Apo A-I, Apo A-II, Apo A-IV, Apo E, Apo C-I, Apo C-II, Apo C-III, or serum amyloid A.

After the expression vector is introduced into the cells, the transfected cells are cultured under conditions favoring expression of Apo A-I, Apo A-II, Apo A-IV, Apo E, Apo C-I, Apo C-II, Apo C-III, or serum amyloid A. Apo A-I, Apo A-II, Apo A-IV, Apo E, Apo C-I, Apo C-II, Apo C-III, or serum amyloid A can also be recovered from the culture using standard techniques identified below.

C. Purification of Peptides

Either naturally occurring or recombinant Apo A-I, Apo A-II, Apo A-IV, Apo E, Apo C-I, Apo C-II, Apo C-III, or serum amyloid A peptides (e.g., full length Apo A-I, Apo A-II, Apo A-IV, Apo E, Apo C-I, Apo C-II, Apo C-III, or serum amyloid A peptides or peptides comprising the sequences set forth in SEQ ID NOS: 1-41) can be purified. Naturally occurring Apo A-I, Apo A-II, Apo A-IV, Apo E, Apo C-I, Apo C-II, Apo C-III, or serum amyloid A peptides are purified, e.g., from a biological sample (e.g., animal and human body fluids such as whole blood, serum, plasma, cerebrospinal fluid, urine, lymph fluids, and various external secretions of the respiratory, intestinal and genitourinary tracts, tears, saliva, milk, cell extracts, cell culture supernatants; fixed tissue specimens; and fixed cell specimens). Any source of Apo A-I, Apo A-II, Apo A-IV, Apo E, Apo C-I, Apo C-II, Apo C-III, or serum amyloid A, including, e.g., mammals such as primates and rodents.

Apo A-I, Apo A-II, Apo A-IV, Apo E, Apo C-I, Apo C-II, Apo C-III, or serum amyloid A peptides may be purified to substantial purity by standard techniques known in the art, including, for example, extraction and purification from inclusion bodies, size differential filtration, solubility fractionation (i.e., selective precipitation with such substances as ammonium sulfate); column chromatography, immunopurification methods, and others (see, e.g., Scopes, Protein Purification: Principles and Practice (1982); U.S. Pat. No. 4,673, 641; Ausubel et al., supra; and Sambrook et al., supra).

A number of procedures can be employed when Apo A-I, Apo A-II, Apo A-IV, Apo E, Apo C-I, Apo C-II, Apo C-III, or serum amyloid A peptides are being purified. For example, proteins having established molecular adhesion properties can be reversible fused to recombinant Apo A-I, Apo A-II, Apo A-IV, Apo E, Apo C-I, Apo C-II, Apo C-III, or serum amyloid A peptides. With the appropriate ligand, the recombinant Apo A-I, Apo A-II, Apo A-IV, Apo E, Apo C-I, Apo C-II, Apo C-III, or serum amyloid A peptides can be selectively adsorbed to a purification column and then freed from the column in a relatively pure form. The fused protein is then removed by enzymatic activity. Finally, Apo A-I, Apo A-II, Apo A-IV, Apo E, Apo C-I, Apo C-II, Apo C-III, or serum amyloid A peptides may be purified using immunoaffinity columns.

IV. Methods of Identifying Peptides with Desired Activity

The Apo A-I, Apo A-II, Apo A-IV, Apo E, Apo C-I, Apo C-II, Apo C-III, or Serum Amyloid A peptides and nucleic acids described in herein can be used to identify additional compounds that mediate cholesterol efflux and/or stabilize ABCA (e.g., ABCA1) can be using methods well known to those of skill in the art.

A number of different screening protocols can be utilized to identify compounds (e.g., helical peptides) that mediate cholesterol efflux and/or stabilize ABCA (e.g., ABCA1). In general terms, the screening methods involve screening a plurality of test compounds (e.g., candidate helical peptides) to identify a compound that mediates cholesterol efflux and/or stabilizes ABCA (e.g., ABCA1) in, e.g., mammalian cells, including human cells.

Candidate helical peptides can also be screened for other activities including, e.g., anti-oxidant activities and anti-inflammatory activities.

A. Screening for Cholesterol Efflux Activity

Suitable cholesterol efflux assays are described in, e.g., Bielicki, J. K and Oda, M. N., *Biochemistry*, 41:2089-2096 (2002); Jia, Z. et al., *Biochem. Biophys. Res. Common.*, 297: 206-213 (2002). In some embodiments, a polypeptide known to mediate cholesterol efflux (e.g., helix 9/10 of Apo A-I) is used to screen for additional mediators of cholesterol efflux in a cell based assay. For example, cell lines in which cholesterol efflux can be enhanced using a cAMP analog that up-regulates ABCA1 protein expression (e.g., J774 macrophages) can conveniently be used to assess the ability of an Apo A-I, Apo A-II, Apo A-IV, Apo E, Apo C-I, Apo C-II, Apo C-III, or Serum Amyloid A peptide to mediate cholesterol efflux. The cells are incubated with labeled cholesterol (e.g., [$^3$H]cholesterol) under conditions appropriate for cholesterol uptake by the cells. cAMP or cAMP analogs (e.g., CPT-cAMP) is incubated with the cells for a suitable time before the initiation of cellular cholesterol efflux, i.e., prior to contacting the cells with helix 9/10 of Apo A-I or the test compound. Measurement of labeled cholesterol appearing in the medium is used to determine the cholesterol efflux mediating activity of the test compound.

B. Screening for ABCA Stabilization Activity

Multiple assays known in the art can be used to measure the ABCA stabilization activity of a test compound (e.g., an Apo A-I, Apo A-II, Apo A-IV, Apo E, Apo C-I, Apo C-II, Apo C-III, or Serum Amyloid A peptide). For example, binding assays may be used to test the ability of the test compound to bind to ABCA (e.g., ABCA1), as at least some of the compounds so identified are also likely mediators of cholesterol efflux. The binding assays may be competitive assays. Other assays include direct measurement of ABCA (e.g., ABCA protein or nucleic acids) following contact with the test compound.

1. Binding Assays

Binding assays usually involve contacting ABCA with one or more test compounds and allowing sufficient time for ABCA and test compounds to form a binding complex. Any binding complexes formed can be detected using any of a number of established analytical techniques. Protein binding assays include, but are not limited to, immunohistochemical binding assays, flow cytometry or other assays. In some embodiments, competition assays are used to determine whether a test compound has ABCA stabilization activity. Competition assays are well known in the art. Typically, a competitor compound, i.e., a compound known to bind ABCA, is labeled so that differences in binding to ABCA (e.g., in the presence of increasing amount of a test compound (e.g., an Apo A-I, Apo A-II, Apo A-IV, Apo E, Apo C-I, Apo C-II, Apo C-III, or Serum Amyloid A peptide) that may bind to ABCA) can be measured. The particular label or detectable group used in the assay is not a critical aspect of the invention, as long as it does not significantly interfere with the binding of the test compound to ABCA. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADSTM), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

In some embodiments, ABCA expressing and non-expressing cells are used to measure the ABCA (e.g., ABCA1) stabilization activity of a test compound by measuring the relative ABCA binding affinities of the test compound and a competitor compound (e.g., full-length apoA-I A or Apo A-I 9/10 peptide) for ABCA. In some embodiments, the binding affinity of full-length apoA-I A to ABCA is compared to the binding affinity of a labeled peptide (e.g., a radiolabeled Apo A-I, Apo A-II, Apo A-IV, Apo E, Apo C-I, Apo C-II, Apo C-III, or Serum Amyloid A peptide) as described in, e.g., Remaley et al., *J. Lipid Res.*, 44:828-836 (2003). Cells expressing ABCA are incubated in the presence and absence of the competitor compound, and then exposed to a range of concentrations of individual labeled test peptides (e.g., a radiolabeled Apo A-I, Apo A-II, Apo A-IV, Apo E, Apo C-I, Apo C-II, Apo C-III, or Serum Amyloid A peptide). Typically, the concentrations of test peptides will range from about 0.1 µg/ml to about 200 µg/ml, about 0.5 µg/ml to about 100 µg/ml, about 1 µg/ml to about 40 µg/ml, or about 5 µg/ml to about 20 µg/ml.

2. Direct Measurement of ABCA

In some embodiments, the stabilization of ABCA is measured by direct measurement of ABCA (e.g., ABCA protein, or nucleic acid) using a cell based assay. Cell based assays can be performed in any cells in which ABCA is expressed (e.g., J774 macrophages), including cells which have transfected with ABCA (e.g. HeLa cells). Any cell type can be used. For example, J774 macrophages can be used to assess relative ABCA1 protein levels in the presence and absence of Apo A-I, Apo A-II, Apo A-IV, Apo E, Apo C-I, Apo C-II, Apo C-III, or Serum Amyloid A peptides. The cells are first contacted with a compound that will induce ABCA (e.g., cAMP or a cAMP analogue such as, 8-bromo-cAMP) to upregulate ABCA (e.g., ABCA1) expression, then exposed to synthetic ABCA1 protein levels in the presence and absence of Apo A-I, Apo A-II, Apo A-IV, Apo E, Apo C-I, Apo C-II, Apo C-III, or Serum Amyloid A peptides in the absence of the cAMP stimulus to evaluate whether ABCA1 protein was stabilized or degraded. Relative levels of ABCA1 protein can be assessed using any means known in the art including, e.g., immunoblot analysis of cell membranes (Oram, J. F. et al., *J. Biol. Chem.*, 278:52379-52385 (2003) or hybrization of nucleic acid probes to ABCA mRNA).

C. Screening for Antioxidant Activity

Apo A-I, Apo A-II, Apo A-IV, Apo E, Apo C-I, Apo C-II, Apo C-III, or Serum Amyloid A peptides can be screened for antioxidant activity using methods known in the art. For example, U.S. Patent Publication No. 20030087819 describes multiple assays that can be used to determine the antioxidant acitivity of a peptide, including, e.g., micelle substrate assays. A micelle substrate comprising a phospholipids (e.g., 1-palmitoyl-2-linoleoylphosphatidylcholine) is used to measure rates of lipid peroxidation catalyzed by specific enzymes (e.g., soybean lipoxygenase and/or xanthine/xanthine oxidase). The enzymes initiate lipid peroxidation following the addition of recombinant Apo A-I, Apo A-II, Apo A-IV, Apo E, Apo C-I, Apo C-II, Apo C-III, or Serum Amyloid A peptides to the phospholipid micelles. Increases in conjugated dienes (a product of lipid peroxidation) are monitored by ultraviolet absorption spectroscopy (234 nm) at 25° C. The mass of phospholipid hydroperoxides is calculated using the molar absorptivity coefficient ($\epsilon$=29,500 Lcm$^{-1}$ mol$^{-1}$) of conjugated dienes. Initial rates of lipoxygenase mediated lipid peroxidation are calculated from the slopes of the linear portion of the oxidation curves and results can be expressed as nmoles of phospholipid peroxide formed/min. Based on the maximum levels of lipid peroxide accumulation obtained in the absence of peptide (i.e., the plateau associated with the oxidation curves), it is possible to derive quantitative information regarding the potency of the Apo A-I, Apo A-II, Apo A-IV, Apo E, Apo C-I, Apo C-II, Apo C-III, or Serum Amyloid A peptides (i.e., the concentration of Apo A-I, Apo A-II, Apo A-IV, Apo E, Apo C-I, Apo C-II, Apo C-III, or Serum Amyloid A peptides resulting in 50% protection against lipid peroxidation), D. Screening for Anti-Inflammatory Activity Apo A-I, Apo A-II, Apo A-IV, Apo E, Apo C-I, Apo C-II, Apo C-III, or Serum Amyloid A peptides can be screened for anti-inflammatory activity using any means known in the art. For example, assays to assess the activity of enzymes (e.g., lecithin:cholesterol acetyltransferase (LCAT) or paraoxonase (PON)) sensitive to inflammatory events can be used to assess the anti-inflammatory activity of the peptides of the inventions. Suitable assays are described in, e.g., Chen, C.-H. and J. J. Albers., *J. Lipid Res.*, 23:680-691 (1982) which describes quantification of LCAT activity using an exogenous proteoliposome substrate, and Forte, T. M. et al., *J. Lipid Res.*, 43:477-485 (2002) which describes quantification of PON activity.

E. Further Testing

Compounds that are initially identified as mediating cholesterol efflux or interacting with ABCA can be further tested to validate their ability to mediate cholesterol efflux and/or stabilize ABCA. The basic format of such methods involves administering a lead compound identified during an initial screen to an animal that serves as a model. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like). In a preferred embodiment, Apo E –/– mice, Apo A-II –/– mice, or Apo C-III –/– mice are used. Additional animal models are described in, e.g., Marschang and Herz, *Sem. Cell Dev. Biol.* 14:25-35 (2003).

F. Modification of Candidate Helix

Once a compound (e.g., a peptide) has been identified as a compound that mediates of cholesterol efflux and/or stabilizes ABCA, additional modifications can be made to the peptide to enhance its properties or to confer additional properties. For example, amino acid substitutions, deletions, or insertions can be made to create an alignment of acidic residues or to introduce a thiol-bearing amino acid at the polar/nonpolar interface. D-amino acids may be incorporated at one or more positions in the peptide, e.g., at one or both ends or within the peptide. In addition, the peptide may be linked to another amphipathic α-helix polypeptide.

G. Candidate Compounds

The agents tested as a potential mediators of cholesterol efflux and/or ABCA stabilizers can be any small chemical compound, or a biological entity, such as a polypeptide, sugar, nucleic acid or lipid. Alternatively, modulators can be genetically altered versions of Apo A-I, Apo A-II, Apo A-IV, Apo E, Apo C-I, Apo C-II, Apo C-III, or Serum Amyloid A. Essentially any chemical compound can be used as a test compound in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5H-bond donors (expressed as the sum of OHs and NHs); having a molecular weight over 500; having a LogP over 5 (or MLogP over 4.15); and/or having more than 10H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

H. High Throughput Screening

In one embodiment, high throughput screening (HTS) methods are used to identify compounds that mediate cholesterol efflux and/or stabilize ABCA. HTS methods involve providing a combinatorial chemical or peptide library containing a large number of potential therapeutic compounds (i.e., compounds that mediate cholesterol efflux or stabilize ABCA). Such "libraries" are then screened in one or more assays, as described herein, to identify those library members (particular peptides, chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., ECIS TM, Applied Biophysics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

V. Methods of Treatment

The Apo A-I, Apo A-II, Apo A-IV, Apo E, Apo C-I, Apo C-II, Apo C-III, or Serum Amyloid A peptides and nucleic acids of the present invention can be used to treat or prevent a variety of disorders associated with dyslipidemia including, e.g., heart disease, atherosclerotic lesions, stroke, Alzheimer's (i.e., by ameliorating plaque deposition), and storage disorders. A disorder associated with dyslipidemia is diagnosed using criteria generally accepted in the art for detecting such disorders. The peptides and nucleic acids are administered to a patient in an amount sufficient to elicit a therapeutic response in the patient (e.g., regression of atherosclerotic lesions, amelioration of plaque deposition, or elevation of serum HDL). An amount adequate to accomplish this is defined as "therapeutically effective dose or amount."

The peptides and nucleic acids of the invention can be administered directly to a mammalian subject using any route known in the art, including e.g., by injection (e.g., intravenous, intraperitoneal, subcutaneous, intramuscular, or intrademal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Administration of the peptides and nucleic acids of the invention can be in any convenient manner, e.g., by injection, intravenous and arterial stents (including eluting stents), cather, oral administration, inhalation, transdermal application, or rectal administration. In some cases, the peptides and nucleic acids are formulated with a pharmaceutically acceptable carrier prior to administration. Pharmaceutically acceptable carriers are determined in part by the particular composition being administered (e.g., nucleic acid or polypeptide), as well as by the particular method used to administer the composition. Accordingly, there are a wide variety of suitable formulations of pharmaceutical compositions of the present invention (see, e.g., Remington's Pharmaceutical Sciences, 17th ed., 1989).

The dose administered to a patient, in the context of the present invention should be sufficient to effect a beneficial therapeutic response in the patient over time. The dose will be determined by the efficacy of the particular vector (e.g. peptide or nucleic acid) employed and the condition of the patient, as well as the body weight or surface area of the patient to be treated. The size of the dose also will be determined by the existence, nature, and extent of any adverse side-effects that accompany the administration of a particular peptide or nucleic acid in a particular patient.

In determining the effective amount of the vector to be administered in the treatment or prophylaxis of diseases or disorder associated with dyslipidemia, the physician evaluates circulating plasma levels of the polypeptide or nucleic acid, polypeptide or nucleic acid toxicities, progression of the disease (e.g., atherosclerosis), and the production of antibodies that specifically bind to the peptide. Typically, the dose equivalent of a polypeptide is from about 0.1 to about 50 mg per kg, preferably from about 1 to about 25 mg per kg, most preferably from about 1 to about 20 mg per kg body weight. In general, the dose equivalent of a naked nucleic acid is from about 1 μg to about 100 μg for a typical 70 kilogram patient, and doses of vectors which include a viral particle are calculated to yield an equivalent amount of therapeutic nucleic acid.

For administration, polypeptides and nucleic acids of the present invention can be administered at a rate determined by the LD-50 of the polypeptide or nucleic acid, and the side-effects of the polypeptide or nucleic acid at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

A. Injectable Delivery

In certain circumstances it will be desirable to deliver the pharmaceutical compositions comprising the Apo A-I, Apo A-II, Apo A-IV, Apo E, Apo C-I, Apo C-II, Apo C-III, or Serum Amyloid A peptides and nucleic acids disclosed herein parenterally, intravenously, intramuscularly, or even intraperitoneally as described in U.S. Pat. No. 5,543,158; U.S. Pat. No. 5,641,515 and U.S. Pat. No. 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

B. Implanted Devices

In some embodiments implanted devices (e.g., arterial and intravenous stents, including eluting stents, and catheters) are used to deliver the formulations comprising the Apo A-I, Apo A-II, Apo A-IV, Apo E, Apo C-I, Apo C-II, Apo C-III, or Serum Amyloid A peptides and nucleic acids of the invention. For example, aqueous solutions comprising the peptides and nucleic acids of the invention are administered directly through the stents and catheters. In some embodiments, the stents and catheters may be coated with formulations comprising the peptides and nucleic acids described herein. In some embodiments, the peptides and nucleic acids will be in time-release formulations an eluted from the stents. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829,497; 6,827,798; 6,827,730; 6,827,703; 6,824,554; 6,824,553; 6,824,551; 6,824,532; and 6,819,951. C. Liposomes In certain embodiments, the inventors contemplate the use of liposomes, nanocapsules, microparticles, microspheres, lipid particles, vesicles, and the like, for the administration of the Apo A-I, Apo A-II, Apo A-IV, Apo E, Apo C-I, Apo C-II, Apo C-III, or Serum Amyloid A peptides and nucleic acids of the present invention. In particular, the compositions of the present invention may be formulated for delivery either encapsulated in a lipid particle, a liposome, a vesicle, a nanosphere, or a nanoparticle or the like.

The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 400 nm, from 50 nm to 300 nm, or from 75 nm to 200 nm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

Targeting is generally not a limitation in terms of the present invention. However, should specific targeting be desired, methods are available for this to be accomplished. For example, antibodies may be used to bind to the liposome surface and to direct the liposomes and its contents to particular cell types. Carbohydrate determinants (glycoprotein or glycolipid cell-surface components that play a role in cell-cell recognition, interaction and adhesion) may also be used as recognition sites as they have potential in directing liposomes to particular cell types.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684).

D. Other Methods of Delivery

The Apo A-I, Apo A-II, Apo A-IV, Apo E, Apo C-I, Apo C-II, Apo C-III, or Serum Amyloid A peptides and nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In certain applications, the pharmaceutical compositions comprising the Apo A-I, Apo A-II, Apo A-IV, Apo E, Apo C-I, Apo C-II, Apo C-III, or Serum Amyloid A peptides and nucleic acids disclosed herein may be delivered via oral administration to the individual. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

E. Gene Therapy

In certain embodiments, the nucleic acids encoding Apo A-I, Apo A-II, Apo A-IV, Apo E, Apo C-I, Apo C-II, Apo C-III, serum amyloid A amphipathic α-helix polypeptides can be used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses an Apo A-I, Apo A-II, Apo A-IV, Apo E, Apo C-I, Apo C-II, Apo C-III, or serum amyloid A peptide of the present invention, thereby mitigating the effects of a disease associated with dyslipidemia.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)). For delivery of nucleic acids, viral vectors may be used. Suitable vectors include, for example, herpes simplex virus vectors as described in Lilley et al., *Curr. Gene Ther.* 1(4):339-58 (2001), alphavirus DNA and particle replicons as decribed in e.g., Polo et al., *Dev. Biol.* (Basel) 104:181-5 (2000), Epstein-Barr virus (EBV)-based plasmid vectors as described in, e.g., Mazda, *Curr. Gene Ther.* 2(3):379-92 (2002), EBV replicon vector systems as described in e.g., Otomo et al., *J. Gene Med.* 3(4):345-52 (2001), adeno-virus associated viruses from rhesus monkeys as described in e.g., Gao et al., *PNAS USA.* 99(18):11854 (2002), adenoviral and adeno-associated viral vectors as described in, e.g., Nicklin and Baker, *Curr. Gene Ther.* 2(3): 273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al. (1988) *Mol. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling and Smith (1994) *Gene Therapy* 1: 165-169; and Zhou et al. (1994) *J. Exp. Med.* 179:1867-1875). Additional suitable vectors include E1B gene-attenuated replicating adenoviruses described in, e.g., Kim et al., *Cancer Gene Ther.* 9(9):725-36 (2002) and non-replicating adenovirus vectors described in e.g., Pascual et al., *J. Immunol.* 160(9):4465-72 (1998) Exemplary vectors can be constructed as disclosed by Okayama et al. (1983) *Mol. Cell. Biol.* 3:280.

Molecular conjugate vectors, such as the adenovirus chimeric vectors described in Michael et al. (1993) *J. Biol. Chem.* 268:6866-6869 and Wagner et al. (1992) *Proc. Natl. Acad. Sci. USA* 89:6099-6103, can also be used for gene delivery according to the methods of the invention.

In one illustrative embodiment, retroviruses provide a convenient and effective platform for gene delivery systems. A selected nucleotide sequence encoding an Apo A-I, Apo A-II, Apo A-IV, Apo E, Apo C-I, Apo C-II, Apo C-III, or serum amyloid A amphipathic α-helix polypeptides can be inserted into a vector and packaged in retroviral particles using techniques known in the art. The recombinant virus can then be isolated and delivered to a subject. Suitable vectors include lentiviral vectors as described in e.g., Scherr and Eder, *Curr. Gene Ther.* 2(1):45-55 (2002). Additional illustrative retroviral systems have been described (e.g., U.S. Pat. No. 5,219,740; Miller and Rosman (1989) *BioTechniques* 7:980-990; Miller (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Curr. Opin. Genet. Develop.* 3:102-109).

Other known viral-based delivery systems are described in, e.g., Fisher-Hoch et al. (1989) *Proc. Natl. Acad. Sci. USA* 86:317-321; Flexner et al. (1989) *Ann. N.Y. Acad. Sci.* 569: 86-103; Flexner et al. (1990) *Vaccine* 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; Guzman et al. (1993) *Cir. Res.* 73:1202-1207; and Lotze and Kost, *Cancer Gene Ther.* 9(8):692-9 (2002).

F. Combination Therapy

In some embodiments, the polypeptides and nucleic acids are administered in combination with a second therapeutic agent for treating or preventing cardiovascular disease, including atherosclerosis. For example, an Apo A-I, Apo A-II, Apo A-IV, Apo E, Apo C-I, Apo C-II, Apo C-III, serum amyloid peptide may be administered in conjunction with a second therapeutic agent for treating or preventing cardiovascular disease. For example, an Apo A-I, Apo A-II, Apo A-IV, Apo E, Apo C-I, Apo C-II, Apo C-III, serum amyloid peptide may be administered in conjunction with any of the standard treatments for atherosclerosis including, for example, statins (e.g., atorvastatin, lovastatin, pravastatin, simvastatin, fluvastatin, cerivastatin, or rosuvastatin), bile acid binders (e.g., cholestyramine or colestipol), platelet clumping inhibitors (e.g., aspirin, ticlopidine, or clopidogrel), niacin/nicotinamide, peroxisome proliferative activated receptor (PPAR) agonists (e.g., tesaglitazar), angotensin converting enzyme (ACE) inhibitors (e.g., Accupril, Aceon, Altace, Capoten, Lotensin, Mavik, Monopril, Prinivil, Univasc, Vasotec, or Zestril), cholesterol ester transferase protein (CETP) inhibitors (e.g., ezetimibe, JTT-705, or Torcetrapib), β-blockers (e.g., atenolol, metoprolol, propranolol), Vitamin E, surgical intervention (e.g., angioplasty, stents, stents, or endarterectomy), and combinations thereof and lifestyle changes (e.g., low-fat diets, weight loss, and exercise).

The Apo A-I, Apo A-II, Apo A-IV, Apo E, Apo C-I, Apo C-II, Apo C-III, serum amyloid peptide and the second therapeutic agent may be administered simultaneously or sequentially. For example, the Apo A-I, Apo A-II, Apo A-IV, Apo E, Apo C-I, Apo C-II, Apo C-III, serum amyloid peptide may be administered first, followed by the second therapeutic agent. Alternatively, the second therapeutic agent may be administered first, followed by the Apo A-I, Apo A-II, Apo A-IV, Apo E, Apo C-I, Apo C-II, Apo C-III, serum amyloid peptide. In some cases, the Apo A-I, Apo A-II, Apo A-IV, Apo E, Apo C-I, Apo C-II, Apo C-III, serum amyloid peptide and the second therapeutic agent are administered in the same formulation. In other cases the Apo A-I, Apo A-II, Apo A-IV, Apo E, Apo C-I, Apo C-II, Apo C-III, serum amyloid peptide and the second therapeutic agent are administered in different formulations. When the Apo A-I, Apo A-II, Apo A-IV, Apo E, Apo C-I, Apo C-II, Apo C-III, serum amyloid peptide and the second therapeutic agent are administered in different formulations, their administration may be simultaneous or sequential.

In some cases, the Apo A-I, Apo A-II, Apo A-IV, Apo E, Apo C-I, Apo C-II, Apo C-III, serum amyloid peptides can be used to target therapeutic agents to cells and tissues expressing ABCA.

VI. Methods of Diagnosis

In some embodiments, the Apo A-I, Apo A-II, Apo A-IV, Apo E, Apo C-I, Apo C-II, Apo C-III, serum amyloid peptides of the invention may be used in methods of diagnosing diseases and disorders associated with aberrant cholesterol efflux or with ABCA. For example, in some embodiments, the Apo A-I, Apo A-II, Apo A-IV, Apo E, Apo C-I, Apo C-II, Apo C-III, serum amyloid peptides are used in in vivo imaging methods. The peptides are conjugated to a detectable moiety and administered to a subject (e.g., a mammal such as a human). Detection of the detectable moiety allows imaging of a cell, tissue, or organ of interest, including, e.g., an atherosclerotic lesion or an amyloid plaque.)

The term "imaging" refers to a procedure or modality for generating an image of a detectable moiety in vivo, ex vivo, or in vitro, as described herein or known to one of skill in the art. Examples of imaging modalities include magnetic resonance, nuclear magnetic resonance, radioscintigraphy, positron emission tomography, computed tomography, near-infrared fluorescence, X-ray, ultra sound, ultraviolet light, or visible light, but are not limited thereto (see, e.g., Dahnhert, Radiology Review Manual (4th ed. 1999); Brant et al., Fundamentals of Diagnostic Radiobiology (2nd ed. 1999); Weissleder et al., Primer of Diagnostic Imaging (2nd ed. 1997); Buddinger et al., Medical Magnetic Resonance A Primer, Society of Magnetic Resonance, Inc. (1988); and Weissleder et al., Nature Biotech. 17: 375-378 (1999)). In a preferred embodiment, the image of the detectable moiety is indicative of the activity of ABCA.

The phrase "detectable moiety" as used herein refers to a moiety that can be imaged and/or detected in vivo, ex vivo, or in vitro, by a procedure or modality described herein or known to one of skill in the art. As used herein, the detectable moiety can be directly or indirectly linked to an Apo A-I, Apo A-II, Apo A-IV, Apo E, Apo C-I, Apo C-II, Apo C-III, or serum amyloid peptide. A linker may serve to link the Apo A-I, Apo A-II, Apo A-IV, Apo E, Apo C-I, Apo C-II, Apo C-III, or serum amyloid peptide to one detectable moiety. Alternatively, a linker may link the Apo A-I, Apo A-II, Apo A-IV, Apo E, Apo C-I, Apo C-II, Apo C-III, or serum amyloid peptide to more than one detectable moiety. Likewise a detectable moiety may be linked to more than one linker. The use of a plurality of detectable moieties attached to one Apo A-I, Apo A-II, Apo A-IV, Apo E, Apo C-I, Apo C-II, Apo C-III, or serum amyloid peptide may enable the detectability of the detectable moiety to be increased (e.g. by increasing its radiopacity, echogenicity or relaxivity) or may enable it to be detected in more than one imaging modality.

Linking of a detectable moiety to an Apo A-I, Apo A-II, Apo A-IV, Apo E, Apo C-I, Apo C-II, Apo C-III, or serum amyloid peptide may be achieved by covalent or noncovalent means, usually involving interaction with one or more functional groups located on the detectable moiety and/or ligand. Examples of chemically reactive functional groups which may be employed for this purpose include amino, hydroxyl, sulfhydryl, carboxyl, and carbonyl groups, as well as carbohydrate groups, vicinal dials, thioethers, 2-aminoalcohols, 2-aminothiols, guanidinyl, imidazolyl and phenolic groups. In some embodiments, labile linkages, e.g. containing spacer arms which are biodegradable or chemically sensitive or which incorporate enzymatic cleavage sites are used. The particular linker is not a critical aspect of the invention. Any linker known in the art may be used as long it is binds the Apo A-I, Apo A-II, Apo A-IV, Apo E, Apo C-I, Apo C-II, Apo C-III, or serum amyloid peptide and detectable moieties together for an adequate period, i.e., a period sufficient for the contrast agent to exert its desired effects, e.g. to enhance contrast in vivo during a diagnostic imaging procedure.

The detectable moieties used in the methods of the present invention may be any moiety capable of detection either directly or indirectly in an imaging procedure described herein or known to one of skill in the art. For example, the following detectable moieties may be used: moieties which emit or may be caused to emit detectable radiation (e.g. by radioactive decay, fluorescence excitation, spin resonance excitation, etc.), moieties which affect local electromagnetic fields (e. paramagnetic, superparamagnetic, ferrimagnetic or ferromagnetic species), moieties which absorb or scatter radiation energy (e.g. chromophores, particles (including gas or liquid containing vesicles), heavy elements and compounds thereof, etc.), and moieties which generate a detectable substance (e.g. gas microbubble generators).

A very wide range of materials detectable by imaging modalities is known from the art and the detectable moiety will be selected according to the imaging modality to be used. Thus for example for ultrasound imaging an echogenic material, or a material capable of generating an echogenic material will normally be selected, for X-ray imaging the detectable moiety will generally be or contain a heavy atom (e.g., of atomic weight 38 or above), for MR imaging the detectable moiety will either be a non zero nuclear spin isotope (such as $^{19}F$) or a material having unpaired electron spins and hence paramagnetic, superparamagnetic, ferrimagnetic or ferromagnetic properties, for light imaging the detectable moiety will be a light scatterer (e.g. a colored or uncolored particle), a light absorber or a light emitter, for magnetometric imaging the detectable moiety will have detectable magnetic properties, for electrical impedance imaging the detectable moiety will affect electrical impedance and for scintigraphy, SPECT, PET etc. the detectable moiety will be a radionuclide.

Examples of suitable detectable moieties are widely known from the diagnostic imaging literature, e.g. magnetic iron oxide particles, gas-containing vesicles, chelated paramagnetic metals (such as Gd, Dy, Mn, Fe etc.). See for example U.S. Pat. Nos. 5,228,446; 4,647,447; 4,863,715; 4,770,183; WO 97/25073, WO 96/09840, WO 85/02772, WO 92/17212, WO 97/29783, EP-A-554213, WO 91/15243, WO 93/05818, WO 96/23524, WO 96/17628, U.S. Pat. No. 5,387,080, WO 95/26205, GB9624918.0; metal radionuclides, paramagnetic metal ions, fluorescent metal ions, heavy metal ions and cluster ions as described in WO 91/14460, WO 92/17215, WO 96/40287, and WO 96/22914; and U.S. Pat. No. 4,647,447, WO 89/00557, U.S. Pat. No. 5,367,080, U.S. Pat. No. 5,364,613; non-metal atomic moieties such as, e.g. $^{123}I$, $^{131}I$, and $^{18}F$, and heavy atoms such as I; organic chromophoric or fluorophoric moieties as described in Matsuoka, Topics in Applied Chemistry: Infrared absorbing dyes (1990), Waring et al., Topics in Applied Chemistry: The Chemistry and Application of Dyes (1990), "Handbook of Fluorescent Probes and Research Chemicals" Haugland, Molecular Probes Inc, 1996, DE-A-4445065, DE-A-4326466, JP-A-3/228046, Narayanan et al., J. Org. Chem. 60: 2391-2395 (1995), Lipowska et al., Heterocyclic Comm. 1: 427-430 (1995), Fabian et al., Chem. Rev. 92: 1197 (1992), WO96/23525, Strekowska et al., J. Org. Chem. 57: 4578-4580 (1992), WO (Axis) and WO 96/17628; visible dyes as described in, Waring and Hallas, The Chemistry and Application of Dyes, Topics in Applied Chemistry (1990); Haugland, Handbook of Fluorescent Probes and Research Chemicals (6th ed. 1996).

Examples of imaging modalities suitable for detecting the detectable moiety linked to the ligand include, but are not limited to, magnetic resonance, nuclear magnetic resonance, radioscintigraphy, positron emission tomography, computed tomography, near-infrared fluorescence, X-ray, ultra sound, ultraviolet light, or visible light, wherein the image of the detectable moiety is indicative of the activity of a specific extracellular protease (for example, see Dahnhert, Radiology Review Manual (4th ed. 1999); Brant et al., Fundamentals of Diagnostic Radiobiology, (2nd ed 1999); Weissleder et al., Primer of Diagnostic Imaging, (2nd ed. 1997); Buddinger et al., Medical Magnetic Resonance A Primer, Society of Magnetic Resonance, Inc. (1988); and Weissleder et al., Nature Biotech. 17: 375-378 (1999)).

Where the detectable moiety is a metal, generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight. Where the detectable moiety is a radionuclide, dosages of 0.01 to 100 mCi, preferably 0.1 to 50 mCi will normally be sufficient per 70 kg bodyweight. Where the detectable moiety is a superparamagnetic particle, the dosage will normally be 0.5 to 30 mg Fe/kg bodyweight. Where the detectable moiety is a gas or gas generator, e.g. in a microballoon, the dosage will normally be 0.05 to 100.mu. L gas per 70 kig bodyweight.

Thus, in certain circumstances, it may be desirable that the linker biodegrade after administration. By selecting an appropriately biodegradable linker it is possible to modify the biodistribution and bioelimination patterns for the ligand and/or detectable moiety. Where ligand and/or detectable moiety are biologically active or are capable of exerting undesired effects if retained after the imaging procedure is over, it may be desirable to design in linker biodegradability which ensures appropriate bioelimination or metabolic breakdown of the ligand and/or detectable moieties. Thus, a linker may contain a biodegradable function which on breakdown yields breakdown products with modified biodistribution patterns which result from the release of the detectable moiety from the ligand or from fragmentation of a macromolecular structure. By way of example for linkers which carry chelated metal ion moieties it is possible to have the linker incorporate a biodegradable function which on breakdown releases an excretable chelate compound containing the detectable moiety. Accordingly, biodegradable functions may if desired be incorporated within the linker structure, preferably at sites which are (a) branching sites, (b) at or near attachment sites for ligands or detectable moieties, or (c) such that biodegradation yields physiologically tolerable or rapidly excretable fragments.

VII. Kits

The present invention further provides kits for use within any of the above diagnostic methods. Such kits typically comprise two or more components necessary for performing a diagnostic assay. Components may be compounds, reagents, containers and/or equipment. For example, one container within a kit may contain an Apo A-I, Apo A-II, Apo A-IV, Apo E, Apo C-I, Apo C-II, Apo C-III, or serum amyloid A peptide. One or more additional containers may enclose elements, such as reagents or buffers, to be used in the assay. Such kits may also, or alternatively, contain a detection reagent as described above that contains a reporter group suitable for direct or indirect detection of antibody binding.

Kits can also be supplied for therapeutic uses. Thus, the subject composition of the present invention may be provided, usually in a lyophilized form, in a container. The Apo A-I, Apo A-II, Apo A-IV, Apo E, Apo C-I, Apo C-II, Apo C-III, and serum amyloid A polypeptides and nucleic acids described herein are included in the kits with instructions for use, and optionally with buffers, stabilizers, biocides, and inert proteins. Generally, these optional materials will be present at less than about 5% by weight, based on the amount of polypeptide or nucleic acid, and will usually be present in a total amount of at least about 0.001% by weight, based on the polypeptide or nucleic acid concentration. It may be desirable to include an inert extender or excipient to dilute the active ingredients, where the excipient may be present in from about 1 to 99% weight of the total composition. The kits may further comprise a second therapeutic agent, e.g., a statin, a bile reducing agent, or an anti-inflammatory agent.

EXAMPLES

The following examples are offered to illustrate, but not to limit the presently claimed invention.

Example 1

Materials and Methods

Synthetic Peptides—Helical peptides used in this study were composed of sequences of amino acids as found in the C-terminal domain (aa 44-243) of apoA-I using the convention of Mishra et al. (Mishra, V. K. et al., *Biochemistry*, 37:10313-10324 (1998)) to define the amphipathic α-helical segments. The following list defines the amino acid segments used to create synthetic peptides including individual 11- and 22-mer helices, unique chimeras, native helical combinations, and transposition peptides: helix 1 peptide, aa 44-65 (22-mer); helix 9, aa 209-219 (11-mer); helix 10, aa 220-241 (22-mer); 1/9 chimera, aa 44-65/209-219 (33-mer); 1/3 chimera, aa 44-65/88-98 (33-mer); 2/9 chimera, aa 66-87/209-219 (33-mer); 4/9 chimera, aa 99-120/209-219 (33-mer); the 9/10 peptide, aa 209-241 (33-mer); 10/9 transposition peptide, as 220-241/209-219 (33-mer), and 9/1, aa 209-219/44-65 (33-mer). Biosynthesis Inc (Lewisville, Tex.) synthesized the peptides. All peptides were isolated by high performance liquid chromatography and used at a purity of 95%. The peptides were synthesized with an N-terminal acetyl group and a C-terminal amide to stabilize the amphipathic α-helices (Venkatachalapathi, Y V. et al., *Protein*, 15:349-359 (1993)). Stock solutions (0.5-1 mg/ml) were prepared by dissolving the lyophilized peptides in sterile Tris-HCl (10 mM) buffered (pH 7.4) saline and stored at 4° C. Protein concentrations were set by the mass data provided by the manufacturer and were verified using a BCA reagent kit (Pierce).

Apolipoprotein A-I—A bacterial expression system was used to generate full-length apoA-I as previously described (Oda, M. N. et al., *Biochemistry*, 40:1710-1718 (2001); Bielicki, J. K and Oda, M. N., *Biochemistry*, 41:2089-2096 (2002)) using a histidine (His) tag to facilitate protein purification. The purified recombinant protein was 98% pure and exhibited a molecular mass of 28 kDa, similar to native apoA-I purified from human plasma (Oda, M. N. et al., *Biochemistry*, 40:1710-1718 (2001); Bielicki, J. K and Oda, M. N., *Biochemistry*, 41:2089-2096 (2002)). Control experiments verified that the recombinant apoA-I behaved exactly the same as native apoA-I with regard to mediating cholesterol efflux in an ABCA1-dependent manner. The present study was conducted using His-tagged apoA-I, which exhibits normal cholesterol efflux capability similar to apoA-I without a His tag.

Cellular Cholesterol Efflux Protocol—J774 macrophages were used to assess the cholesterol efflux properties of synthetic amphipathic α-helical peptides (Bielicki, J. K and Oda, M. N., *Biochemistry*, 41:2089-2096 (2002); Jia, Z. et al., *Biochem. Biophys. Res. Common.*, 297:206-213 (2002)). This cell line was chosen because cholesterol efflux can be enhanced using a cAMP analog that up-regulates ABCA1 protein expression. The cells were seeded onto 24-well culture plates and labeled for 48 h with [$^3$H]cholesterol in RPMI 1640 supplemented with 1% fetal bovine serum. The cAMP analog CPT-cAMP was added (0.3 mM, final concentration) to the cells at least 12 h before the initiation of cellular cholesterol efflux. Synthetic peptides in lipid-free form were added to cells in serum-free RPMI. The lipid-free form of full-length recombinant apoA-I was used as a positive control to define apparent ABCA1-dependent cholesterol efflux in the presence and absence of cAMP stimulation. Efflux results were expressed as a percentage of the initial cellular [$^3$H] appearing in the medium as a function of time subtracting the background efflux obtained using serum-free medium alone.

Relative Lipid Binding Affinity, Hydrophobicity, and Amphiphilicity of Synthetic Peptides—In some experiments, the relative lipid binding affinity of unique peptides was quantified using a surface balance technique (Gillotte, K L. et al., *J. Biol. Chem.*, 274:2021-2028 (1999)). For routine analyses, a turbid solution of dimyristoylphosphatidylcholine (DMPC) was used to assess the relative capacity of synthetic peptides to solubilize phospholipid as described (Palgunachari, M. N. et al., Arterioscler. Thromb. Vasc. Biol., 16:328-338 (1996); McLean, L. R. and Hagaman, K. A., *Biochim. Biophys. Acta*, 1167:289-295 (1993)). The DMPC was used at a final concentration of 0.08 mg/ml in 10 mM Tris-saline (pH 7.4). The final weight ratio of peptides relative to DMPC was 1:1. The absorbance (400 nm) of samples was monitored continuously over a period of 30 min at 25° C. Hydrophobicity of helical peptides was calculated using the consensus scale (Eisenberg D., *Annu. Rev. Biochem.*, 53:593-623 (1984)). The hydrophobic moment (kcal/mol) of synthetic peptides, which is a measure of helix amphiphilicity, was calculated as described by Eisenberg et al. (Eisenberg, D. et al., *Nature*, 299:371-374 (1982)).

ABCA1 Stabilization—J774 macrophages were used to assess relative ABCA1 protein levels in the presence and absence of synthetic peptides. Cells were grown in 10% fetal bovine serum, extensively rinsed, and incubated (18 h) with Dulbecco's modified Eagle's medium containing 0.1% bovine serum albumin plus the cAMP analog 8-bromo-cAMP. Cells were next exposed to synthetic peptides or serum-free medium in the absence of the cAMP stimulus to evaluate whether ABCA1 protein was stabilized or degraded. Relative levels of ABCA1 protein were assessed by immunoblot analysis of cell membranes (Oram, J. F. et al., *J. Biol. Chem.*, 278:52379-52385 (2003)). ABCA1 was visualized using an enhanced chemiluminescence detection assay.

Example 2

Cholesterol Efflux Capability of a Synthetic Peptide Based on Helix 1 of ApAI

Helix 1 has high lipid binding affinity; thus, we asked whether a synthetic peptide (22-mer) corresponding to helix 1 of apoA-I promoted cholesterol efflux in an ABCA1-dependent manner using J774 macrophages. The 22-mer helix 1 peptide failed to stimulate ABCA1-dependent cholesterol efflux (FIG. 1A). Cholesterol efflux from cAMP-treated and -untreated cells was equivalent in contrast to the efflux obtained with full-length apoA-I, which increased dramatically upon the up-regulation of the ABCA1 transporter (FIG. 1B). At relatively high concentrations of the helix 1 peptide (i.e. 75 μg/ml), cholesterol efflux was only 15% that obtained with full-length apoA-I using cAMP-treated macrophages (FIG. 1C). These results indicate that the high lipid binding affinity associated with helix 1 was not sufficient to stimulate cholesterol efflux via the ABCA1 transporter.

Example 3

Cholesterol Efflux Properties of Apo AI Helix 1/9 Chimeric Peptide

The results presented in FIG. 1 showing that helix 1 was a poor mediator of cholesterol efflux suggests that several amphipathic α-helices in tandem may create a structural element that stimulates cellular cholesterol efflux via the ABCA1 transporter. Thus, we sought to identify the minimum sequence requirements that endowed cholesterol efflux capability. To this end, we asked whether the addition of the 11-mer helix 9 (aa 209-219) to helix 1 produced an increase in cholesterol efflux. A 33-mer peptide composed of helices 1 plus 9 (1/9 chimera) stimulated cholesterol efflux in the absence and presence of CAMP stimulation similar to full-length apoA-I (FIG. 2A). Cholesterol efflux was dependent on the concentration of the 1/9 chimera reaching maximal levels at 50 μg/ml (FIG. 2B). Helix 9 alone (11-mer peptide) failed to stimulate ABCA1-dependent cholesterol efflux (FIG. 2C) similar to a peptide based on helix 1 (FIG. 1A). Exposure of J774 macrophages concurrently to both helix 9 and helix 1 (not covalently linked) did not stimulate cholesterol efflux, indicating that the two helices needed to be joined to mediate cholesterol efflux via ABCA1.

The results presented in FIG. 2 imply that the joining of helices 1 and 9 brought together key determinants that enabled the 33-mer peptide to stimulate cellular cholesterol efflux via ABCA1. However, this joining did not alter the lipid binding affinity compared with helix 1 alone (22-mer), as measured using a surface balance technique (summarized in Table I). The lipid binding affinities of helix 1, the 1/9 chimera, and full-length apoA-I were identical (Bielicki, J. K and Oda, M. N., *Biochemistry*, 41:2089-2096 (2002); Jia, Z. et al., *Biochem. Biophys. Res. Common.*, 297:206-213 (2002); and McLean, L. R. and Hagaman, K. A., *Biochim. Biophys. Acta*, 1167:289-295 (1993)±1 dynes/cm, respectively). The 1/9 chimera was slightly more hydrophobic compared with helix 1, but the amphiphilicity (i.e. hydrophobic moment) of the two peptides was nearly the same (Table I). Both the 1/9 chimera and the helix 1 peptide cleared a turbid solution of DMPC in a similar manner (summarized in Table I). Collectively, these results indicate that the ability of the 1/9 chimera to mediate cholesterol efflux in an ABCA1-dependent manner was not the result of an increase in lipid binding affinity created by the joining of the two helical segments.

TABLE I

Biophysical properties of amphipathic helical peptides derived from human apoA-I

| Helical peptide | No. of residues[a] | Hydrophobicity[b] kcal/mol | Hydrophobic moments[c] kcal/mol | Net charge[d] | Monolayer exclusion pressure dynes/cm | DMPC clearance |
|---|---|---|---|---|---|---|
| 10 | 22 | 0.097 | 0.20 | 0 | 28 | + |
| 9/10 | 33 | 0.106 | 0.19 | −1 | 36 | + |
| 10/9 | 33 | 0.106 | 0.22 | −1 | ND[e] | + |
| 9 | 11 | 0.125 | 0.25 | −1 | ND | − |
| 1/9 | 33 | 0.169 | 0.21 | −1 | 31 | + |
| 9/1 | 33 | 0.169 | 0.15 | −1 | ND | + |
| 1 | 22 | 0.191 | 0.19 | 0 | 30 | + |
| 1/3 | 33 | 0.232 | 0.14 | 0 | ND | − |
| 2/9 | 33 | 0.236 | 0.25 | −5 | 19 | − |
| 2 | 22 | 0.292 | 0.25 | −4 | 17 | − |
| 4/9 | 33 | 0.292 | 0.25 | −3 | ND | + |
| 3 | 11 | 0.372 | 0.25 | 0 | ND | − |
| 4 | 22 | 0.376 | 0.25 | 2 | 20 | − |

[a]The peptides are based on amphipathic α-helices of apoA-I as described under "Experimental Procedures" and are listed in order of decreasing hydrophobicity (helix 10 is the most hydrophobic) as shown in the third column.
[b]Calculated using the consensus scale (Eisenberg D., Annu. Rev. Biochem., 53:593-623 (1984)).
[c]The helical hydrophobic moment is a measure of amphiphilicity and was calculated as described (Eisenberg, D. et al., Nature, 229:371-374 (1982)).
[d]Net charge at pH 7.4.
[e]<ND, not determined.

Example 4

Figure 3C:
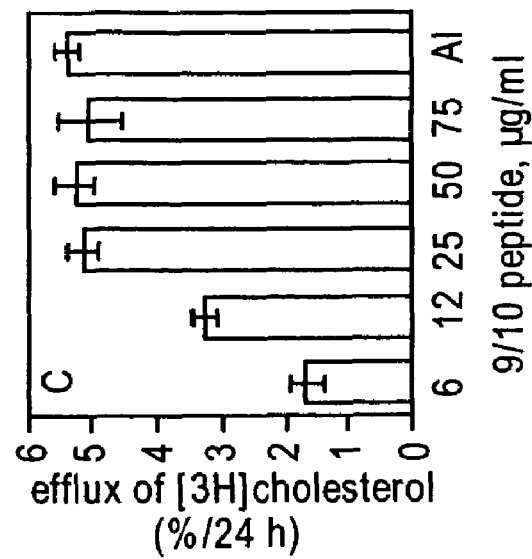
FIG. 3 illustrates data demonstrating that a 33-mer peptide composed of helices 9 and 10 of apoA-I mediates cholesterol efflux via ABCA1. Panels A and B, J774 macrophages were incubated with (circles) and without (squares) a cAMP analog as described in FIGS. 1 and 2. Panel A, cholesterol efflux mediated by a 22-mer peptide based on helix 10 (aa 220-241) of apoA-I used in lipid-free form at a concentration of 100 µg/ml. Results are representative of at least two independent experiments performed in triplicate. Panel B, the ability of a 33-mer (100 µg/ml) composed of helices 9 and 10 to stimulate cholesterol efflux. Panel C, dependence of cholesterol efflux on the concentration of the 9/10 helical peptide. Shown are the results using cAMP-treated J774 cells. Values shown are the means±S.D., n=3.
Figure 3B:
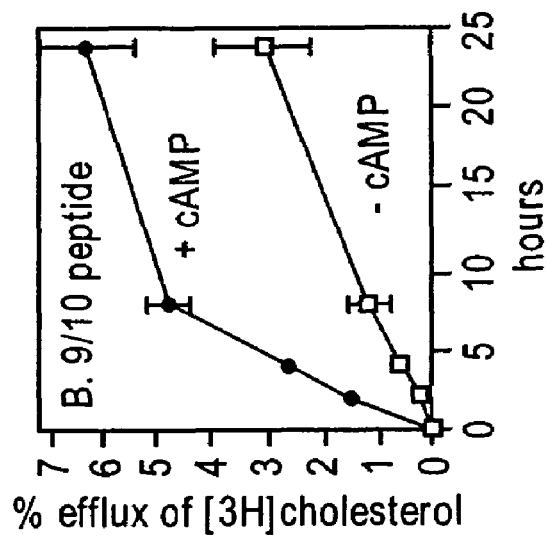
Figure 3A:
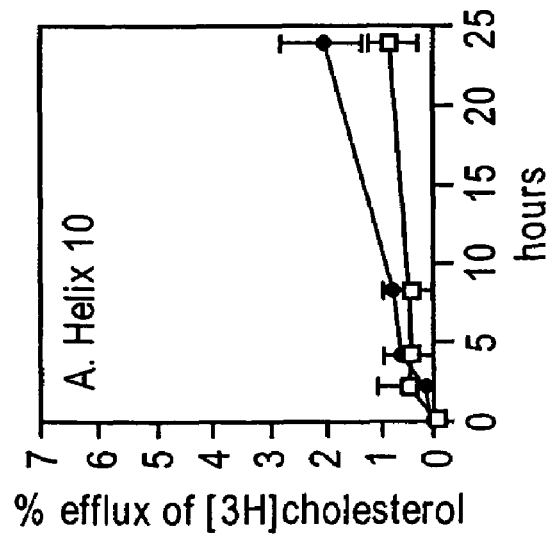

Cholesterol Efflux Properties of Apo AI Helix 10 Peptide and Helix 9/10 Peptide Helix 10 (aa 220-241) is the most hydrophobic helical segment of apoA-I (Table I), but a synthetic 22-mer peptide based on helix 10 was a poor mediator of cellular cholesterol efflux when used at a high concentration of 100 μg/ml (FIG. 3A). In contrast, a 33-mer peptide composed of apoA-I helices 9 and 10 stimulated cholesterol efflux in an ABCA1-dependent manner (FIG. 3B). Maximal levels of cholesterol efflux from CAMP-treated cells were observed at 25 μg/ml 9/10 helical peptide, suggesting that this 33-mer peptide is more efficient than the 1/9 chimera (FIG. 2B versus 3C). Apo A-I stimulated cholesterol efflux to maximal levels at a concentration of 10 μg/ml, indicating that the 9/10 peptide was less efficient than the full-length apoA-I. Helix 10 and the 9/10 peptide cleared a turbid solution of DMPC in a similar manner, consistent with their predicted hydrophobicity and hydrophobic moments, which did not differ between the two peptides (Table I). The monolayer exclusion pressure was slightly higher for the 9/10 helical peptide compared with helix 10 alone and the 1/9 chimera (Table I). This may account for the observation that the 9/10 helical peptide was 2-fold more potent than the 1/9 chimera in mediating ABCA1-dependent cholesterol efflux (FIGS. 2B versus 3C).

Example 5

Structure of Apo AI Helix 1/9 Chimeric Peptide and Helix 9/10 Peptide

Figure 4A:
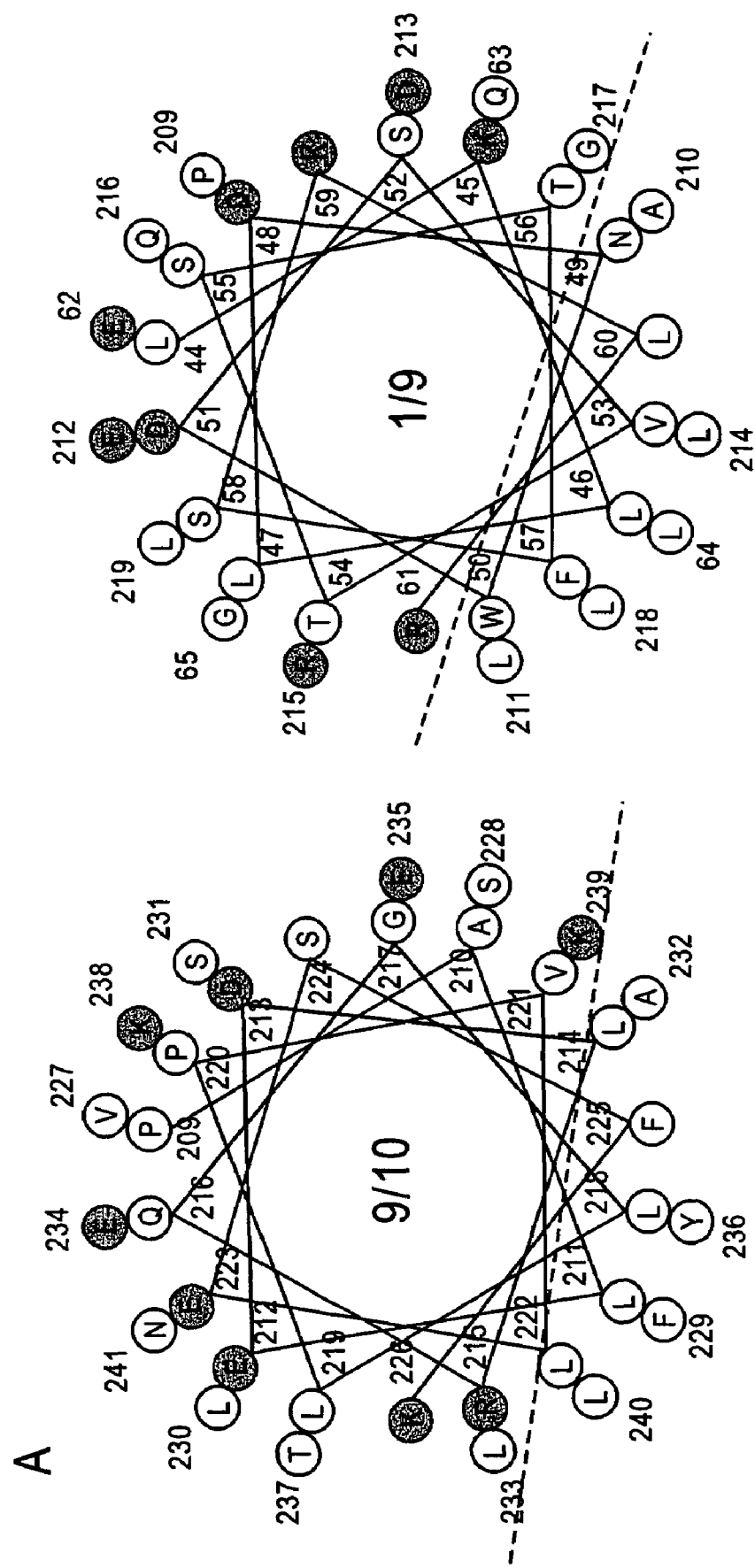
FIG. 4 illustrates the structural similarities between the 9/10 helical peptide and the 1/9 chimera. Panel A, Edmundson helical wheel projections showing the 9/10 peptide (SEQ ID NO:35) and 1/9 chimera (SEQ ID NO:37). Shaded circles represent negatively charged residues, and partially shaded circles positively charged amino acids. Dashed lines mark the lipid-water interface of the α-helices. Panel B, α-helices (SEQ ID NOS:35 and 37) are shown as cylinders cut down the long axis of the polar face and flattened. Arrows in all panels show the position of negatively charged residues that form an alignment spanning 32 Å down the length (5-6 turns) of the joined segments.

FIG. 4 illustrates the similarities and differences in the amino acid sequence and structures of the 1/9 and 9/10 helical combinations. Each of the structures consists of 33 amino acids, but the arrangement of the 11- and 22-mer helical segments differ between the 1/9 and 9/10 helical peptides (FIG. 4). Both helical peptides possess amphipathic character with positively charged residues located at the lipid-water interface of the helical structures (FIG. 4A). The 9/10 peptide exhibits class Y structure attributed to Lys-238 at the apex of the helical wheel projection; the 1/9 structure, on the other hand, more closely resembles a class A helix in which the positively charged residues are positioned toward the lipid-water interface. The latter suggests that class Y structure attributed to the specific location of a positively charged residue in the middle of the polar surface of an amphipathic α-helix is not required for mediating cholesterol efflux via ABCA1.

Despite the difference in the distribution of positively charged residues, the net charge of the 1/9 chimera is the same as the 9/10 helical combination (Table I). In addition, the position of negatively charged residues down the length of the joined helical segments is nearly identical for the structures created by the 1/9 and 9/10 helical combinations, as noted in the cylindrical diagrams (FIG. 4B). Three of these negatively charged residues form an alignment spanning ~32 Å down the length of the joined helices (arrows in FIG. 4B). These similarities on the polar surface in addition to high lipid binding affinity (Table I) may explain why the 1/9 helical peptide mediated ABCA1-dependent cholesterol efflux in a manner not unlike that of the 9/10 helical peptide.

Example 6

Specificity of Cholesterol Efflux for Apo AI 1/9 Chimeric Peptide

Figure 5B:
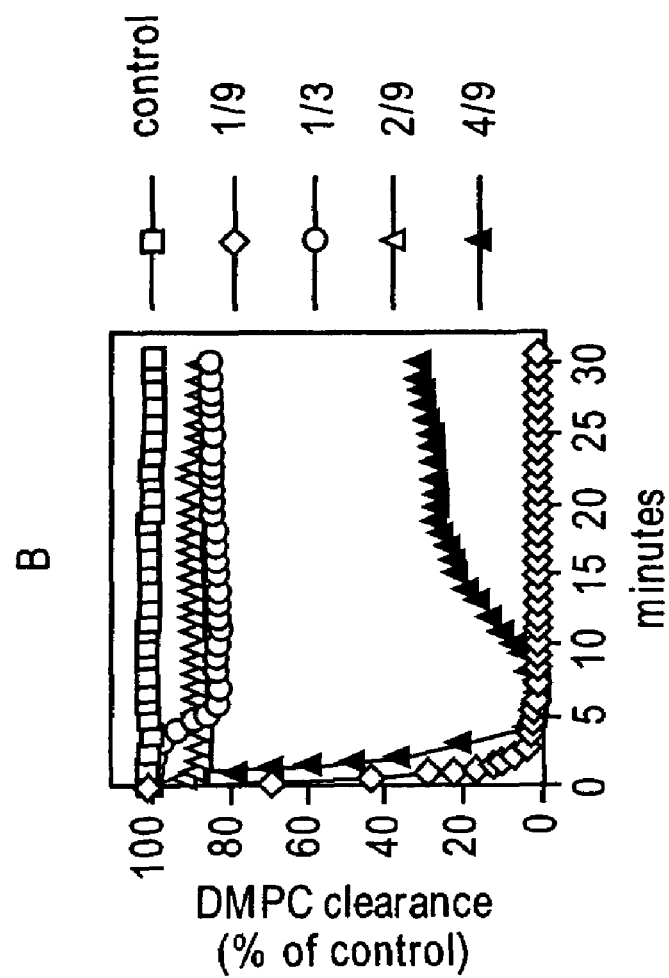
FIG. 5 illustrates data demonstrating the cholesterol efflux properties, DMPC clearance, and structures of various chimeric peptides derived from apoA-I amphipathic α-helices. Panel A, cholesterol efflux experiments using J774 macrophages incubated with (dark bars) and without (open bars) a cAMP analog as described in FIGS. 1 and 2. Panel B, DMPC clearance assays with the chimeras; control indicates no peptides added. Results are representative of three experiments. Panel C, Edmundson helical wheel projections showing the structure of the various chimeras (SEQ ID NOS:42-44). The dashed line corresponds to the lipid-water interface of the amphipathic α-helices. Panel D, amphipathic α-helical peptides (SEQ ID NOS:42-44), shown as cylinders cut down the long axis of the polar face and flattened. Shaded circles correspond to negatively charged amino acids, and partially shaded circles correspond to positively charged residues.
Figure 5A:
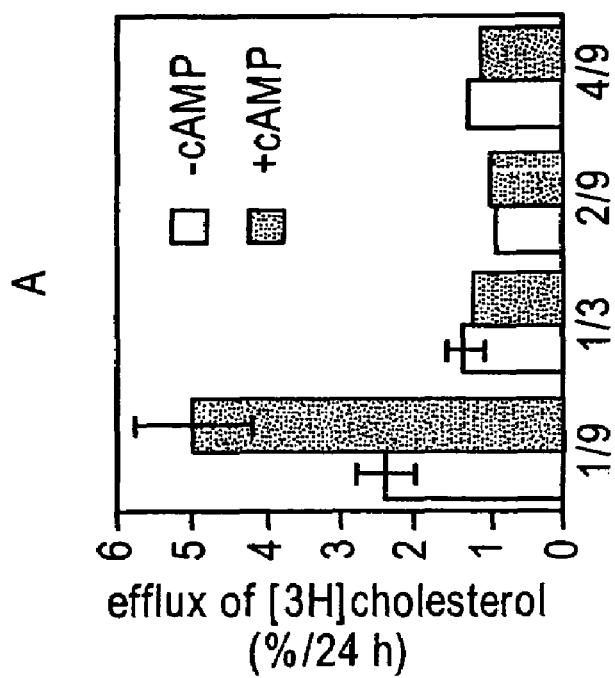
Figure 5C:
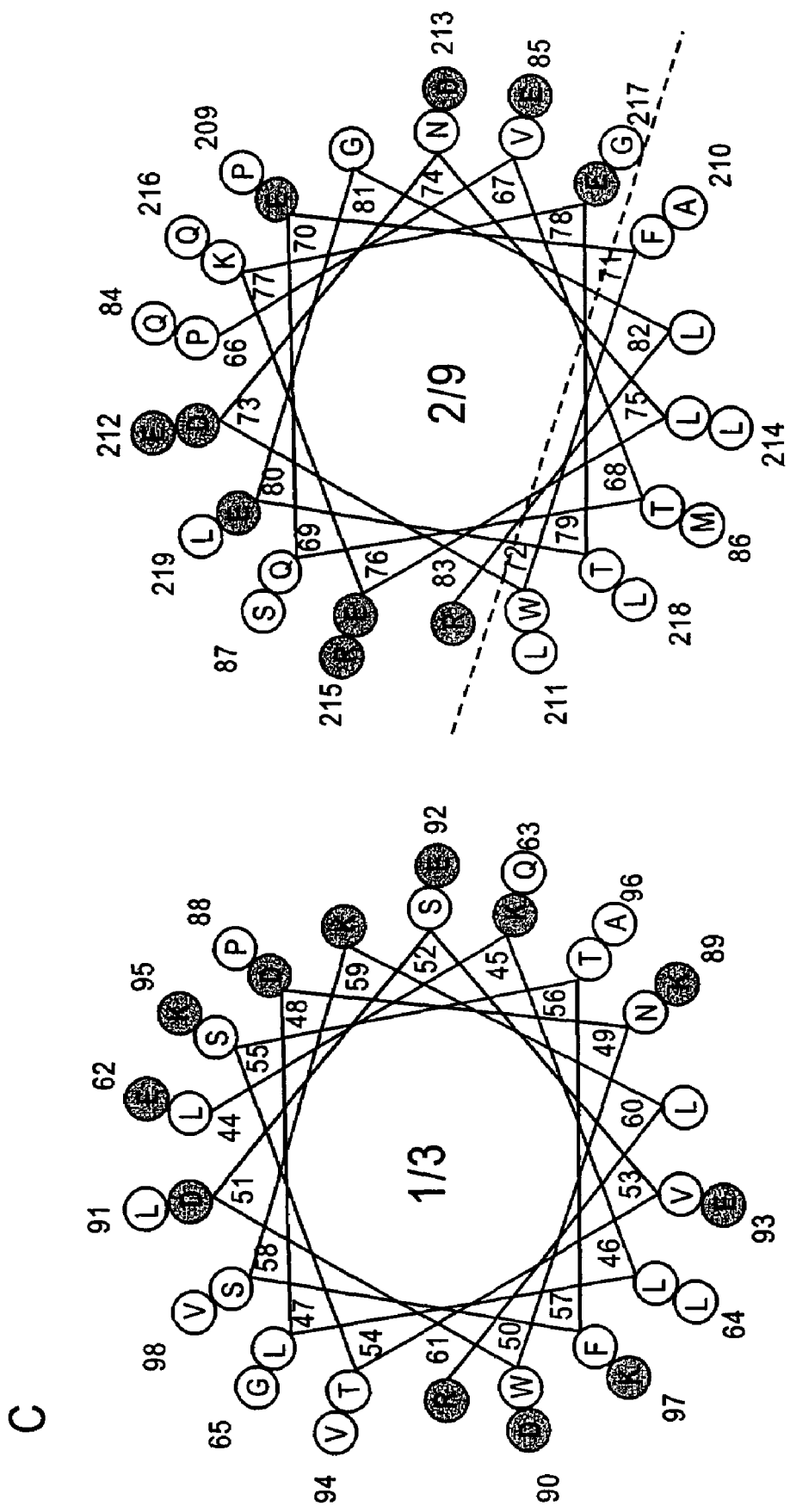
Figure 5C:
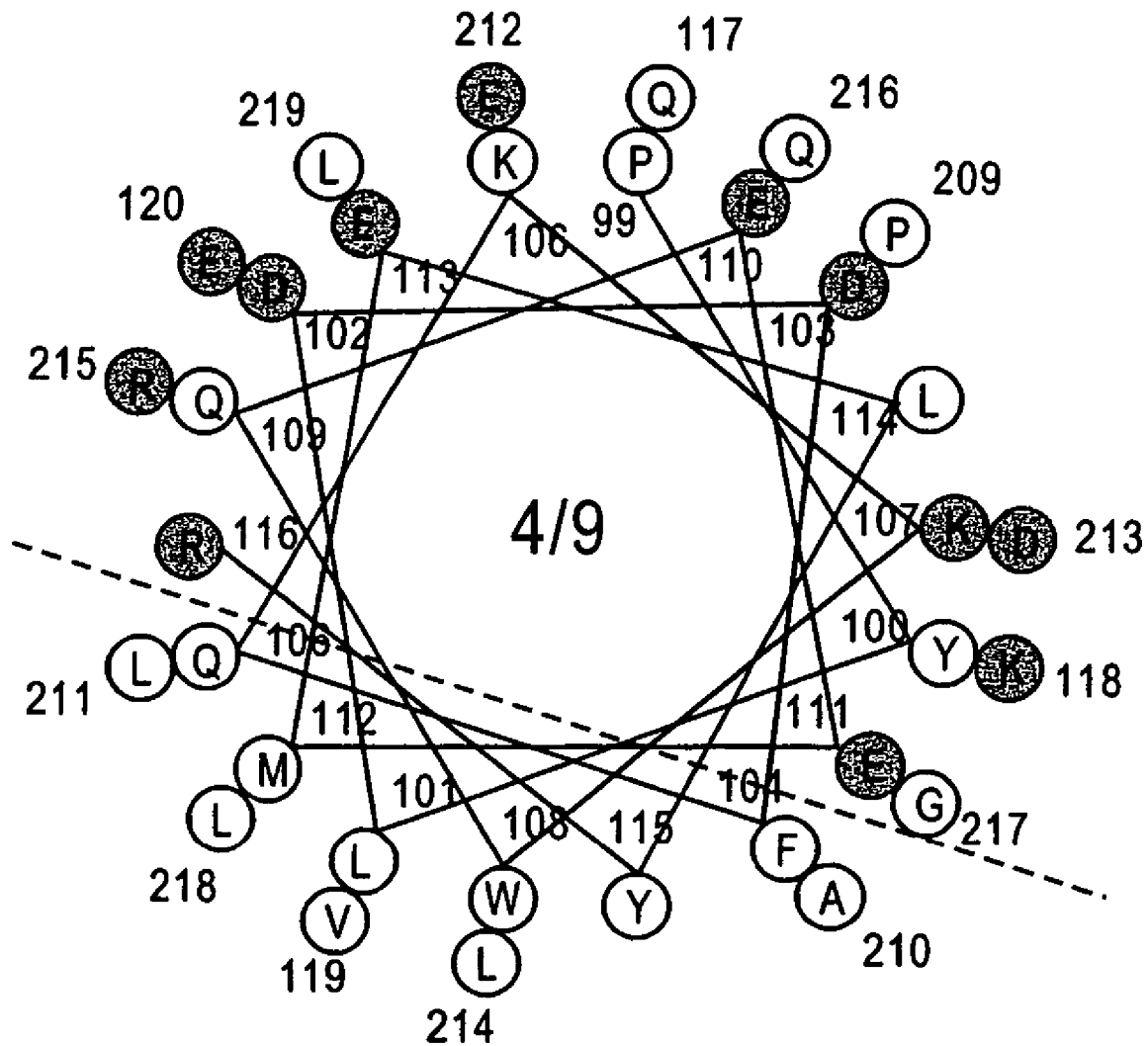

To evaluate whether the cholesterol efflux capability of the 1/9 chimera was dependent specifically on the presence of helix 9, this 11-mer segment was replaced with helix 3, which represents the other 11-mer helix present within the C-terminal domain of apoA-I. The resulting 1/3 chimera failed to mediate cellular cholesterol efflux in an ABCA1-dependent manner, indicating that helix 9 was unique and critical to the cholesterol efflux properties of the 1/9 peptide (FIG. 5A). The 1/3 chimera also poorly solubilized a turbid solution of DMPC (FIG. 5B and Table I). Edmundson helical wheel projections of the 1/3 chimera revealed that this combination exhibited a narrow hydrophobic surface as polar residues were dispersed around most of the structure (FIG. 5C). This is in keeping with the low amphiphilicity (i.e. hydrophobic moment) of the 1/3 chimera as shown in Table I. These results indicate that a 33-mer chimera with relatively low lipid binding affinity and poor amphipathic character is not able to mediate cellular cholesterol efflux in an ABCA1-dependent manner.

Similar helix replacement experiments were conducted utilizing various 22-mer repeats in place of helix 1. A 33-mer chimera composed of helices 2 and 9 (2/9) failed to stimulate ABCA1-dependent cholesterol efflux (FIG. 5A) even though the chimera possessed an alignment of negatively charged residues on its polar surface similar to 1/9 and 9/10 helical peptides (FIG. 5D). The 2/9 chimera possessed amphipathic character (FIG. 5C), but the net charge of the peptide was –5, and the peptide poorly solubilized DMPC (FIG. 5B), consistent with its calculated hydrophobicity (Table I). These results support the premise that relatively good lipid-binding affinity is an important factor for mediating cholesterol efflux via ABCA1. A 33-mer chimera composed of helices 4 and 9 (4/9) also failed to mediate ABCA1-dependent cholesterol efflux (FIG. 5A). However, the 4/9 chimera was found to possess relatively good lipid binding affinity as judged by a DMPC clearance assay (FIG. 5B). The polar surface of the 4/9 chimera was found to be somewhat different compared with that of the 1/9 and 9/10 helical peptides, with positively charged amino acids inserted between negatively charged residues that span the length of the 4/9 helical peptide. These findings support the premise that lipid binding affinity alone is not sufficient to stimulate cholesterol efflux. Factors in addition to lipid binding affinity (i.e. DMPC clearance capability) appear also to be important for a 33-mer helical peptide to mediate cholesterol efflux via ABCA1.

Example 7

Cholesterol Efflux Capability of Apo AI 10/9 and 9/1 Chimeric Peptides

Figure 6C:
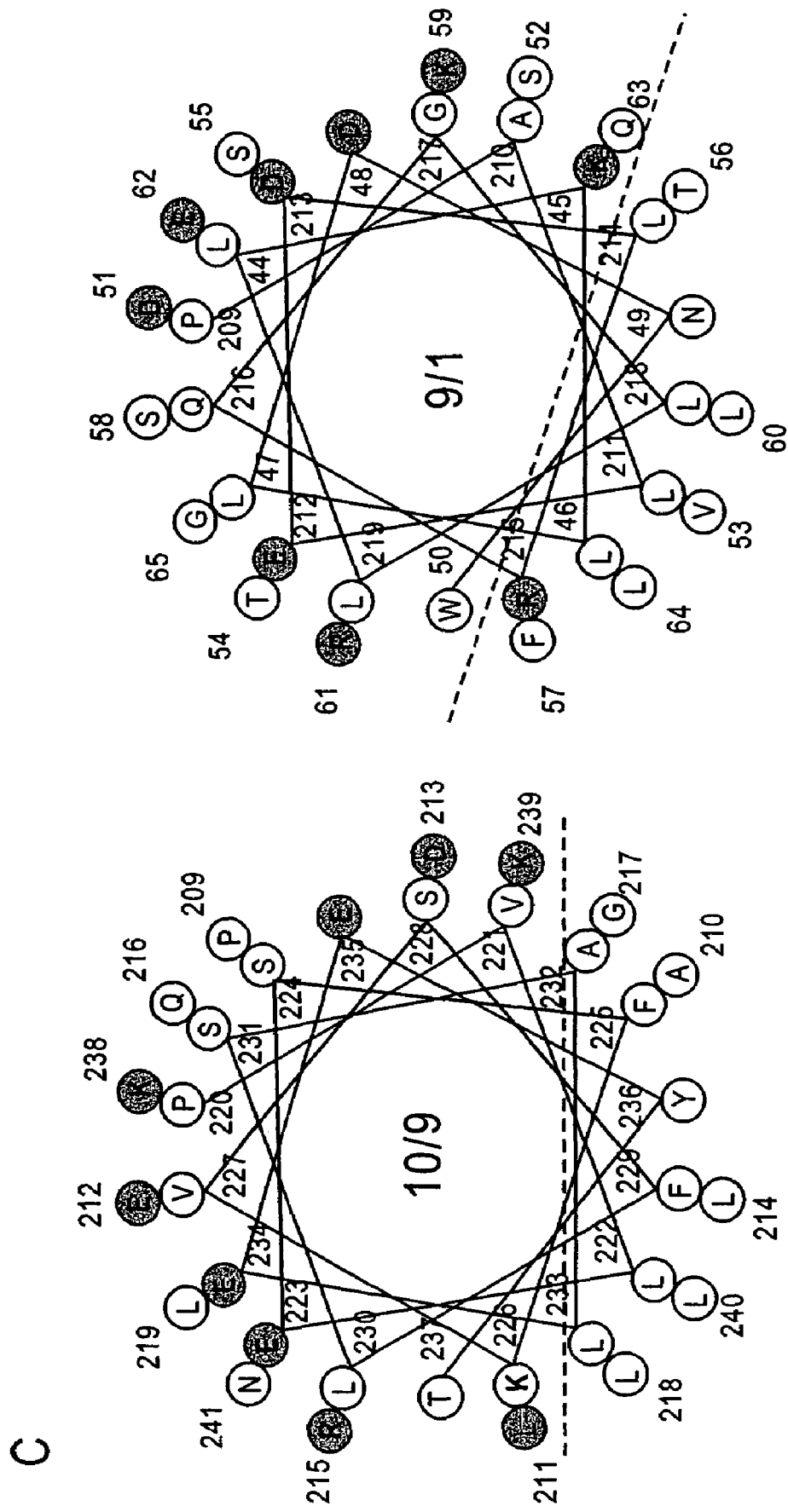
FIG. 6 illustrates data demonstrating the cholesterol efflux properties of 10/9 and 9/1 transposition peptides. Panel A, J774 macrophages were incubated with (dark bars) and without (open bars) a cAMP analog to up-regulate ABCA1 protein. The ability of transposition peptides 10/9 and 9/1 to stimulate cholesterol efflux is shown. Each peptide was used in lipid-free form at a concentration of 50 µg/ml. Panel B, dependence of cholesterol efflux on the concentration of 10/9 and 9/1 helical peptides. Results are representative of two identical experiments; shown are the results from cAMP-treated cells. Panel C, Edmundson helical wheel projections showing the amphipathic structure of the 10/9 (SEQ ID NO:45) and 9/1 (SEQ ID NO:41) peptides. Panel D, cylindrical diagrams showing the relative positions of amino acids along the α-helices (SEQ ID NOS:45 and 46). Shaded circles highlight the negatively charged residues, and partially shaded circles high-light the positively charged amino acids. The 9/1 peptide was engineered with a proline in place of Leu-44, in keeping with the other 33-mers used in this study.
Figure 6D:
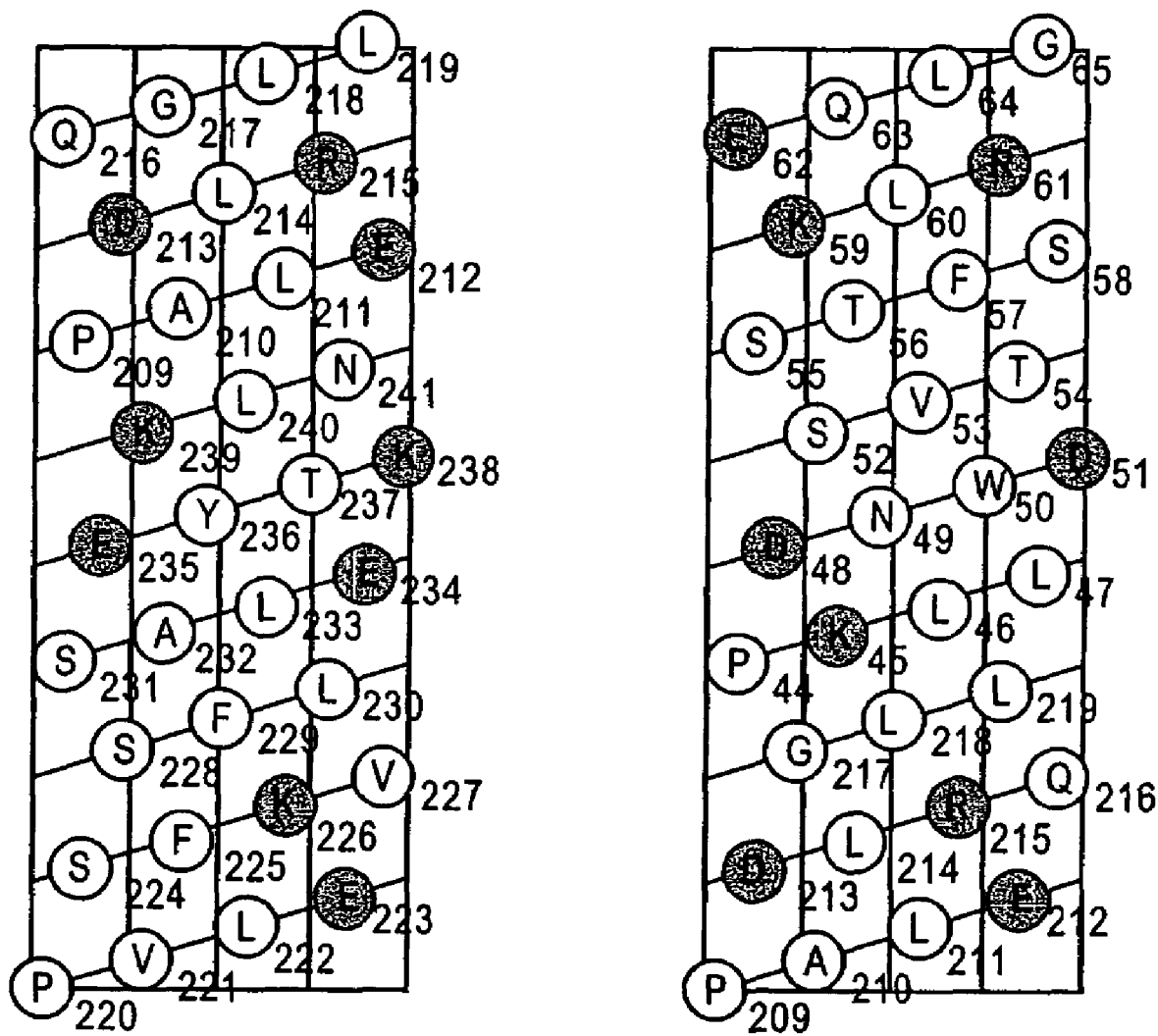

To gain additional insights into the structural determinants that are important for mediating cholesterol efflux via ABCA1, we transposed helices 9 and 10 to create a 10/9 synthetic peptide. This transposition strategy introduces a positively charged residue (Lys-238) into the alignment of negatively charged amino acids formed along the length of the joined 10 plus 9 helical segments, analogous to the structure created by the 4/9 chimera (FIG. 5D). The 10/9 transposition peptide failed to stimulate ABCA1-dependent cholesterol efflux (FIG. 6, A and B) despite the fact that the peptide exhibited class Y structure as well as the same hydrophobicity and amphiphilicity as the native 9/10 helical combination (Table I). The 10/9 peptide effectively cleared a turbid solution of DMPC as indicated in Table I. In contrast, a transposition peptide consisting of helices 9 and 1 (9/1 peptide) stimulated cholesterol efflux in an ABCA1-dependent manner (FIG. 6, A and B). This is consistent with the structure shown in FIG. 6D whereupon transposing helices 1 and 9 created a new alignment of negatively charged residues (Glu-62, Asp-48, Asp-51, and Asp-213) not interrupted by positively charged residues. The alignment of negatively charged amino acids within the 9/1 transposition peptide includes residue Asp-51, positioned 360 degrees and 5 helical turns from Pro-209 (FIG. 6, C and D). These observations support the premise that the topography of negatively charged residues on the polar surface of a 33-mer helical peptide is an important determinant endowing the peptide with cholesterol efflux activity.

Example 8

Truncated Apo A-I Mediates Cholesterol Efflux

Figure 7A:
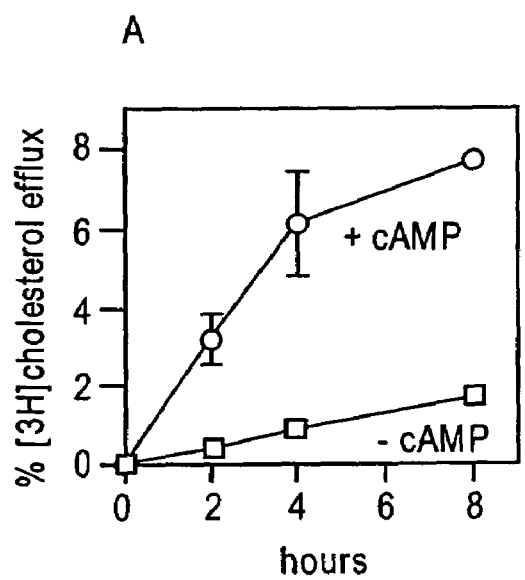
FIG. 7 illustrates data demonstrating that cholesterol efflux is mediated by the Apo A-I deletion mutant A-I Δ1-59/Δ185-243. Panel A, J774 macrophages were treated with (circles) and without (squares) a cAMP analog. The truncated apoA-I variant was subsequently added to cells in lipid-free form at 50 µg/ml. The percent efflux of cholesterol is shown. Values are means±SD, n=3. Panel B, Helical net diagram depicting helices 6 & 7 of apoA-I (SEQ ID NO:47). Shaded circles denote acidic residues and partially shaded circles basic amino acids. The small numbers refer to the primary amino acid sequence as found in full-length apoA-I. The arrows mark the acidic residues that form an alignment implicated in mediating ABCA1-dependent cholesterol efflux.

The underlying basis by which various truncated forms of apoA-I mediate ABCA1-dependent cholesterol efflux is not known (see, e.g., Panagotopulos et al., *J. Biol. Chem.* 277: 39477-39484 (2002) and Chroni et al., *J. Biol. Chem.* 278: 6719-673022 (2003)). We addresses this question with the objective of defining the determinants present within apoA-I central helices that confer cholesterol efflux capability. Consistent with previous reports, the A-I Δ1-59/Δ185-243 helix-deletion variant stimulates cholesterol efflux in a manner consistent with the involvement of ABCA1. This data is shown in FIG. 7A.

Figure 7B:
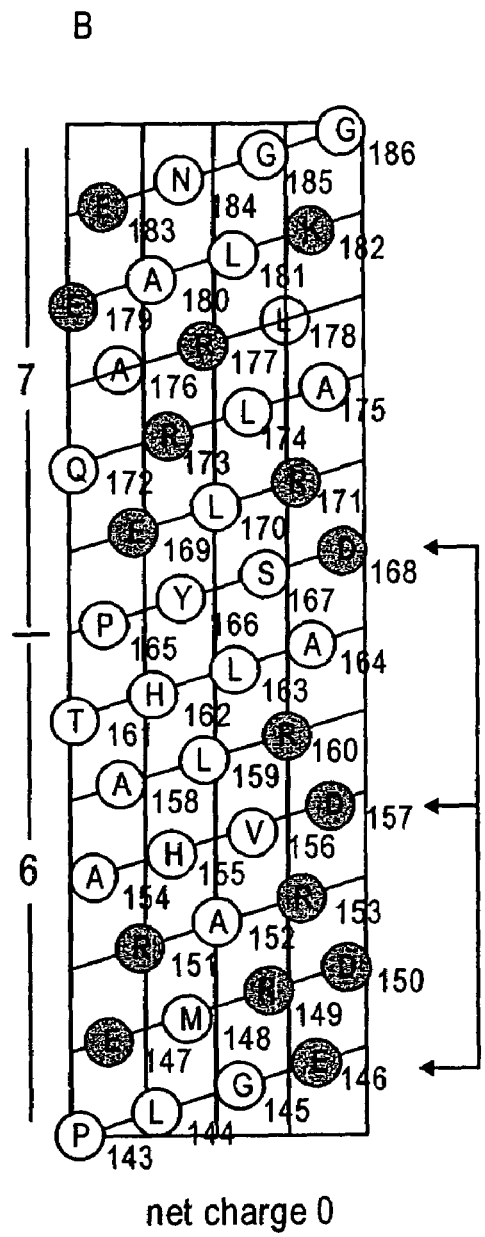

Helical net diagrams were constructed to determine if specific helical combinations that comprise A-I Δ1-59/Δ185-243 displayed an alignment of acidic residues. We reasoned that if an alignment of acidic residues was important for cholesterol efflux, then our analyses would reveal potential candidate segments that warrant further study. As can be seen in FIG. 7B, the 6 plus 7 helical combination within this variant exhibits an alignment of acidic residues similar to that of the 9/10 helical combination where three negatively charged amino acids align across six helical turns. This suggests that seemingly distinct apoA-I α-helices may share a common mechanistic basis for mediating ABCA1-dependent cholesterol efflux.

Example 9

The C-Terminal of Apo E Mediates Cholesterol Efflux

Consistent with the idea that the topography of acidic residues is important for cholesterol efflux, the C-terminal domain of apoE was found to be a potent stimulator of cholesterol efflux in a manner consistent with the involvement of ABCA1. This data is shown in FIG. 8A. In contrast, the N-terminal four-helix bundle was poorly active. The N-terminal domain used in these studies was derived from apoE3, which possesses a cysteine residue at position 112. Studies employing reduced and oxidized forms of the N-terminal domain indicated that both failed to mediate ABCA1-dependent cholesterol efflux, revealing that both the monomeric and dimeric forms of the N-terminal domain were poor mediators of cellular cholesterol efflux. Studies of apoE4 corroborate this where the NT four-helix bundle (lacks cysteine) was not able to mediate ABCA1-dependent cholesterol efflux. We also noted that the CT domain was more effective than full-length apoE3 in mediating cholesterol efflux, suggesting that there may be some beneficial attributes associated with the CT domain useful for designing therapeutics that stimulate ABCA1-dependent cholesterol efflux. This data is shown in FIG. 8A.

Our studies utilizing the entire CT domain suggest that it possesses an α-helical segment that is responsible for stabilizing ABCA1 and mediating cellular cholesterol efflux. The CT domain of apoE is composed of two, long helical stretches separated via a proline residue. The first segment consists of 51 amino acids (residues 216-266) and the second 33 residues (aa267-299). The former is Class A and the latter Class G with negative residues located at the lipid-water interface and positive residues toward the middle of polar surface. An alignment of acidic residues is prominently displayed within the Class A segment within the CT domain stretching 33 amino acids (see, FIG. 8B), suggesting that it corresponds to the element that is responsible for mediating cholesterol efflux via the ABCA1 pathway. This will be tested in the proposed studies employing a synthetic 33-mer helical peptide based on this Class A helix (aa216-248) in conjunction with a peptide based on the Class G helix (267-299) that forms the remainder of C-terminus. The alignment of acidic residues spanning aa 216-248 of apoE appears to be enriched in acidic residues as shown in FIG. 9B. This could account for our observation that the CT domain is a potent stimulator of ABCA1-dependent cholesterol efflux when used outside the context of the full-length molecule (see, FIG. 8A). In addition, acidic residues form an alignment over the first 22 amino acids of this segment, where each acidic residue is separated from one another by two helical turns instead of three.

Example 10

Figure 9:
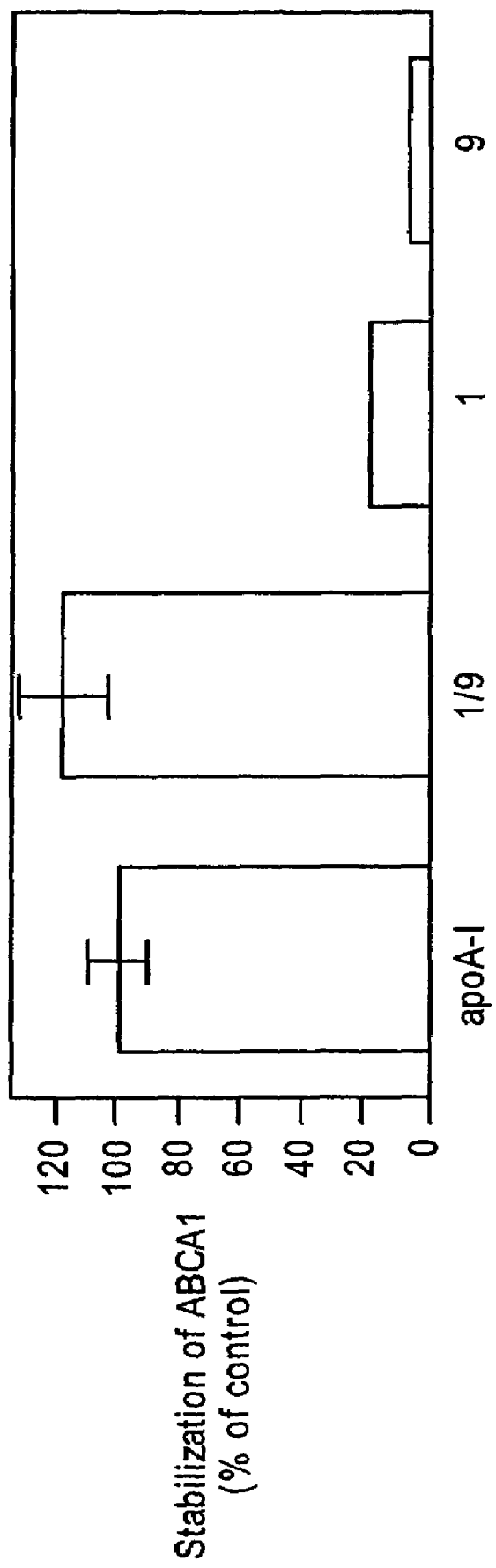
FIG. 9 illustrates data demonstrating that the chimeric peptide comprising helices 1/9 of Apo A-I stabilizes cellular ABCA1 protein. J774 macrophages were incubated (18 h) with 0.5 mM 8-bromo-cAMP in medium containing 0.1% bovine serum albumin to up-regulate ABCA1 protein expression. Washed cells were subsequently exposed for 6 h to bovine serum albumin medium with (+) or without (−) 8-bromo-cAMP and the indicated synthetic peptides (20 µg/ml). None refers to no peptides. The cellular membrane content of ABCA1 protein was measured by immunoblot analysis.

A Chimeric Peptide Comprising Helix 1 and Helix 9 of Apo A-I Linked in Order Stabilizes the ABCA1 Transporter To assess ABCA1 stabilization, J774 macrophages were treated with a cAMP analog to up-regulate ABCA1 protein expression and then incubated for 6 h without cAMP. In the absence of inducer, ABCA1 protein is rapidly degraded in these cells (FIG. 9). Peptides based on individual 11- and 22-mer helical segments including helices 1, 9, and 10 failed to prevent ABCA1 degradation, providing evidence that high lipid binding affinity alone is not sufficient to stabilize the ABCA1 transporter (FIG. 9). In contrast, at 20 µg/ml the 1/9 chimera and the 9/10 helical peptides stabilized cellular ABCA1 protein to levels comparable with those observed when cells were exposed continuously to cAMP (FIG. 9). Detailed concentration dependence studies revealed that the 1/9 and 9/10 helical peptides prevented ABCA1 degradation at concentrations as low as 10 µg/ml, similar to full-length apoA-I. In keeping with the results of the cholesterol efflux studies, the 10/9 transposition peptide failed to prevent ABCA1 degradation, whereas the 9/1 transposition retained ABCA1 stabilization activity (FIG. 9). Thus, it appears that the helical combinations that stimulate cholesterol efflux also stabilize the ABCA1 transporter. This data demonstrates that a peptide modified to comprise an alignment of acidic residues stabilizes ABCA1.

Example 11

Figure 10:
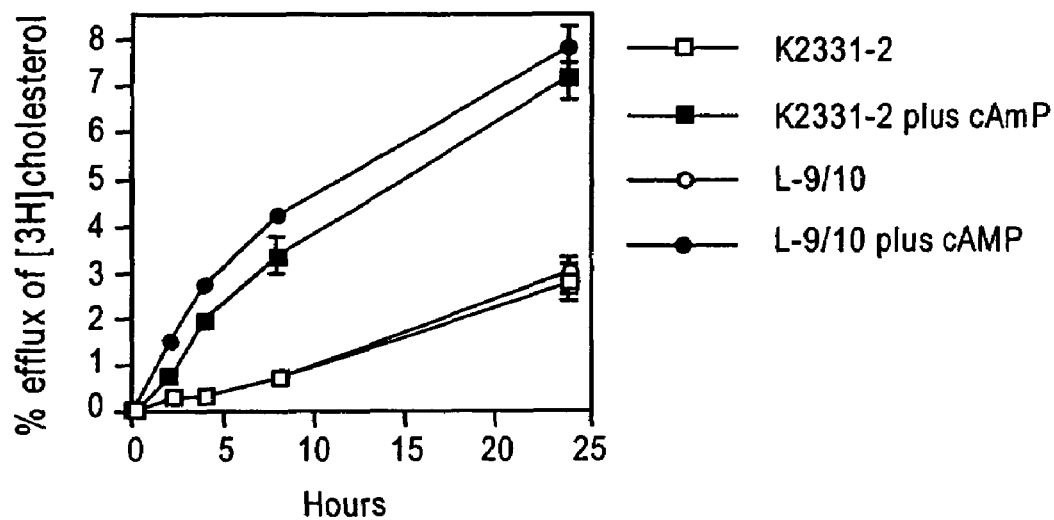
FIG. 10 illustrates demonstrating that a peptide derived from helix 10 of Apo A-I with an additional acidic residue has cholesterol efflux capability. A peptide derived from helix 10 was designed with an additional acidic residues to endow cholesterol efflux capability. The data demonstrate that a 26-mer peptide with an alignment of acidic residues down the long axis of a helical peptide can mediate cellular cholesterol efflux via ABCA1.

A Peptide Derived from Helix 10 of Apo A-I with an Additional Acidic Residue has Cholesterol Efflux Capability Helix 10 (aa220-241) of apoA-I (22-mer) of apoA-I does not mediate ABCA1-dependent cholesterol efflux nor does it stabilize ABCA1. A peptide derived from helix 10 was designed with an additional acidic residues to endow cholesterol efflux capability. The sequence of this peptide (26-mer) is as follows: PVLESFKVSFLSALEEYKTKLESALN (SEQ ID NO:2). Cholesterol efflux studies demonstrate that the peptide has a comparable cholesterol efflux activity to the native Apo AI 9/10 (33mer) peptide. The data demonstrate that a 26-mer peptide with an alignment of acidic residues down the long axis of a helical peptide can mediate cellular cholesterol efflux via ABCA1. The results are shown in FIG. 10.

Example 12

Figures 11A, 11B, 11C:
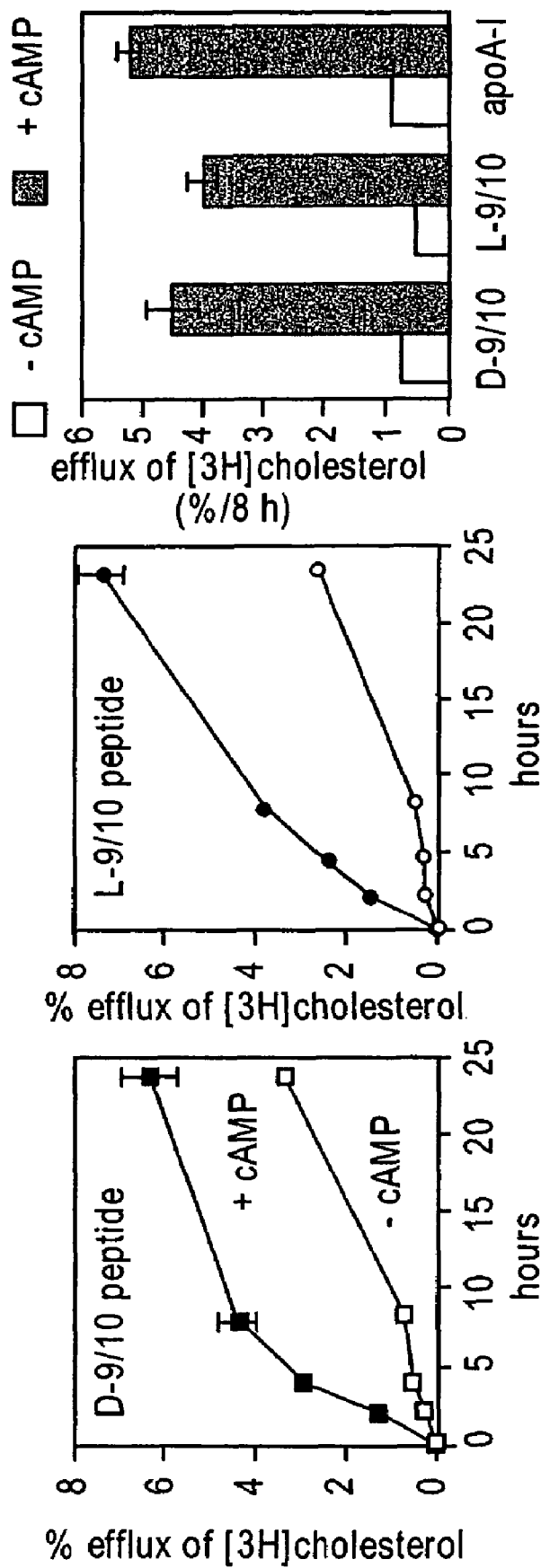
FIG. 11A-C illustrates data demonstrating that a synthetic peptide composed of all D-amino acids stimulates ABCA1-dependent cholesterol efflux. Panel A, ABCA1-dependent cholesterol efflux stimulated by a synthetic peptide compound of all D-amino acids. Panel B, ABCA1dependent cholesterol efflux stimulated by a synthetic peptide composed of all L-amino acids. Panel C, ABCA1-dependent cholesterol efflux stimulated by a synthetic peptide composed of all D-amino acids or all L-amino acids.

Synthetic Peptides Comprising D-Amino Stimulate ABCA1-Dependent Cholesterol Efflux A synthetic peptide composed of all D-amino acids stimulates ABCA1-dependent cholesterol efflux. The results are shown in FIG. 11. Such peptides composed of D-amino acids may also find applications as an orally administered agent.

Example 13

Figure 12:
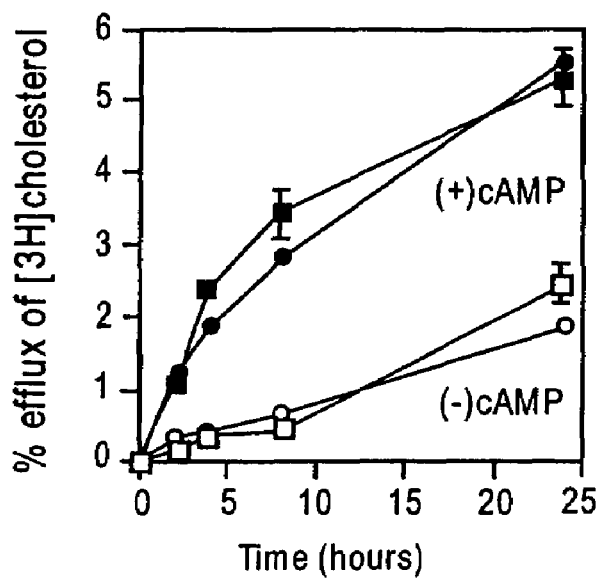
FIG. 12 illustrates data demonstrating the cholesterol efflux capability of a cysteine(thiol)-containing Apo A-I 9/10 peptide. A peptide based on helix 9/10 of Apo A-I was designed to have a cysteine residue at the polar/nonpolar interface of the amphipathic alpha helix. Cholesterol efflux activity assays demonstrated that the presence of a cysteine residue at the polar/nonpolar interface of the amphipathic alpha helix of the peptide does not interfere with the ability of the 9/10 peptide to stimulate ABCA1-dependent cholesterol.

Cholesterol Efflux Capability of a Cysteine(Thiol)-Containing Apo AI 9/10 Peptide A peptide based on helix 9/10 of Apo I was designed to have a cysteine residue at the polar/nonpolar interface of the amphipathic alpha helix: PALEDLRQGLLPVLESFCVK-FLSALEEYTKKLN (SEQ ID NO:1). Cholesterol efflux activity assays demonstrated that the presence of a cysteine residue at the polar/nonpolar interface of the amphipathic alpha helix of the peptide does not interfere with the ability of the 9/10 peptide to stimulate ABCA1-dependent cholesterol. Thus, 9/10 peptide may be used target antioxidant activity to ABCA1. The results are shown in FIG. 12.

Example 14

Cholesterol Efflux Capability of an Apo E Peptide

Figure 13:
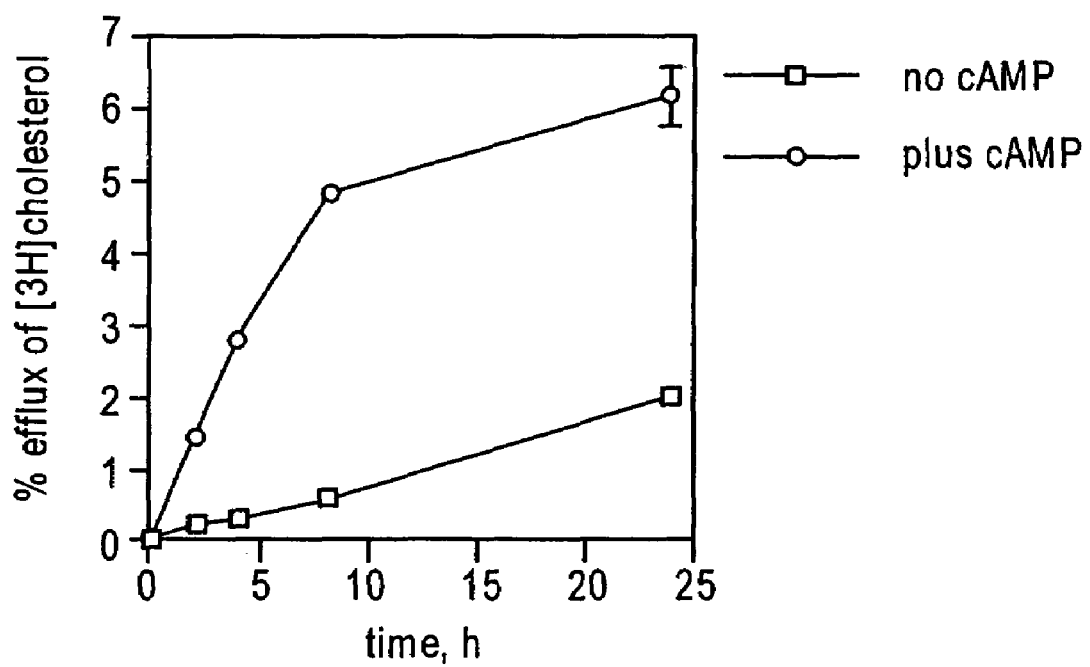
FIG. 13 illustrates data demonstrating the cholesterol efflux capability of an Apo E peptide. A 26 mer peptide derived from the C-terminus of apolipoprotein E (aa238-263) was modified to comprise an alignment of acidic amino acid residues on its polar surface. Cholesterol efflux assays demonstrated that shorter peptides can mediate ABCA1-dependent cholesterol efflux by creating an alignment of acidic polar residues within the helical structure.

A 26 mer peptide derived from the C-terminus of apolipoprotein E (aa238-263) and having the following sequence: EVRAKLEEWFQQIRLQAEEFQARLKS (SEQ ID NO:9) was modified to comprise an alignment of acidic amino acid residues on its polar surface. The cholesterol efflux capability of the peptide was tested as described in Example 1 above. This data shows that shorter peptides can mediate ABCA1-dependent cholesterol efflux by creating an alignment of acidic polar residues within the helical structure. The results are shown in FIG. 13.

Example 15

Effect of Aligned Acidic Residues Spanning the 9/10 Segment of Apo A-I on Mediation of ABCA1-Dependent Cholesterol Efflux Structural analogs of the 9/10 peptide and site-specific variants of full-length apoA-I will be used to further demonstrate that aligned, acidic residues mediate ABCA1-dependent cholesterol efflux. Studies of 18A are also proposed to define its dependence on aligned acidic residues for mediating ABCA1-dependent cholesterol efflux.

Peptide Synthesis

Synthetic peptides will be generated based on amphipathic α-helices (aa44-243) as found in apoA-I using the convention of Mishra et al. (Mishra, V. K. et al., *Biochemistry*, 37:10313-10324 (1998)) to define the helical segments. A synthetic peptide based on helices 9/10 (33-mer, aa 209-241) of apoA-I will be used as a positive control, which we have already shown stimulates cholesterol efflux and stabilizes ABCA1 (Natarajan, P. et al., *J. Biol. Chem.*, 279:24044-24052 (2004)). A unique 10/9 transposition peptide will be employed as a negative control since it will be used for in vivo studies testing the efficacy of the 9/10 peptide in atherosclerosis protection. The peptides will be synthesized by Biosynthesis Inc (Lewisville, Tex.) and modified by N-terminal acetyl- and C-terminal amide-groups. The final products will be isolated by HPLC and used at a purity of 95%. Lyophilized peptides will be dissolved in phosphate-buffered saline (PBS, pH=7.4). Stock solutions (1 mg/ml) will be filter sterilized and stored at 4° C. Protein concentrations will be based on the mass data provided by the manufacturer and verified using a BCA reagent kit (Pierce) that accurately quantifies peptides with MW as little as 1000 daltons. Typically, about 20 mg of each peptide will be required for cholesterol efflux studies, including enough material for detailed concentration dependence experiments. An additional 10 mg of each peptide will be needed for competitive-binding and -crosslinking experiments. The bulleted items below list the number of peptides required to complete structure-function studies and the rationale for creating each peptide.

Importance of Individual, Acidic Residues

The following sequence of amino acids creates the 9/10 helical peptide: PAL<u>E</u>DLRQGLLPVL<u>E</u>SFKVSFLSAL<u>E</u>EYTKKLN (SEQ ID NO:35). The underlined glutamates represent the three negatively charged residues that align in linear fashion down the length of the 33-mer segment (FIG. 4). The importance of each aligned residue will be evaluated by substituting serine for the underlined residues shown above. Thus three peptides each with the following single amino acid substitution: E212S, E223S and E234S will be generated. Each peptide is predicted to have reduced ability to stimulate ABCA1-dependent cholesterol efflux. Two peptides (D213S and E235S) will serve as controls (for changes in net charge) demonstrating that deletion of non-aligned negatively charged residues does not alter cholesterol efflux capability, underscoring the importance of aligned acidic residues. Each peptide will be analyzed and compared to site-specific variants of full-length apoA-I.

Extending and Shortening the Molecular Distances Between Aligned Residues

The length of the alignment of negatively charged residues will be extended and shortened while maintaining the net-charge, lipid-binding affinity, and linear orientation along the polar surface of the 9/10 segment. Each of the three aligned residues (E212, E223, and E234) in the 9/10 segment is separated from one another by ~16.2 Å (i.e. three α-helical turns) spanning a total length of ~32 Å. Two synthetic peptides will be created. One peptide will extend the distance between two of the aligned residues by 10 Å, stretching the alignment over 42 Å; this will be achieved by swapping E234 for N241. To condense the molecular distances between negatively charged residues without altering their alignment, E234 will be exchanged for Q216. The resulting peptide will possess all three aligned residues within a stretch of ~16 Å instead of the 32 Å normally present along the entire length of the 9/10 segment. It is predicted that peptides with extended and shortened alignments of acidic residues will lose the ability to stimulate ABCA1-dependent cholesterol efflux, perhaps stimulating lipid efflux independent of ABCA1. The latter peptide recapitulates the shortened alignment of acidic residues within 18A, thereby providing a molecular basis for its lack of strict dependence on ABCA1 for mediating cholesterol efflux.

Perturbation in the Alignment of Acidic Residues in 18A

The sequence <u>D</u>WLKAFY<u>D</u>KVF<u>E</u>KFK<u>E</u>AF (SEQ ID NO:50) creates the 18A (4F) peptide where the underlined residues align across the helical structure. This sequence will be used to create a control peptide to define ABCA1-dependent and -independent cholesterol efflux using HeLa cells. Swapping W for the last E in the sequence moves one acidic residue out of the alignment without altering the net charge and interfacial cationic residues. This change is restricted to the polar surface and is not predicted to alter the lipid-binding affinity of the peptide. We predict that the modified 18A peptide will exhibit reduced capacity to mediate ABCA1-dependent cholesterol efflux, manifesting cholesterol efflux independent of ABCA1 to a greater extent compared to the unmodified 18A peptide. A 36-mer helical peptide composed of two 18A molecules lacking a proline residue will be created to extend the alignment of acidic residues. We predict that the 36-mer peptide will be more dependent on ABCA1 for mediating cholesterol efflux compared to 37 pA, which will be used as a control.

Creation of 22-mer Helical Peptide with Aligned, Acidic Residues

A helical segment of 22 amino acids can support an alignment of acidic residues that spans five helical turns, like the 1/9 chimera that we previously found to stimulate cholesterol efflux (Natarajan, P. et al., *J. Biol. Chem.*, 279:24044-24052 (2004)). Utilizing a single 22-mer helix of apoA-I will allow us to create an alignment of acidic residues and endow cholesterol efflux capability, providing an alternative strategy for testing our hypothesis, which will support loss of function experiments brought about by removal of aligned acidic residues. Moreover, the studies will allow us to demonstrate that overall helix-length is not a requirement for mediating ABCA1-dependent cholesterol, given that a helical segment possesses an alignment of acidic residues. Helix 10 (aa220-241) of apoA-I is ideally suited for this purpose, because the 22-mer segment is not able to mediate ABCA1-dependent cholesterol efflux (Natarajan, P. et al., *J. Biol. Chem.*, 279: 24044-24052 (2004)), despite having high lipid-binding affinity. To endow helix 10 with ABCA1-dependent cholesterol efflux capability requires an N241→E substitution and the movement of K238 to a position at the lipid-water interface of the amphipathic α-helix. A 22-mer peptide based on helix 10 will serve as a negative control for these studies.

Studies of an all D-9/10 Peptide

Previous studies employing D-amino acids were conducted with 37 pA (Remaley, A. T. et al., *J. Lipid Res.*, 44:828-836 (2003)). These studies were partially confounded by the fact that 37 pA mediates cholesterol efflux independent of ABCA1, which we believe is attributed to split alignment of acidic residues. To demonstrate that there is no stereoselective requirement for mediating ABCA1-dependent cholesterol efflux, studies will be conducted with an all D-9/10 peptide. We hypothesize that since the linear series of acidic residues spanning the 9/10 segment is not likely to be altered by the use of D-amino acids, the D-9/10 peptide will be as efficient and the L-9/10 peptide in mediating cholesterol efflux in an ABCA1-dependent manner. Peptides comprising D-amino acids may be used as therapeutics, including orally administered therapeutics.

Expression/Purification of Recombinant apoA-I and apoA-I Point Variants

A bacterial expression system will be employed to express wild-type apoA-I and apoA-I point variants with serine substitutions. Production and isolation of highly purified apoA-I variants will be performed as described (Oda M. N. et al., *Biochemistry*, 40:1710-1718 (2001); Bielicki, J. K. and M. N. Oda, *Biochemistry*, 41:2089-2096 (2002); Ryan, R. O. et al., *Prot. Express. Purif*, 27:98-103 (2003)). Three apoA-I variants with single point-mutations (E212S, E223S & E234S) will be created to match the substitutions created within the 9/10 peptide analogs; an apoA-I variant with a serine substitution (D213S) for a non-aligned acidic residues will serve as a control. These studies are feasible since the 9/10 segment appears to represent the major element within the full-length molecule required for mediating ABCA1-dependent cholesterol efflux, where mutations in this region dramatically reduce efflux capability. However, the proposed studies are unique because the point mutations we propose are not expected to decrease the lipid-binding affinity of the segment, but loss of biological activity in mediating ABCA1-dependent cholesterol efflux is predicted with serine substitutions for aligned, acidic residues. Manipulation of the apoA-I coding sequence will be performed in the pBluescript KS (+) vector which will be propagated in *E. coli* DH5a cells. Constructs and mutations will be verified by DNA sequencing to confirm the introduction of desired mutations and the absence of unintended mutations. The apoA-I cDNA will be subcloned into the pET 20b+ plasmid (Novagen, Madison, Wis.) to yield the pNFXex vector for protein expression. The expressed proteins will contain the modified sequence: Met-(His)$_6$-Ile-Glu-Gly-Arg, (SEQ ID NO:49) which encodes the Factor-Xa cleavage site to facilitate removal of a His-tag following purification. Bacterial cells will be suspended in bacterial protein extract reagent and lysed by sonication at 4° C. Cellular debris will be removed by centrifugation (10,000 g, 15 min), and the clear lysates mixed with an equal volume of column loading buffer (40 mM NaPO$_4$, 1M NaCl, 6 M guanidine, pH=7.4). Lysates will be passed through 5 ml His-Trap chelating columns (Pharmacia Inc.) loaded with NiSO4. The column will be washed with 25 ml of loading buffer followed by 25 ml of wash buffer (20 mM NaPO$_4$, 0.5 mM NaCl, pH=7.4). Apolipoproteins will be eluted from columns with 25 ml of wash buffer containing 0.5 M Imidazole, pH=7.4. Eluted fractions (0.5 ml) will be monitored at 280 nm (subtracting for Imidazole absorbance) and peak fractions pooled. Pooled material will be dialyzed to Tris-buffered (20 mM, pH=7.4) saline-EDTA (2.7 mM) containing 1 mM benzamidine. Purified proteins will be filter-sterilized and stored at 4° C. Protein concentrations will be determined by the Markwell et al. method (Markwell, M. A. et al., *Anal. Biochem.*, 87:206-210 (1978)) and purity assessed by SDS-PAGE (Laemmli, U. K., *Nature*, 227:680-685 (1970)). The His-tag will be removed from expressed proteins for proposed studies.

Additional Considerations

The alignment of acidic residues spanning the 9/10 segment of apoA-I is contiguous with several acidic residues found in helix 8. The E212S and E223S substitutions (described above) are predicted to impair cholesterol efflux capability owing to the formation of a large gap between aligned, acidic residues across the region. However, the E234S variant may retain the ability to stimulate ABCA1-dependent cholesterol efflux, as the acidic residue that will be deleted is found at the end of the alignment, analogous to the A-I Δ232-243 truncation variant that stimulates cholesterol efflux (Chroni, A. et al., *J. Biol. Chem.*, 278:6719-6730 (2003)). If we find that the E234S variant stimulates ABCA1-dependent cholesterol efflux, we will test if an intact alignment present along the helix 8/9/10 region compensates for the loss of the single aligned, acidic residue (E234) from the end of the segment. To test this requires the creation of a double point-mutation (E234S/E205S) that creates a gap at the helix 8/9 boundary in addition to deletion of the C-terminal acidic residue. This is predicted to abolish cholesterol efflux activity, thereby providing an explanation as to why the A-I Δ232-243 variant retains the ability to stimulate cholesterol efflux. This is why the proposed studies benefit from comparisons between synthetic peptides and site-specific variants of full-length apoA-I.

Characterization of Peptides and apoA-I Point Variants

The serine substitutions for acidic residues are not likely to increase the polarity of the helical peptides and, therefore, we do not expect the lipid-binding affinity of the 9/10 analogs to be reduced compared to the native 9/10 peptide. As a result, the inability of structural analogs of the 9/10 peptide to mediate ABCA1-dependent cholesterol efflux can be directly attributed to alterations in the alignment of acidic residues. To verify the former, the hydrophobic moment (amphiphilicity) and hydrophobicity of helical peptides will be calculated as described (Natarajan, P. et al., *J. Biol. Chem.*, 279:24044-24052 (2004)). Biophysical studies will be conducted to verify that peptides and apoA-I point-variants form amphipathic α-helices and bind to phospholipid surfaces. The relative lipid-binding affinities of test material will be assessed by the rate of DMPC clearance as described (McLean, L. R. and K. A. Hagaman., Biochim. Biophys. Acta., 1167:289-295 (1993)). For quantitative assessments, the ability of peptides and apoA-I variants to penetrate a model membrane of egg-yolk phosphatidylcholine will be assessed using a surface balance technique. The assay quantifies the surface pressure (dyn/cm) at which the peptides no longer penetrate a model membrane compared to full-length, wild-type apoA-I (Gillotte, K. L. et al., *J. Biol. Chem.*, 274:2021-2028 (1999)). The α-helical content of peptides and apoA-I point-variants will be quantified by circular dichroism spectroscopy. The Ryan laboratory has also agreed to perform thermal- and guanidine-denaturation experiments to examine whether serine substitutions for acidic residues alter the stability of apoA-I (Beckstead, J. A. et al., *Biochemistry*, 42:9416-9423 (2003)).

Quantification of Cholesterol Efflux

HeLa cells stably transfected with ABCA1 cDNA will be used for the proposed studies. These studies require the use of two cell-lines (HeLa+ABCA1 and HeLa−ABCA1) for side-by-side comparisons of ABCA1-dependent and -independent mechanisms of cellular cholesterol efflux (Remaley, A. T. et al., *Biochem. Biophys. Res. Comm.*, 280:818-823 (2001); Remaley, A. T. et al., *J. Lipid Res.*, 44:828-836 (2003)). Briefly, cells will be seeded onto 24 well culture plates and labeled with [3H]cholesterol (1 µCi/ml) for 48 h. Following extensive rinsing, cellular lipids will be recovered by isopropanol extraction to establish the initial radioactivity present in the cells at t=0. Synthetic peptides will be used in lipid-free form prepared in serum-free RPMI and added to another set of cells to monitored cholesterol efflux. Aliquots of efflux media will be sampled at various times to quantify the kinetics of cholesterol efflux. Efflux media will be centrifuged (2000×g) and aliquots of supernatant quantified by liquid scintillation counting. Results will be expressed as a percentage of the initial [3H] appearing in the medium as a function of time. Experiments will be conducted over a wide range (1-100 µg/ml) of synthetic peptide concentrations in order to demonstrate strict dependence on ABCA1 for mediating cholesterol efflux. Full-length apoA-I will be used as a positive control and the 10/9 transposition peptide as a negative control; serum-free medium will be used to assess non-specific release of cholesterol in the absence of peptide. [3H]choline will be employed to monitor phospholipid efflux (Bielicki, J. K. et al., *J. Lipid Res.*, 33:1699-1709 (1992)). LDH release will be quantified to assess cytotoxicity (Remaley, A. T. et al., *J. Lipid Res.*, 44:828-836 (2003)). At least three independent experiments using triplicate wells for each treatment will be conducted to determine which peptides efflux cholesterol in an ABCA1-dependent manner. Three experiments of this type will be sufficient to demonstrate statistical differences as the results are predicted to be very clear establishing that some peptides mediate cholesterol efflux in an ABCA1-dependent manner while others do not. Means±SD will be calculated and statistical differences between peptides determined using Student's unpaired t-test, p<0.05 as significant. The concentration of peptide (and apoA-I variants) producing half (50%) maximal efflux of cholesterol will be calculated from data derived over the dose range. The data will be expressed on a mass- (μg/ml) and molar-basis allowing us to assess efficiencies between different helical structures that differ in molecular weights.

Cell-Surface Binding Studies

The 9/10 peptide will be evaluated for specific binding to ABCA1 expressing and non-expressing HeLa cells as described (Remaley, A. T. et al., *J. Lipid Res.*, 44:828-836 (2003)). These studies will test if 9/10 helical peptide competes for the same binding-site as full-length apoA-I. To establish this, the 9/10 peptide will be labeled with $^{125}$I. Such studies are feasible, as the 9/10 helical segment possesses a tyrosine residue that will permit radioiodination as described for peptide 18A (Garber, D. W. et al., *J. Lipid. Res.*, 42:545-552 (2001)). A two-step, sequential competitive-binding assay will be performed in order to prevent potential interactions between radiolabed peptide and competitor (apoA-I) in aqueous solution (Remaley, A. T. et al., *J. Lipid Res.*, 44:828-836 (2003)). HeLa cells will be incubated (4° C.) in the presence and absence of competitor for 3 h in MEM medium containing 10 mg/ml of BSA, washed, and then exposed (1 h) at 4° C. to individual radiolabeled peptides (1 μg/ml) to measure cell binding. Cells will be extensively rinsed and cell bound counts quantified following solubilization with 0.1 N NaOH. Experiments will be conducted over a wide range (1-40 μg/ml) of competitor concentrations. It is predicted apoA-I will completely block the binding of the 9/10 peptide to ABCA1 expressing cells in a concentration dependent manner. In another set of experiments, the 9/10 peptide will be used as the competitor and full-length apoA-I will be radiolabeled with $^{125}$I. This will permit us to demonstrate that the 9/10 peptide blocks apoA-I binding to ABCA1 expressing HeLa cells. Having established this, the ability of the 9/10 peptide analogs to compete with 125I-labeled apoA-I for specific-binding to ABCA1 expressing (positive control) and non-expressing (negative control) HeLa cells will be evaluated. For these studies, peptides with serine substitutions for aligned and non-aligned acidic residues will be employed over a concentration range established for the native 9/10 peptide. Peptides with extended and shortened alignments of acidic residues will be tested as well as 18A and its derivatives to establish the optimal length of the alignment for mediating binding. Peptides with an altered alignment of acidic residues are expected to compete poorly, failing to block the specific-binding of apoA-I to ABCA1 expressing HeLa cells. In contrast, peptides based on helix 10 that have been engineered with an alignment of acidic residues and the all D-9/10 peptide are predicted to block the specific binding of $^{125}$I-labeled apoA-I in a concentration dependent manner.

ABCA1 Stabilization.

To evaluate the loss (or retention) of biological activity of the 9/10 based peptides and apoA-I point variants in preventing ABCA1 degradation, stabilization experiments with J774 macrophages will be conducted (Natarajan, P. et al., *J. Biol. Chem.*, 279:24044-24052 (2004)). The use of J774 cells is preferred for these studies because rapid ABCA1 degradation is observed with this cell-line; whereas, HeLa cells have been transfected with ABCA1 cDNA and are not suitable for these experiments. Relative levels of ABCA1 protein will be quantified in cellular membranes obtained from J774 cells pretreated with cAMP to up-regulate ABCA1 protein (t=0). Subsequent incubations in the absence of cAMP (without peptides) will permit us to quantify relative decrease in cellular ABCA1 protein as a function of time. Parallel sets of cells will be exposed to test peptides, the native 9/10 peptide, full-length apoA-I (positive control), and apoA-I point variants. Detailed concentration dependence studies will be conducted to evaluate the relative potency of each peptide to stabilize ABCA1. Cell membranes will be harvested, applied to SDS 6% gels and separated proteins transferred to nitrocellulose membranes. A commercially available antibody specific for ABCA1 and an ECL-Plus enhanced chemifluoresence detection system will be used to quantify relative levels of ABCA1 protein using a BioRad FX-Phospholmager.

Crosslinking of the 9/10 Helical Peptide to ABCA1:

It is not known whether the 9/10 peptide can be directly crosslinked to ABCA1. This information may be useful for identifying the ligand-binding site on ABCA1 for helical apolipoproteins. Moreover, it will permit us to set-up a competitive crosslinking assay for testing whether specific peptides and apoA-I variants with serine substitutions lose the ability to form a molecular complex with ABCA1. For these studies, a series of crosslinking reagents will be evaluated since direct crosslinking of a helical peptide to ABCA1 has not yet been studied in great detail. The studies will employ EDC, a zero-length cross-linker reactive toward amino and carboxyl groups; DSG, a cross-linker with a spacer length of 7 Å; and DSP, a cross-linker with a 12 Å spacer. The studies will allow us to establish the distance over which the interaction occurs between the 9/10 peptide and ABCA1. The studies will employ a 9/10 helical peptide labeled with $^{125}$I. J774 macrophages will be exposed (1 h, 37° C.) to 11 g/ml of $^{125}$I-labeled 9/10 peptide in the presence of excess (50 μg/ml) unlabeled 9/10 peptide. Following exposure to the peptide, cells will be rinsed (4° C.) with PBS and exposed to the different crosslinking reagents for 1 h at room temperature as described by Fitzgerald et al. (Fitzgerald, M. L. et al., *J. Biol. Chem.*, 277:33178-33187 (2002)). Cells will be collected in immuno-perciptiation buffer (50 mM Tris pH 7.6, 150 mM NaCl, 0.25% sodium deoxycholate, 1% nonidet P-40 and 1 mM PMSF) and ABCA1 precipitated as described (Fitzgerald, M. L. et al., *J. Biol. Chem.*, 277:33178-33187 (2002)). Immunopercipitated proteins will be resolved by SDS-PAGE and detected using a Phospholmager. The use of $^{125}$I-labeled apoA-I will permit us to demonstrate crosslinking of the full-length apolipoprotein to ABCA1 (positive control). Having established this, the ability of the 9/10 peptide to compete with and block the formation of the $^{125}$I-apoA-I/ABCA1 complex will be evaluated. A series of studies employing structural analogs of the 9/10 peptide, 18A peptide and its derivatives, the 22-mer helix 10 peptides, and the all D-9/10 peptide will follow. It is predicted that peptides deficient in cholesterol efflux capability that lack specific binding activity will fail to compete with $^{125}$I-apoA-I for forming a molecular complex with ABCA1; whereas, the analogs that display an appropriate alignment will compete in a manner analogous to the native 9/10 helical peptide.

Example 16

An Alignment of Acidic Residues Enables apoA-I Central Helices to Mediate ABCA1-Dependent Cholesterol Efflux As discussed, disruption of apoA-I helices 9/10 dramatically reduces (~80-90%) ABCA1-dependent cholesterol efflux, consistent with the idea that this segment is primarily responsible for mediating cellular lipid efflux (Panagotopulos, S. E. et al., *J. Biol. Chem.*, 277:39477-39484 (2002);

Chroni, A. et al., *J. Biol. Chem.*, 278:6719-6730 (2003)). Indeed, deletion of apoA-I central helices (5/6, aa123-166) has very little impact on cholesterol efflux when the C-terminal 9/10 segment remains intact (Charulatha, V. et al., *J. Biol. Chem.*, Paper in press M406924200 (2004)). However, the central helices (Rifkind, B. M., *Am. J. Cardiol.*, 66:3A-6A (1990); Rothblat, G. H. and M. C. Phillips., *Curr. Opin. Lipidol.*, 2:288-294 (1991); Fielding, C. J. and P. E. Fielding., *J. Lipid Res.*, 36:211-228 (1995); Nissen, S. E. et al., *JAMA*, 290:2292-2300 (2003); Francis, G. A. et al., *J. Clin. Invest.*, 96:78-87 (1995); Remaley, A. T. et al., *Arterioscler. Thromb. Vasc. Biol.*, 17:1813-1821 (1997)) of apoA-I can function autonomously as an effective mediator of ABCA1-dependent cholesterol efflux when the 9/10 segment has been deleted or disrupted in conjunction with removal of aa1-43 (Chroni, A. et al., *J. Biol. Chem.*, 278:6719-6730 (2003); Chroni, A. et al., *Biochemistry*, 43:2126-2139 (2004)). This suggests that the central helices of apoA-I can be used as a model to identify determinants of ABCA1-dependent cholesterol efflux. Understanding how apoA-I central helices mediate ABCA1-dependent cholesterol efflux is of biological relevance as this may lead to a greater understanding of the apoA-I/ABCA1 interaction and, ultimately, a consensus as to how helical apolipoproteins mediate cholesterol efflux. Mutagenesis experiments with apoA-I central helices reveal that tertiary interactions within apoA-I are not as important as aspects of secondary α-helical structure for mediating cellular lipid efflux, consistent with the involvement of aligned, acidic residues in the process (Chroni, A. et al., *Biochemistry*, 43:2126-2139 (2004)). Helical net diagrams reveal that negatively charged amino acids align across helices 6/7 of apoA-I central helices, similar to the 9/10 segment of apoA-I that mediates ABCA1-dependent cholesterol efflux (Preliminary results). This suggests that aligned, acidic residues may represent a common determinant of ABCA1-dependent cholesterol efflux shared among seemingly distinct apoA-I helical segments. The proposed studies will test this utilizing synthetic peptides and site-specific variants of apoA-I Δ1-59/Δ185-243. Our model predicts that a peptide based on the 6 plus 7 helical combination will mediate ABCA1-dependent cholesterol efflux; whereas, peptides based on helical combinations derived from apoA-I central helices that do not display an alignment of acidic residues will fail to stimulate cholesterol efflux. Structural peptide analogs and site-specific variants of apoA-I Δ1-59/Δ185-143 in which acidic residues are replaced by serines will be used to obtain evidence in support of the alignment hypothesis. This will allow us to demonstrate that apoA-I central helices mediate cholesterol efflux via a mechanism analogous to the 9/10 segment of apoA-I.

Consideration of aligned, acidic residues may explain why various helix-deletion mutants of apoA-I retain cholesterol efflux capability. For example, removal of apoA-I helices 7-9 has no effect on ABCA1-dependent cholesterol efflux (Panagotopulos, S. E. et al., *J. Biol. Chem.*, 277:39477-39484 (2002)). Deletion of apoA-I helices 7-9 creates a fusion of helices 6 & 10, which brings together a series of aligned negatively charged amino acids that span the helical combination similar to the native 9/10 structure (Preliminary results). We observed a similar phenomenon by adding the 11-mer helix 9 to helix 1 creating a 1/9 chimera that stabilized ABCA1 and mediated cellular cholesterol efflux (Natarajan, P. et al., *J. Biol. Chem.*, 279:24044-24052 (2004)). These observations support the idea that the alignment of acidic residues within amphipathic α-helices may correspond to a previously unrecognized determinant of ABCA1-dependent cholesterol efflux. Moreover, this key aspect of α-helical secondary structure appears to be repeated across a number of apoA-I helical segments implicated in ABCA1-dependent cholesterol efflux. This redundancy (in the alignment of acidic residues) may have occurred as a result of duplication events in the apoA-I gene that propagated important determinants of ABCA1-dependent cholesterol efflux throughout the C-terminal end of the apoA-I molecule. Such redundancy in form & function may provide an explanation as to why it has been difficult to identify determinants of cholesterol efflux using the helix deletion strategy alone. Indeed, the A-I Δ232-243 variant (deficient in part of helix 10) effluxes cholesterol normally despite the removal of an aligned acidic residue from the end of helix 10 (Chroni, A. et al., *J. Biol. Chem.*, 278:6719-6730 (2003)). The fact that acidic residues align across much of the C-terminus of apoA-I may account for the cholesterol efflux capability of A-I Δ232-243 if other acidic residues within the alignment compensate for the loss of a single acidic residue within the context of full-length apoA-I and/or the central helices. The removal of a single, aligned acidic residue from the 9/10 peptide may abolish ABCA1-dependent cholesterol efflux. Alternatively, deletion of several acidic residues simultaneously may be required to create sufficient gaps in an alignment to produce loss of biological activity using the full-length apoA-I molecule. Thus, results obtained with synthetic peptides will be compared with those obtained using site-specific variants of apoA-I.

Two complimentary approaches will be employed. Based on our model of aligned, acidic residues we hypothesize that a combination of helices 6/7 will be sufficient to stimulate cholesterol efflux via ABCA1. These studies together with mutagenesis experiments utilizing A-I Δ1-59/Δ185-243 will further confirm that aligned, acidic residues are a determinant of cholesterol efflux, as described for the 9/10 segment of apoA-I.

Design of Synthetic 44-mer Peptides

Synthetic peptides (44-mers) composed of apoA-I helices 6/7 and 5/6 will be synthesized, since both helical combinations display an alignment of acidic residues. Peptides composed of helices 2/3 and 4/5 will serve as controls and are not expected to mediate ABCA1-dependent cholesterol efflux because they lack an alignment of acidic amino acids. If we find that the 6/7 peptide mediates ABCA1-dependent cholesterol efflux, structural analogs with serine substitutions (D168S and D156S) will be employed to demonstrate loss-of-function, providing evidence that aligned, acidic residues are important for ABCA1-dependent cholesterol efflux, as found for the 9/10 peptide based on apoA-I.

Alternative Approach

We will also successively truncate (using mutagenesis and expression strategies) A-I Δ1-59/Δ185-243 starting with the N-terminus helix to identify the minimum structure required for mediating cholesterol efflux. In experiments to be run in parallel, we will express two truncated forms corresponding to helices 2/3/4 and 5/6/7 essentially dividing apoA-I central helices into two halves. The ability of each to stimulate ABCA1-dependent cholesterol efflux will be evaluated. The former has been shown to efflux cholesterol from CHO cells, but the dependence of cholesterol efflux on ABCA1 was not evaluated (Toledo, J. D. et al., *Archiv. Biochem. Biophys.*, 428:188-197 (2004)). This indicates that our experimental approach to identify helical combinations that mediate ABCA1-dependent cholesterol efflux is valid, as helical peptides derived from apoA-I central helices avidly bind lipid and promote cholesterol efflux.

Generation of A-I Δ1-59/Δ185-243 and its Point Variants

ApoA-I cDNA encoding the truncation variant A-I Δ1-59/Δ185-243 will be subjected to mutagenesis to create a double point-variant (E146S/D156S) which produces a large gap in the alignment of acidic residues spanning helices 6 and 7. A triple point mutation (D147S/E146S/D156S) will also be created to produce an even larger gap that takes into account acidic residues that aligned at the helix 5/6 boundary. It is predicted that both point-variants will exhibit reduced capacity to mediate ABCA1-dependent cholesterol efflux, particularly the latter triple mutation that ensures disruption in the alignment of acidic residues across helices 5-7 within the A-I Δ1-59/Δ185-243 molecule. For these studies, A-I Δ1-59/Δ185-243 and its point variants will be expressed in bacterial cells and purified by His-Trap chelating columns. The His-tag will be removed from the expressed proteins prior to studies. SDS-PAGE using 4-20% gels will establish purity of the isolated proteins.

Characterizations of Helical Peptides and A-I Δ1-59/Δ185-243 Point-Variants

To verify that the serine substitutions for acidic residues do not appreciably alter lipid-binding affinity and α-helical content compared to parent (native) structures, biophysical studies will be conducted as described above. These studies include assessment of DMPC clearance and quantification of monolayer exclusion pressure. The stability of the A-I Δ1-59/Δ185-243 molecule will be assessed, compared to full-length wild-type apoA-I, as judged by its thermal- and guanidine-denaturation behavior. Similar experiments will be conducted with the A-I Δ1-59/Δ185-243 point variants to demonstrate that the serine substitutions for aligned, acidic residues do not further effect the stability of the molecule.

Cholesterol Efflux, Competitive-Binding and ABCA1 Stabilization Activities.

HeLa cells will be used to test whether specific helical peptides based on apoA-I central helices, structural analogs and the A-I Δ1-59/Δ185-243 point variants mediate cholesterol efflux in an ABCA1-dependent manner. Detailed concentration dependence studies as well as kinetic experiments utilizing the lipid-free peptides and A-I Δ1-59/Δ185-243 point variants will be conducted, thus establishing whether specific structural perturbations result in a complete loss of function or whether the segment less potent in terms of mediating cholesterol efflux. The studies will also test whether the helical peptides based on A-I central helices compete for the binding of $^{125}$I-labeled, full-length apoA-I to ABCA1 expressing HeLa cells. Initial binding studies will employ the specific helical peptide under investigation as the competitor and the A-I Δ1-59/Δ185-243 molecule as a positive control. Having established the concentration range by which these native structures compete with $^{125}$I-labeled apoA-I for specific binding, studies will follow with the structural analogs of the 6/7 peptide and A-I Δ1-59/Δ185-243 point variants that possess serine residues for acidic amino acids. It is predicted that peptides with a deficiency in acidic residues will fail to complete with apoA-I for the binding to ABCA1-expressing HeLa cells, paralleling the loss of cholesterol efflux activity. In some experiments, $^{125}$I-labeled 9/10 peptide will be used to demonstrate that incubations with apoA-I central helices (i.e. the 6/7 peptide and A-I Δ1-59/Δ185-243) block its binding to ABCA1 expressing cells; 6/7 peptide analogs and A-I Δ1-59/Δ185-243 with point variations are predicted to fail to compete for specific binding. In this way, we will be able to demonstrate that apoA-I central helices mediate specific binding via a mechanism involving aligned, acidic residues analogs to the 9/10 segment of apoA-I. ABCA1 stabilization experiments will be conducted as described above employing J774 macrophages. The ability of A-I Δ1-59/Δ185-243 to form a molecular complex with ABCA1 will be assessed in crosslinking studies as described above.

Example 17

The Lipid-Binding Domain of apoE Mediates ABCA1-Dependent Cholesterol Efflux

Our preliminary results suggest that the C-terminal domain of apoE is able to mediate ABCA1-dependent cholesterol efflux; whereas, the N-terminal domain was a poor effluxer of cholesterol. The proposed studies will show which of the two helical segments that comprise the C-terminal domain of apoE is able to mediate ABCA1-dependent cholesterol efflux. Studies will be conducted using variants of apoE3 with point mutations to establish the role of aligned, acidic residues in stabilizing ABCA1 and mediating cellular cholesterol efflux.

Design of Synthetic Peptides 33-mer peptides will be synthesized that correspond to the first (aa216-248, with aligned acidic residues) and second helical segments (aa267-299, without aligned, acidic residues) that comprise most of the C-terminal domain of apoE. We will also test whether a 22-mer peptide based on aa216-237 is sufficient for mediating ABCA1-dependent cholesterol efflux, as it possesses an alignment of acidic residues (FIG. 6B). Predicated on the outcome of these studies, peptide analogs based on the first 33- and/or 22-amino acids of the C-terminus that possess serine substitutions for aligned, acidic residues will be engineered. In this way we will be able to identify the segment within the C-terminal domain apoE that mediates ABCA1-dependent cholesterol efflux and show that the segment is dependent on acidic residues to support this activity.

Additional Considerations

It is conceivable that the 33-mer helical peptide (aa216-248) derived from the first helical segment of the C-terminus of apoE may exhibit a lipid-binding affinity lower than that of the 9/10 segment of apoA-I. This does not rule-out that the peptide will mediate cholesterol efflux and/or stabilize ABCA1, as the segment displays an alignment "enriched" in acidic residue that may compensate for reduced lipid-binding affinity. If we find that the 33-mer peptide (aa216-248) does not stimulate ABCA1 dependent cholesterol efflux, we will extend the length of the peptide with a sequence derived from the remaining portion of the segment (aa249-266) that includes hydrophobic phenylalanines (F). This strategy coupled with the proposed serine substitutions will further confirm that helical peptides comprising aligned, acidic residues and having high lipid-binding affinity mediate ABCA1-dependent cholesterol efflux.

Expression/Purification of apoE Point Variants

Full-length apoE3 as well as an apoE3 point variant (E220S/E245S) will be expressed in bacterial cultures and purified by HPLC as described (Narayanaswami, V. et al., *J. Biol. Chem.*, 279:14273-14279 (2004)). The double point mutation removes acidic residues from the two ends of the long alignment, thus confining the remaining acidic residues to a short helical stretch (FIG. 8B). The final products will be tested for purity by SDS-PAGE (4-20% gels).

Characterization of apoE-Based Peptides and apoE Point Variants

The relative lipid-binding affinities of synthetic peptides will be quantified by measuring the rate of DMPC clearance and by performing assessments of monolayer exclusion pressure. The amphiphilicity (i.e. hydrophobic moment) and hydrophobicity of helical peptides will be calculated as described (Natarajan, P. et al., *J. Biol. Chem.*, 279:24044-24052 (2004)). This will allow us to create a data set utilizing the information derived from all peptides used on the proposed studies to determine if ABCA1-dependent cholesterol efflux correlates with lipid-affinity and parameters related to the hydrophobicity of a given helical segment. Information of this type is currently not available for the peptides derived from apoE, which display an alignment enriched in acidic residues. The stability of the apoE point variant will be assessed in thermal- and guandidine-denaturation experiments.

Cholesterol Efflux, Competitive-Binding and ABCA1 Stabilization Activities

HeLa cells +ABCA1 and −ABCA1 will be used to identify segments of apoE that are responsible for mediating cellular cholesterol efflux. Detailed concentration dependence studies employing synthetic peptides and site-specific variants of apoE3 will be performed. Full-length apoE3 will be used as a positive control. Competitive binding studies will be conducted as described using $^{125}$I-labeled apoE3. This will allow us to establish that peptide aa216-248 effectively competes with full-length apoE for specific binding to ABCA1 expressing HeLa cells; whereas the Class G peptide aa267-299 does not. The ability of peptide analogs and the site-specific variant of full-length apoE3 to compete with $^{125}$I-apoE3 for binding will also be examined providing evidence that acidic residues are required to interact with ABCA1 expressing cells. In some experiments, $^{125}$I-apoA-I will be employed in conjunction with the apoE-based peptides and site-specific variant of apoE to demonstrate that residues 216-248 with its alignment of acidic residues is a common feature of apolipoproteins required for binding to ABCA1 expressing cells. J774 macrophages will be used to test whether helical peptides and site-specific variants of apoE stabilize cellular ABCA1 protein. Competitive crosslinking experiments will be performed as described above.

Consideration of Other Apolipoproteins

To demonstrate the predictive ability of our model, synthetic peptides will be used to pinpoint helical segments within other apolipoprotein family members that mediate ABCA1-dependent cholesterol efflux. Recent studies indicate that the central helices of apoA-IV contain determinants of ABCA1-dependent cholesterol efflux (Pearson, K. et al., *Biochemistry*, 43:10719-10729 (2004)). This coincides with segments that display aligned, acidic residues. Of interest is the observation that the A-IV Δ1-39/Δ271-376 variant exhibits decreased lipid-binding affinity, but retains efficient cholesterol efflux activity (Pearson, K. et al., *Biochemistry*, 43:10719-10729 (2004)). This suggests that factors in addition to high lipid-binding affinity are required to interact with ABCA1, as we have suggested (Natarajan, P. et al., *J. Biol. Chem.*, 279:24044-24052 (2004)). We have noted that within apoA-IV central helices, two contiguous pairs of α-helices display aligned, acidic residues corresponding to aa161-204 and aa205-248. The former overlaps with the sequence suggested by Pearson et al (Pearson, K. et al., *Biochemistry*, 43:10719-10729 (2004)) as a candidate for mediating ABCA1-dependent cholesterol efflux. The 44-mer peptides based on these α-helices of apoA-IV are predicted to mediate ABCA1-dependent cholesterol efflux and prevent ABCA1 degradation. Peptides based on aa62-94 (33-mer) and aa95-138 (44-m34) will serve as controls for the proposed studies. The former possesses an alignment of acidic residues disrupted by the insertion of a positively charged residue and the latter the alignment is split, not contiguous across the two segments. The remaining apoA-IV α-helices (aa139-160) bear little in the way of aligned acidic residues. Our analyses cover most of the helical segments that comprise the central helices of apoA-IV. The remaining apolipoproteins (apoA-II, C-I, C-II, and C-III) are relatively small in size requiring a single peptide to identify segments that mediate ABCA1-dependent cholesterol efflux. These studies together with those of apoA-I and E will provide additional proof that a specific helical motif within apolipoprotein gene family stimulates cholesterol efflux.

Example 18

Determination of Whether a Helical Peptide Based on the 9/10 Segment of Apo A-I Stimulates the Regression of Atherosclerotic Lesions These studies will be conducted in several stages using apoE deficient (apoE−/−) mice fed a high-fat (21% wt/wt), 0.15% cholesterol diet (Tek-lab) for 20 weeks. First we will determine the plasma residence times and metabolic fate of the injected 9/10 peptide. The ability of the injected peptide to associate with plasma HDL and enhance the cholesterol efflux capability of sera will be examined. Second, we will test if repeated injection of the 9/10 peptide reduces aortic-lipid & macrophage-content as well as atherosclerotic lesions. Peptides (9/10 & 10/9) and full-length apoA-I will be used in lipid-free form.

Establishing In Vivo Kinetics of the 9/10 of Peptide in the Disease Model

We will inject ~100 µg (in 50 µl saline) of test material/animal (i.e. 5 mg/kg) to determine the in vivo kinetics and metabolic fate of 9/10 peptide, relative to apoA-I and the 10/9 peptide. This dose is reasonable given that maximal ABCA1 stabilization and cholesterol efflux were achieved using ~10-25 µg/ml of the 9/10 helical peptide. Peptides and full-length apoA-I will be dissolved in sterile physiological saline and injected intravenously (i.v.) after a 4 hour fast. In order to track the injected material, the peptides and apoA-I will be labeled with $^{125}$I (IodoBEAD reagent, Pierce), as described (Garber, D. W. et al., *J. Lipid. Res.*, 42:545-552 (2001)). A total of 30 mice will be utilized for these initial studies. The 30 mice will be assigned to three groups: 10 mice will be injected with the 9/10 peptide, 10 with the 10/9 transposition peptide and remainder with full-length apoA-I. Male mice 26 weeks of age fed a high-fat, cholesterol diet will be utilized. A small volume of blood (~0.04 ml) will be obtained from the retro-orbital plexus of mice at specified times post-injection (0.5, 1, 2, 4 and 20 h) using alternating eyes. Plasma will be isolated by low speed centrifugation (1000×g, 20 min at 4° C.) and a small aliquot directly counted for radioactivity using a Packard E5002 Gamma counter. Free $^{125}$I in plasma will be quantified by trichloroacetic acid precipitation (1 ml of 10% TCA/110 µl of plasma) as described (Navab, M. et al., *Circulation*, 105:290-292 (2002)). Plasma kinetic data will be analyzed using standard software (PKAnalyst; MicroMath Scientific Software, Salt Lake City, Utah). During the course of the experiment, mice will be kept in metabolic cages allowing us to collect urine for quantification of $^{125}$I radioactivity, which will provide information as to what fraction of the injected peptide is degraded over 20 h. At the end of the study (i.e. at 20 h), tissues (liver, kidney, brain, lung, spleen, heart, aorta, and adrenals) will be harvested for determinations of the distribution of $^{125}$I radioactivity.

Having established the time-course for the clearance of peptides from plasma, a second injection will be performed in another set of 30 mice to isolate HDL at the time radiolabeled peptides are most abundant in plasma post injection. Blood will be collected via cardiac puncture, and plasma isolated. At the completion of blood draws, tissues will be harvested for analysis of the distribution of $^{125}$I-peptides. This analysis will allow us to examine the tissue distribution of $^{125}$I at an early time-point to facilitate comparisons with the results obtained at 20 h (above). Pooled plasma (0.5 ml) will be subjected to FPLC using two Superose 6 columns connected in series (Forte, T. M. et al., *J. Lipid Res.*, 43:477-485 (2002)). The plasma distribution of radiolabeled peptides in relation to the HDL peak will be determined using mouse HDL and albumin as calibrators. Total radioactivity, cholesterol (Sale, F. O. et al., *Anal. Biochem.*, 142:347-350 (1984)) and protein (Markwell, M. A. et al., *Anal. Biochem.*, 87:206-210 (1978)) will be quantified in each fraction to define the distribution of injected peptide in relation to HDL. The amount of peptide bound to HDL will be calculated based on the specific activity of the peptides injected into mice, subtracting TCA-soluble counts. Pooled HDL fractions will be analyzed by nondenaturing gradient gel electrophoresis (4-30%) to evaluate whether injected peptide forms new HDL subfractions (Forte, T. M. et al., *J. Lipid Res.*, 34:317-324 (1993)).

Tissue Cholesterol Mobilization, Cholesterol Efflux Potential of Sera and Endogenous ABCA1

A recent study indicates that a recombinant variant of apoA-I complexed with phospholipid and injected i.v. increased the cholesterol efflux activity of sera and rapidly mobilized tissue cholesterol in mice (Shah, P. K. et al., *Circulation*, 103:3047-3050 (2001)). To determine the effects of a helical peptide following i.v. infusion, we will use the 9/10 peptide derived from apoA-I. For these studies, 48 apoE−/− mice fed (20 weeks) a high-fat, cholesterol diet will be assigned to four groups of 12 mice to be injected (i.v. after a 4 h fast) with saline, the 9/10 peptide, peptide 10/9 and full-length apoA-I, respectively. At a predetermined time (~6 h post-injection), plasma will be obtained (via cardiac puncture) from mice and assayed for total cholesterol, free and esterified cholesterol, and HDL cholesterol. Oil-red O staining and immunohistological examination will quantify plaque lipid- and macrophage-contents, respectively, as described above. We predict an increase in plasma free and esterified cholesterol with the 9/10 peptide and apoA-I with corresponding reductions in plaque lipid, consistent with a mobilization of tissue cholesterol. Sera from mice will be diluted (0.05-1%) and tested for cholesterol efflux capability ex vivo using J774 macrophages treated with and without a cAMP analog (Natarajan, P. et al., *J. Biol. Chem.*, 279:24044-24052 (2004)). This will permit us to determine if the presence of the peptide enhances efflux capability in a manner consistent with elevated serum cholesterol levels and reduction in aortic lipid content. To test if the 9/10 peptides increases cellular ABCA1 protein in vivo, hepatocytes will be obtained from mice at ~6 post-injection (Wang, N. et al., *J. Clin. Invest.*, 111:99-107 (2003)), i.e at the time blood is drawn for lipid analyses. Relative levels of cellular ABCA1 protein will be measured across treatment groups using procedures described above, including assessments of ABCA1 mRNA (Cavelier, L. et al., *J. Biol. Chem.*, 276:18046-18051 (2001)). The extent by which hepatocytes efflux cholesterol will be determined using apoA-I as an acceptor. The number of mice is based on the variance for quantification of plasma cholesterol levels and ex vivo analyses of cholesterol efflux capability (Shah, P. K. et al., *Circulation*, 103:3047-3050 (2001)). Data will be presented as means±SD and for group comparisons, ANOVA followed by Tukey's test (with p0.05) will be used to determine significance.

Alternative Approaches

Multiple doses (i.e., from about 5, 10, 15, 20, 25, or more mg/kg) of a lipid-free form of a helical peptide based on apoA-I will be used to mobilize aortic cholesterol (as judged by an increase in plasma cholesterol). These experiments in conjunction with the 9/10 peptide complexed with DMPC will allow us to determine if the lipid-free form of the 9/10 peptide that mediates ABCA1-dependent cholesterol efflux has potential therapeutic applications.

Extent of Lesion Regression Following Repeated Injection of the 9/10 Peptide

ApoE−/− mice (male) fed a high-fat, cholesterol diet for 20 weeks will receive intraperitoneal injections (i.p.) of saline, the 9/10 peptide, peptide 10/9 and full-length apoA-I over period of one month. During the injection period, the mice will be fed a chow diet. To establish that peptides injected i.p. enter the plasma compartment, 30 apoE−/− mice will be assigned to three groups (randomly selected) of 10 mice. The mice will be injected (i.p.) with $125'$-9/10 peptide, $^{125}$I-10/9 peptide, and $^{125}$I-apoA-I to evaluate the time course for the appearance and removal of peptides from plasma. Based on the outcome of these studies, a schedule for i.p injection will be established in which mice received i.p. injections either daily or every other day for a thirty day period including weekends and holidays. The regression study will comprise a total of 120 mice (male) 26 weeks of age (20 weeks on high fat, cholesterol diet). Breeding pairs of apoE−/− mice will be purchased from the Jackson Laboratory and a colony of 140 male mice of similar ages will be established. The proposed studies will employ four groups of 30 mice. One group of mice will be injected with the 9/10 peptide, the second group with apoA-I, and the third with the 10/9 peptide and the fourth with saline vehicle. The amount of peptide (and apoA-I) to be injected will be based on the outcome of acute studies employing either 5 or 20 mg/kg of test material. Cross-section lesion area and macrophage content in the proximal aorta will be quantified and the descending-thoracic and abdominal aortas used for assessments of fatty streak lesion area. The number of mice in each group is based on previous studies and power calculations to determine statistically significant differences in lesion area in apoE−/− mice (Paszty, C. et al., *J. Clin. Invest.*, 94:899-903 (1994); Plump, A. S. et al., *Proc. Natl. Acad. Sci.*, 91:9607-9611 (1994)). A total of 90 mg of each peptide and apoA-I will be required to complete the proposed studies, if a daily injection schedule is adopted.

Assessment of Atherosclerotic Lesions

For quantitative analyses, mean lesion area per section of tissue will be determined as previously described (Paszty, C. et al., *J. Clin. Invest.*, 94:899-903 (1994); Plump, A. S. et al., *Proc. Natl. Acad. Sci.*, 91:9607-9611 (1994)). A series of four 10 µm section beginning 80 µm from the first and most proximal section of the heart will be taken distal to the point where the aorta first becomes rounded. The area of oil-Red-O staining will be determined. The mean lesion area per section per animal will be calculated in each group. The descending thoracic aorta and the abdominal aorta up to the point of the common iliac arteries will be formal-sucrose fixed, opened longitudinally and stained with Sudan IV to visualize the extent of fatty streaks. Quantification of the percentage of aortic surface covered with atheroma will be performed using computer-assisted planimetry (Shah, P. K. et al., *Circulation*, 103:3047-3050 (2001); Shah, P. K. et al., *Circulation*, 97:780-785 (1998)). The technical observer will not know the treatment groups. Data will be expressed as Means±SD. Group comparisons will be made using unpaired t-test or ANOVA followed by Newman-Keuls test with a two-tailed p<0.05 value considered to be significant.

Aortic Macrophage Content

Immunohistological analyses will be performed on serial sections of the aorta (Shah, P. K. et al., *Circulation*, 103:3047-3050 (2001); Shah, P. K. et al., *Circulation*, 97:780-785 (1998)). The heart and proximal aorta will be perfusion-fixed with 4% paraformaldehyde, 5% sucrose and 20 mM EDTA (pH=7.4) for 10 minutes. Tissue will be excised and embedded in OCT compound (TissueTek), frozen on dry ice, and stored at 70° C. Serial 10 µm thick sections (every fifth section from the middle of the ventricle until the appearance of the aortic valve) will be collected on poly-D-lysine-coated slides. Macrophages will be localized using a rat anti-mouse monoclonal antibody, Mac-1 (Chemicon International). Sections will be treated with PBS/0.2% triton X-100 and then blocked; antibody to Mac-1 will be added and incubated for 18 h in a humidified chamber; non-immune serum will be used as a control. Sections will be incubated with biotinylated anti-rat IgG followed by avidin-biotinylated alkaline phosphatase for 60 min, processed for alkaline phosphatase, and then counterstained with hematoxylin. Lesion area occupied by macrophages will be quantified by scanning with a CCD camera using Image ProPlus software.

Plasma Lipid and Lipoprotein Determinations

Plasma non-HDL-cholesterol, HDL-cholesterol and triglycerides will be quantified using Wako kits. Analyses will be performed just prior (2-3 days) to the initiation of the injections and at 30 days at the end of the experiment. To determine if the peptides alter HDL particle size, nondenaturing gradient gel electrophoresis will be performed on HDL isolated by FPLC (Forte, T. M. et al., *J. Lipid Res.*, 43:477-485 (2002)). Plasma LCAT activity will be quantified using an exogenous proteoliposome substrate (Chen, C.-H. and J. J. Albers., *J. Lipid Res.*, 23:680-691 (1982)) and PON activity as described (Forte, T. M. et al., *J. Lipid Res.*, 43:477-485 (2002)). The former will provide an independent assessment of RCT and the latter will allow us to examine if the anti-inflammatory defenses of HDL are increased as a result of the 9/10 peptide.

Toxicity Testing

The levels of plasma lactate dehydrogenase (LDH) will be quantified as described (Stagsted, J. and J. F., *Free Radic. Res.*, 36:779-789 (2002)) to verify that injected peptides do not induce toxicity in vivo. Erythrocyte stability will be assessed using isolated cells and LDH/hemoglobin release (Stagsted, J. and J. F., *Free Radic. Res.*, 36:779-789 (2002)). These latter end-points are commonly used to assess oxidative stress and erythrocyte stability across different species and can be performed on a small number of cells.

Example 19

Exemplary Peptides of the Invention

Selected exemplary helix peptides of the present invention are set forth below:

Helices 9 and 10:
(SEQ ID NO: 35)
PALEDLRQGLLPVLESFKVSFLSALEEYTKKLN.

The sequence identified as "ApoA-I Helices 9 and 10" represents a 32mer native combination (i.e. the sequences are naturally adjacent) of native ApoA1 α-helical subsequences joined by a proline at residue 220. The amino acids underlined in the above sequence represent the negatively charged residues which align on the hydrophilic face of the α-helix and correspond to E212, E223 and E234 of apoA-I primary sequence.

Helices 1 and 2:
(SEQ ID NO: 36)
LKLLDNWDSVTSTFSKLREQLGPVTQEFWDNLEKETEGLRQEMS.

The sequence identified as "ApoA-I Helices 1 and 2" represents a 44mer native combination of two 22mers of native ApoA1 subsequences having a proline between the two amphipathic helices. The amino acids underlined in the above sequence represent the negatively charged residues which align on the hydrophilic face of the α-helix and correspond to E62, D73 and E80 of apoA-I primary sequence.

Helices 1 and 9:
(SEQ ID NO: 37)
LKLLDNWDSVTSTFSKLREQLGPALEDLRQGLL.

The sequence identified as "ApoA-I Helices 1 and 9" represents a 33mer ApoA1 chimeric sequence (i.e. naturally non-adjacent subsequences) having a 22mer of helix 1 joined to an 11 mer of helix 9 by a proline residue. The amino acids underlined in the above sequence represent the negatively charged residues which align on the hydrophilic face of the α-helix and correspond to D51, E62 and E212 of apoA-I primary sequence.

Helices 8 and 10:
(SEQ ID NO: 38)
ARLAEYHAKATEHLSTLSEKAKPVLESFKVSFLSALEEYTKKLN.

The sequence identified as "ApoA-I Helices 8 and 10" represents a 44mer ApoA1 chimeric sequence having a 22mer of helix 8 joined to an 22mer of helix 10 by a proline residue. The amino acids underlined in the above sequence represent the negatively charged residues which align on the hydrophilic face of the α-helix and correspond to E191, E198, E205, E223, and E234 of apoA-I primary sequence.

Helices 7 and 10:
(SEQ ID NO: 39)
PYSDELRQRLAARLEALKENGGPVLESFKVSFLSALEEYTKKLN.

The sequence identified as "ApoA-I Helices 7 and 10" represents a 44-mer ApoA1 chimeric sequence having a 22mer of helix 7 joined to an 22 of helix 10 by a proline residue. The amino acids underlined in the above sequence represent the negatively charged residues which align on the hydrophilic face of the α-helix and correspond to D168, E179 and E223 of apoA-I primary sequence.

Helices 6 and 10:
(SEQ ID NO: 40)
PLGEEMRDRARAHVDALRTHLAPVLESFKVSFLSALEEYTKKLN.

The sequence identified as "ApoA-I Helices 6 and 10" represents a 44-mer ApoA1 chimeric sequence having a 22mer of helix 6 joined to an 22-mer of helix 10 by a proline residue. The amino acids underlined in the above sequence represent the negatively charged residues which align on the hydrophilic face of the α-helix and correspond to D150, D157 and E223 of apoA-I primary sequence.

Helices 9 and 1:
(SEQ ID NO: 41)
PALEDLRQGLLLKLLDNWDSVTSTFSKLREQLG.

The sequence identified as "ApoA-I Helices 9 and 1" represents a 33mer ApoA1 chimeric sequence (i.e. naturally non-adjacent subsequences) having an 11 mer of helix 9 joined to a 22mer of helix 1. The amino acids underlined in the above sequence represent the negatively charged residues which align on the hydrophilic face of the α-helix and correspond to E62, E212 and D51 of apoA-I primary sequence.

Residues 216-267:
(SEQ ID NO: 51)
ARME<u>E</u>MGSRTR<u>D</u>RLDEVK<u>E</u>QVAEVRAKLE<u>E</u>QAQQIRLQAEAF
QARLKSWFE.

The sequence identified as "ApoE 216-267" represents a 51 mer of ApoE native sequence having forming a continuous helical stretch. The amino acids underlined in the above sequence represent the negatively charged residues which align on the hydrophilic face of the α-helix and correspond to residues E220, D227, E234, and E245.

Residues 62-94:
(SEQ ID NO: 10)
PFATELH<u>E</u>RLAKDS<u>E</u>KLK<u>EE</u>IGK<u>E</u>L<u>EE</u>LRARLL.

The sequence identified as "ApoA-IV 62-94" represents 33mer of ApoA-IV native sequence forming a continuous helical stretch. The underlined amino acids in the above sequence corresponded to aligned negatively charged residues E69, E80 and E87 of apoA-IV.

Residues 161-204:
(SEQ ID NO: 12)
PHA<u>D</u>ELKAKIDQNV<u>EE</u>LKGRLTPYA<u>D</u>EFKVKIDQTVEELRRSLA.

The sequence identified as "ApoA-IV 161-204" represents a 44mer of ApoA-IV native sequence having a 22mer linked to a 22-mer with a proline residue. The underlined amino acids in the above sequence corresponded to aligned negatively charged residues D164, E175, and D186 of apoA-IV.

Residues 183-226:
(SEQ ID NO: 15)
PYA<u>D</u>EFKVKIDQTV<u>EE</u>LRRSLAPYAQ<u>D</u>TQEKLNHQLEGLTFQMK.

The sequence identified as "ApoA-IV 1831-226" represents a 44mer of ApoA-IV native sequence. The underlined amino acids in the above sequence corresponded to aligned negatively charged residues E187, E198, and D209 of apoA-IV.

Residues 205-248:
(SEQ ID NO: 17)
PYAQDTQ<u>E</u>KLNHQL<u>E</u>GLTFQMKKNA<u>EE</u>LKARISASAEELRQRLA.

The sequence identified as "ApoA-IV 62-94" represents 44mer of ApoA-IV native sequence. The underlined amino acids in the above sequence corresponded to aligned negatively charged residues E212, E219, and E230 of apoA-IV.

Residues 25-57:
(SEQ ID NO: 21)
LISRIKQS<u>E</u>LSAKMR<u>E</u>WFS<u>E</u>TFQKVK<u>E</u>KLKIDS.

The sequence identified as "ApoCI 25-57" represents a33mer of ApoCI native sequence form a continuous helical stretch. The underlined amino acids in the above sequence correspond to aligned negatively charged residues E33, E40, E44, and E51 of apoC-I.

Residues 12-42:
(SEQ ID NO: 24)
PTFLTQVK<u>E</u>SLSSYW<u>E</u>SAKTAAQNLY<u>E</u>KTYL.

The sequence identified as "ApoCII 12-42" represents a 31 mer of ApoCII native sequence forming a continuous helical stretch. The underlined amino acids in the above sequence correspond to aligned negatively charged residues E20, E27, and E38 of apoC-II.

Example 20

Antioxidant Activity of a Thiol-Bearing Peptide Comprising ApoA-I Helices 9 and 10

A cysteine residue will be added to the lipid-water interface of the 9/10 structural element (33-mer) at position 215 corresponding to a R→C interchange similar to that produced by the apoA-I$_{Milano}$ mutation. Antioxidant activity of the thiol-bearing peptide will be compared to a cysteine free-9/10 peptide using native HDL and aqueous peroxides.

Lipoprotein oxidation studies: The apoE-free fraction of HDL$_3$ (d=1.15-1.21 g/ml) will be isolated from human plasma by sequential ultracentrifugation. The isolated HDL$_3$ will be passed through a Heparin Sepharose column to ensure removal of apoE and the unbound apoE-free fraction concentrated for oxidation studies. SDS-PAGE and Western blot analyses will be performed to demonstrate that the isolated particles do not possess apoE. HDL$_3$ (1 mg protein/ml) in PBS-EDTA will be exposed to AAPH in the presence and absence of synthetic peptides based on the 9/10 helical segment and conjugated dienes assessed. The concentration of peptides will be systematically varied (10-400 μg/ml) to determine if peptide mimetics extend lag-times and reduce rates of lipid peroxidation in a concentration dependent manner consistent with a chain-breaking antioxidant activity.

Oxidation of reconstituted HDL: Lipid peroxidation will be initiated using AAPH (2,2'-azobis[2-amidinopropane]hydrochloride) which decomposes in a temperature dependent manner at a constant, defined rate (57). Reconstituted HDL (1 mg protein/ml) composed of WT-apoA-I or the apoA-I helical peptides, in PBS-EDTA (pH=7.4), will be exposed to AAPH. The concentration of AAPH (1-5 mM) will be varied. This will permit reproducible parameters of lag-times and rates of lipid peroxidation to be established as well as to determine whether apoA-I helices 9 and 10 inhibits lipid peroxidation over a wide range of aqueous peroxide concentrations. Lipid peroxidation will be assessed continuously by quantifying conjugated dienes (absorbance at 234 nm) using a temperature controlled, 5-chamber UV spectrophotometer at 37° C. Tangents will be drawn to segments of the absorbance curves corresponding to the lag- and propagation-phases, and the length of the lag-phase determined by the intercept of these two tangents. Rates of lipid peroxidation will be calculated from the slope of the tangents. It is predicted that apoA-I helices 9 and 10 will act as a chain-breaking antioxidant extending the lag-phase and reducing rates of lipid peroxidation compared to reconstituted HDL composed of either WT-apoA-I or the peptide. We further anticipate that line-curves will be sigmoidal and the maximum amount of oxidation will reach the same levels regardless of the apolipoprotein used. Power calculations were performed in advance to determine the number of experiments required for demonstrating statistical significance. Analyses were based on the variance (20%) in lag-times and rates of lipid peroxidation. Levels of significance were set at $p<0.05$ with a probability of 0.9 of obtaining true differences (of at least 30%). It was calculated that an n=4 will be sufficient to establish significance. Means±SD will be calculated for lag-times and rates. Student's unpaired t-test will be used to determine statistical differences using $p<0.05$ as the criteria for significance. In a parallel set of experiments, lipid peroxidation will be initiated with AMVN, an lipophilic analog of AAPH.

The above examples are provided to illustrate the invention but not to limit its scope. Other variants of the invention will be readily apparent to one of ordinary skill in the art and are encompassed by the appended claims. All publications, databases, Genbank Accession Nos., and patents cited herein are hereby incorporated by reference

What is claimed is:

1. An isolated peptide that has a cholesterol efflux mediating activity and an ABCA stabilization activity, comprising an amphipathic alpha helix of 18-60 amino acids in length comprising an engineered helical segment, said engineered helical segment comprising: a polar face and a nonpolar face, wherein the polar face comprises an alignment of at least 3 acidic amino acids, wherein each of the at least 3 acidic amino acids is positioned at 2-3 helical turns from one another along the long-axis of the helix; and had the following characteristics in comparison to a helical segment of a native protein:

(a) said engineered helical segment comprises from 1 to 3 amino acid substitutions compared with the sequence of the helical segment of the native protein, and at least one of the substitutions creates the alignment of at least 3 acidic amino acids; or (b) said helical segment comprises from 1 to 3 amino acid substitutions compared with the helical segment of the native protein and a deletion of 1 to 4 amino acid residues compared with the sequence of the helical segment of the native protein where the deletion creates the alignment of at least 3 acidic amino acids; and said native protein is selected from the group consisting of human Apo A-I, human Apo A-II, human Apo A-IV, human Apo E, human Apo C-I, human Apo C-II, human Apo C-III, and human serum amyloid.

2. The peptide of claim 1, wherein the ABCA stabilization activity is selected from the group consisting of ABCA1 and ABCA7.

3. The peptide of claim 1, wherein said peptide has an antioxidant activity.

4. The peptide of claim 3, wherein at least one native amino acid residue at or near the polar/nonpolar interface of the amphipathic alpha helix is substituted with a cysteine.

5. The peptide of claim 1, wherein said peptide has an anti-inflammatory activity.

6. The peptide of claim 1, wherein the peptide comprises at least one D amino acid.

7. The peptide of claim 1, wherein the carboxy terminus of the peptide comprises a D amino acid and the amino terminus of the peptide comprises a D amino acid.

8. The peptide of claim 1, wherein the peptide comprises all D amino acids.

9. The peptide of claim 1, wherein the helical segment of the native protein is present in a sequence selected from the group consisting of: helix 1 (amino acids 44-65) of human Apo A-I, helix 10 (amino acids 220-238) of human Apo A-I, amino acids 1-51 of human Apo A-II, amino acids 5-32 of human Apo A-II, amino acids 62-94 of human Apo A-IV, amino acids 66-90 of human Apo A-IV, amino acids 183-204 of human Apo A-IV, amino acids 183-226 of human Apo A-IV, amino acids 205-226 of human Apo A-IV, amino acids 161-204 of human Apo A-IV, amino acids 161-182 of human Apo A-IV, amino acids 205-248 of human Apo A-IV, amino acids 227-248 of human Apo A-IV, amino acids 117-138 of human Apo A-IV, amino acids 138-160 of human Apo A-IV, amino acids of 25-57 human Apo C-I, amino acids 6-27 of human Apo C-I, amino acids 29-53 of human Apo C-I, amino acids 12-42 of human Apo C-II, amino acids 16-40 of human Apo C-II, amino acids 43-68 of human Apo C-II, amino acids 37-69 of human Apo C-III, amino acids 45-69 of human Apo C-III, the C terminal domain (amino acids 216-299) of human Apo E, amino acids 216-248 of human Apo E, amino acids 216-237 of human Apo E, amino acids 238-266 of human Apo E, amino acids 267-299 of human Apo E, amino acids 238-263 of human Apo E, amino acids 1-36 of human serum amyloid A, amino acids 1-34 of human serum amyloid A amino acids 5-29 of human serum amyloid A, and amino acids 53-78 of human serum amyloid A.

10. The peptide of claim 1, wherein the helix comprises EVRAKLEEWFQQIRLQAEEFQARLKS (SEQ ID NO: 9).

11. The peptide of claim 1, further comprising a second amphipathic alpha helix, wherein the second helix is from a human protein selected from the group consisting of Apo A-I, Apo C-II, Apo A-IV, Apo E, Apo C-I, Apo C-II, Apo C-III, serum amyloid A, and combinations thereof,
wherein said peptide has a cholesterol efflux mediating activity and an ABCA stabilization activity.

12. The peptide of claim 11, wherein the second amphipathic alpha helix comprises a sequence selected from the group consisting of: helix 1 (amino acids 44-65) of Apo A-I, helix 6 (amino acids 145-162) of Apo A-I, helix 7 (amino acids 167-184) of Apo A-I, helix 9 (amino acids 209-219) of Apo A-I, helix 10 (amino acids 220-238) of Apo A-I, amino acids 1-51 of Apo A-II, amino acids 5-32 of Apo A-II, amino acids 62-94 of Apo A-IV, amino acids 66-90 of Apo A-IV, amino acids 183-204 of Apo A-IV, amino acids 183-226 of Apo A-IV, amino acids 205-226 of Apo A-IV, amino acids 161-204 of Apo A-IV, amino acids 161-182 of Apo A-IV, amino acids 205-248 of Apo A-IV, amino acids 227-248 of Apo A-IV, amino acids 117-138 of Apo A-IV, amino acids 138-160 of Apo A-IV, amino acids of 25-57 Apo C-I, amino acids 6-27 of Apo C-I, amino acids 29-53 of Apo C-I, amino acids 12-42 of Apo C-II, amino acids 16-40 of Apo C-II, amino acids 43-68 of Apo C-II, amino acids 37-69 of Apo C-III, amino acids 45-69 of Apo C-III, the C terminal domain (amino acids 216-299) of Apo E, amino acids 216-248 of Apo E, amino acids 216-237 of Apo E, amino acids 238-266 of Apo E, a amino acids 267-299 of Apo E, amino acids 238-263 of Apo E, amino acids 1-36 of serum amyloid A, amino acids 1-34 of serum amyloid A amino acids 5-29 of serum amyloid A, and amino acids 53-78 of serum amyloid A.

13. A pharmaceutical composition comprising a peptide of claim 1 and a pharmaceutically acceptable carrier.

14. The pharmaceutical composition of claim 13, further comprising a therapeutic agent for treating cardiovascular disease.

15. The pharmaceutical composition of claim 14, wherein the therapeutic agent is selected from the group consisting of: a statin, a bile acid binder, a platelet clumping inhibitor, nicotinamide, a PPAR activator, vitamin E, and combinations thereof.

16. The peptide of claim 1, wherein the amphiphathic helix is from 20 to 44 amino acids in length.

17. The peptide of claim 1, wherein the amphipathic helix is from 22 to 26 amino acids in length.

18. The peptide of claim 1, wherein the helical segment of the native protein is present in the C terminal domain (amino acids 216-299) of human Apo E.

19. The peptide of claim 18, wherein the helical segment of the native protein is present in a sequence selected from the group consisting of amino acids 216-248 of human Apo E, amino acids 216-237 of human Apo E, amino acids 238-266 of human Apo E, amino acids 267-299 of human Apo E, and amino acids 238-263 of human Apo E.

* * * * *